United States Patent
Faler et al.

(10) Patent No.: US 11,041,031 B2
(45) Date of Patent: Jun. 22, 2021

(54) NON-COORDINATING ANION TYPE ACTIVATORS CONTAINING CATION HAVING BRANCHED ALKYL GROUPS

(71) Applicant: ExxonMobil Chemical Patents Inc., Baytown, TX (US)

(72) Inventors: Catherine A. Faler, Houston, TX (US); Margaret T. Whalley, Houston, TX (US); John R. Hagadorn, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 104 days.

(21) Appl. No.: 16/394,197

(22) Filed: Apr. 25, 2019

(65) Prior Publication Data

US 2019/0330392 A1    Oct. 31, 2019

Related U.S. Application Data

(60) Provisional application No. 62/662,972, filed on Apr. 26, 2018, provisional application No. 62/769,208, filed on Nov. 19, 2018.

(51) Int. Cl.

| | | |
|---|---|---|
| *C07F 5/02* | (2006.01) | |
| *C08F 4/643* | (2006.01) | |
| *C07C 211/63* | (2006.01) | |
| *C07C 211/64* | (2006.01) | |
| *C08F 10/02* | (2006.01) | |
| *C08F 10/06* | (2006.01) | |
| *C08F 10/14* | (2006.01) | |
| *C08F 4/659* | (2006.01) | |

(52) U.S. Cl.
CPC ............ *C08F 10/02* (2013.01); *C07C 211/63* (2013.01); *C07C 211/64* (2013.01); *C07F 5/027* (2013.01); *C08F 4/643* (2013.01); *C08F 4/65908* (2013.01); *C08F 10/06* (2013.01); *C08F 10/14* (2013.01)

(58) Field of Classification Search
CPC ...... C07F 5/02; C08F 4/65908; C07C 211/63; C07C 211/64
See application file for complete search history.

(56) References Cited

U.S. PATENT DOCUMENTS

| | | | | |
|---|---|---|---|---|
| 5,919,983 | A | 7/1999 | Rosen et al. | C08F 10/00 |
| 6,121,185 | A | 9/2000 | Rosen et al. | C08F 10/00 |
| 7,087,602 | B2 | 8/2006 | Thomas et al. | C07D 401/12 |
| 7,101,940 | B2 | 9/2006 | Schottek et al. | C07F 5/062 |
| 7,799,879 | B2 | 9/2010 | Crowther et al. | C08F 210/06 |
| 7,985,816 | B2 | 7/2011 | Crowther et al. | C08F 210/06 |
| 8,580,902 | B2 | 11/2013 | Crowther et al. | C08F 210/06 |
| 8,642,497 | B2 | 2/2014 | Berris | C07D 241/02 |
| 8,835,587 | B2 | 9/2014 | Crowther et al. | C08F 210/06 |
| 9,611,280 | B2 | 4/2017 | Takaishi et al. | C07F 5/02 |
| 2002/0062011 | A1 | 5/2002 | Campbell et al. | C07F 17/00 |
| 2007/0021575 | A1 | 1/2007 | Rodriguez | C07F 5/027 |
| 2009/0318644 | A1 | 12/2009 | Brant et al. | C08F 210/06 |
| 2012/0316303 | A1 | 12/2012 | Hanton et al. | C07C 2/36 |
| 2014/0256893 | A1 | 9/2014 | Hagadorn et al. | C08F 4/76 |
| 2015/0203602 | A1 | 7/2015 | Sun et al. | C07F 5/02 |
| 2019/0330139 | A1 | 10/2019 | Faler et al. | C07F 5/027 |
| 2019/0330394 | A1 | 10/2019 | Faler et al. | C07C 211/48 |

FOREIGN PATENT DOCUMENTS

| | | | | |
|---|---|---|---|---|
| WO | WO2002/002577 | | 1/2002 | C07F 17/00 |
| WO | WO2010/014344 | | 2/2010 | C08F 10/06 |
| WO | WO2012/170202 | | 12/2012 | C07F 7/08 |

OTHER PUBLICATIONS

U.S. Appl. No. 62/662,972, filed Apr. 26, 2018, Faler, Catherine A. et al.
CAS No. 909721-53-5 and CAS No. 943521-08-2.

*Primary Examiner* — Caixia Lu

(57) ABSTRACT

The present disclosure provides borate or aluminate activators comprising cations having branched alkyl groups, catalyst systems comprising, and methods for polymerizing olefins using such activators. Specifically, the present disclosure provides activator compounds represented by Formula: $[R^1R^2R^3EH]_d^+[M^{k+}Q_n]^{d-}$, wherein: E is nitrogen or phosphorous; d is 1, 2 or 3; k is 1, 2, or 3; n is 1, 2, 3, 4, 5, or 6; n−k=d; each of $R^1$, $R^2$, and $R^3$ is independently $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms; M is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, provided that at least one of $R^1$, $R^2$, and $R^3$ is a branched alkyl.

18 Claims, 2 Drawing Sheets

NON-COORDINATING ANION TYPE ACTIVATORS CONTAINING CATION HAVING BRANCHED ALKYL GROUPS

PRIORITY

This application claims priority to and the benefit of U.S. Ser. No. 62/662,972, filed Apr. 26, 2018 and U.S. Ser. No. 62/769,208, filed Nov. 19, 2018.

CROSS REFERENCE TO RELATED APPLICATIONS

This invention also relates to:
1) U.S. patent application Ser. No. 16/394,174 filed concurrently herewith, entitled "Alkyl Ammonium (Fluoroaryl) Borate Activators", which claims priority to and the benefit of U.S. Ser. No. 62/662,981, filed Apr. 26, 2018; and
2) U.S. patent application Ser. No. 16/394,166 filed concurrently herewith, entitled "Non-Coordinating Anion Type Activators Containing Cation Having Large Alkyl Groups", which claims priority to and the benefit of U.S. Ser. No. 62/662,972, filed Apr. 26, 2018 and U.S. Ser. No. 62/769,208, filed Nov. 19, 2018.

FIELD

The present disclosure provides group 13 metallate (such as borate or aluminate) activators, catalyst systems comprising, and methods for polymerizing olefins using such activators.

BACKGROUND

Polyolefins are widely used commercially because of their robust physical properties. Polyolefins are typically prepared with a catalyst that polymerizes olefin monomers. Therefore, there is interest in finding new catalysts and catalyst systems that provide polymers having improved properties.

Catalysts for olefin polymerization are often based on metallocenes as catalyst precursors, which are activated either with an alumoxane or an activator containing a non-coordinating anion. A non-coordinating anion, such as tetrakis(pentafluorophenyl)borate, is capable of stabilizing the resulting metal cation of the catalyst. Because such activators are fully ionized and the corresponding anion is highly non-coordinating, such activators can be effective as olefin polymerization catalyst activators. However, because they are ionic salts, such activators are insoluble in aliphatic hydrocarbons and only sparingly soluble in aromatic hydrocarbons. It is desirable to conduct most polymerizations of α-olefins in aliphatic hydrocarbon solvents due to the compatibility of such solvents with the olefin monomer and in order to reduce the aromatic hydrocarbon content of the resulting polymer product. Typically, ionic salt activators are added to such polymerizations in the form of a solution in an aromatic solvent such as toluene. The use of even a small quantity of such an aromatic solvent for this purpose is undesirable since it must be removed in a post-polymerization devolatilization step and separated from other volatile components, which is a process that adds significant cost and complexity to any commercial process. In addition, the activators often exist in the form of an oily, intractable material which is not readily handled and metered or precisely incorporated into the reaction mixture.

In addition, polymer products, such as isotactic polypropylene, formed using such activators can have lower molecular weights (e.g., Mw less than about 100,000) and a high melt temperature (Tm) (e.g., Tm greater than about 110° C.).

U.S. Pat. No. 5,919,983 discloses polymerization of ethylene and octene using a catalyst system comprising [(C$_{18}$)$_2$MeN)]$^+$[B(PhF$_5$)$_4$] activator having four fluoro-phenyl groups bound to the boron atom and two linear Cis groups bound to the nitrogen, as well as describing other linear groups at column 3, line 51 et seq.

U.S. Pat. No. 8,642,497 discloses the preparation of N,N-dimethylanilinium tetrakis(heptafluoronaphth-2-yl)borate anion.

US 2003/0013913 (granted as U.S. Pat. No. 7,101,940) discloses various activators such as N,N-dimethylcyclohexylammoniumtetrakis(pentafluorophenyl)borate [0070], and N,N-diethylbenzylammoniumtetrakis(pentafluorophenyl)borate [0124].

US 2002/0062011 discloses phenyl dioctadecylammonium(hydroxyphenyl) tris(pentafluorophenyl) borate at paragraph [0200] and (pentafluorophenyl) dioctadecylammonium tetrakis(pentafluorophenyl) borate at paragraph [0209].

U.S. Pat. Nos. 7,799,879, 7,985,816, 8,580,902, 8,835,587, and WO2010/014344 describe ammonium borate activators that include some that use a tetrakis(heptafluoronaphth-2-yl)borate anion.

There is a need for activators that are soluble in aliphatic hydrocarbons and capable of producing polyolefins having a high molecular weight and high melt temperature. Likewise, there is a need for activators that are soluble in aliphatic hydrocarbons and capable of producing polyolefins at high activity levels where the polymers preferably have high molecular weight and/or high melt temperature.

References of interest include: WO 2002/002577; U.S. Pat. Nos. 7,087,602; 8,642,497; 6,121,185; 8,642,497; US2015/0203602; and U.S. Ser. No. 62/662,972 filed Apr. 26, 2018, CAS number 909721-53-5, CAS number 943521-08-2.

SUMMARY

This invention relates to activator compounds represented by Formula (AI):

$$[R^1R^2R^3EH]_d^+[M^{k+}Q_n]^{d-} \qquad (AI)$$

wherein:
E is nitrogen or phosphorous;
d is 1, 2 or 3; k is 1, 2, or 3; n is 1, 2, 3, 4, 5, or 6; n−k=d; each of R$^1$, R$^2$, and R$^3$ is independently H, C$_1$-C$_{40}$ branched or linear alkyl or C$_5$-C$_{50}$-aryl, wherein each of R$^1$, R$^2$, and R$^3$ is independently unsubstituted or substituted with at least one of halide, C$_5$-C$_{50}$ aryl, C$_6$-C$_{35}$ arylalkyl, C$_6$-C$_{35}$ alkylaryl and, in the case of the C$_5$-C$_{50}$-aryl, C$_1$-C$_{50}$ alkyl; wherein R$^1$, R$^2$, and R$^3$ together comprise 15 or more carbon atoms, and provided that at least one of R$^1$, R$^2$, and R$^3$ is a branched alkyl (such as a C$_3$-C$_{40}$, or C$_7$ to C$_{40}$ branched alkyl); M is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

This invention relates to activator compounds represented by Formula (AI):

$$[R^1R^2R^3EH]_d^+[M^{k+}Q_n]^{d-} \qquad (AI)$$

wherein:

E is nitrogen or phosphorous;

d is 1, 2 or 3; k is 1, 2, or 3; n is 1, 2, 3, 4, 5, or 6; n−k=d;

$R^1$ is a $C_1$-$C_{20}$ alkyl group (preferably a $C_1$-$C_{10}$ alkyl group), wherein $R^1$ is optionally substituted;

each of $R^2$ and $R^3$ is independently an optionally substituted $C_1$-$C_{40}$ branched or linear alkyl group or a meta and/or para-substituted phenyl group, where the meta and para substituents are, independently, an optionally substituted $C_1$ to $C_{40}$ hydrocarbyl group, an optionally substituted alkoxy group, an optionally substituted silyl group, a halogen, or a halogen containing group, wherein $R^1$, $R^2$, and $R^3$ together comprise 15 or more carbon atoms and at least one of $R^1$, $R^2$, and $R^3$ is a $C_3$-$C_{40}$ branched alkyl, alternately $C_7$-$C_{40}$ branched alkyl;

M is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

This invention also relates to activator compounds represented by Formula (AI):

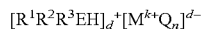  (AI)

wherein:

E is nitrogen or phosphorous;

d is 1, 2 or 3; k is 1, 2, or 3; n is 1, 2, 3, 4, 5, or 6; n−k=d;

$R^1$ is methyl;

each of $R^2$ and $R^3$ is independently $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms, and provided that at least one of $R^1$, $R^2$, and $R^3$ is a $C_3$-$C_{40}$ branched alkyl (such as a $C_7$ to $C_{40}$ branched alkyl);

M is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

This invention also relates to activator compounds represented by Formula (I):

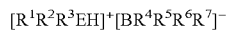  (I)

wherein:

E is nitrogen or phosphorous;

each of $R^1$, $R^2$, and $R^3$ is independently $C_1$-$C_{40}$ linear or branched alkyl or $C_5$-$C_{50}$-aryl (such as $C_5$ to $C_{22}$), wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms provided that at least one of $R^1$, $R^2$, and $R^3$ is a $C_3$-$C_{40}$ branched alkyl (such as a $C_7$ to $C_{40}$ branched alkyl); and each of $R^4$, $R^5$, $R^6$, and $R^7$ is phenyl or naphthyl, wherein at least one of $R^4$, $R^5$, $R^6$, and $R^7$ is substituted with from one to seven fluorine atoms.

In yet another embodiment, the present disclosure provides a catalyst system comprising an activator as described herein and a catalyst compound.

In yet another embodiment, the present disclosure provides a catalyst system comprising an activator as described herein, a catalyst support, and a catalyst compound.

In still another embodiment, the present disclosure provides a polymerization process comprising a) contacting one or more olefin monomers with a catalyst system comprising: i) an activator as described herein, ii) a catalyst compound, and iii) optional support.

In still another embodiment, the present disclosure provides a polyolefin formed by a catalyst system and or method of the present disclosure.

DETAILED DESCRIPTION

Definitions

Figures 1, 2:
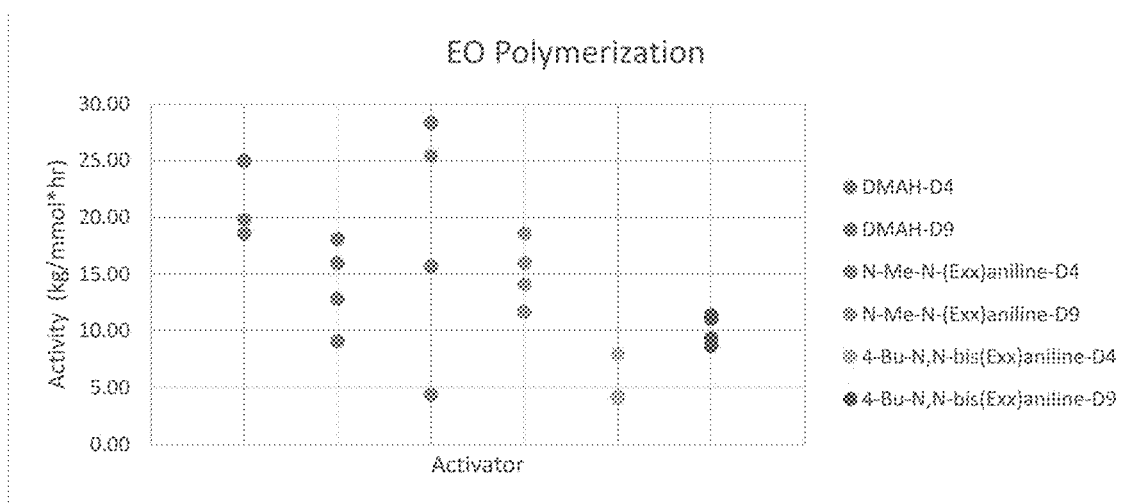
FIG. 1 is a graph illustrating activity data versus activator equivalent for the data in Table A.
FIG. 2 is a graph illustrating octene incorporation versus activator equivalent for the data in Table A.
Figure 3:
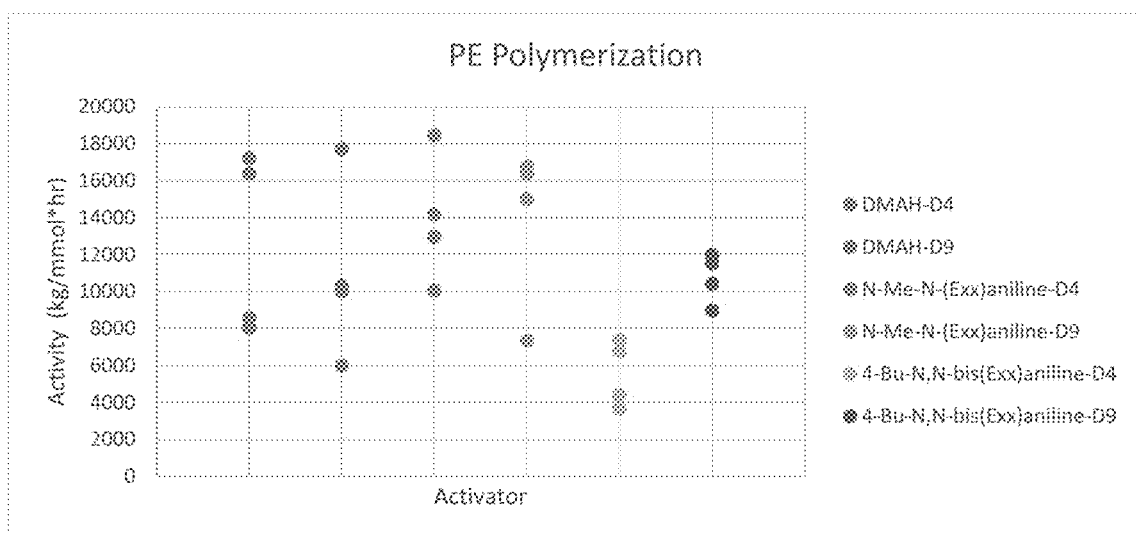
FIG. 3 is a graph illustrating activity data versus activator equivalent for the data in Table B.

Unless otherwise noted all melt temperatures (Tm) are DSC second melt and are determined using the following DSC procedure according to ASTM D3418-03. Differential scanning calorimetric (DSC) data are obtained using a TA Instruments model Q200 machine. Samples weighing about 5 to about 10 mg are sealed in an aluminum hermetic sample pan. The DSC data are recorded by first gradually heating the sample to about 200° C. at a rate of about 10° C./minute. The sample is kept at about 200° C. for about 2 minutes, then cooled to about −90° C. at a rate of about 10° C./minute, followed by an isothermal for about 2 minutes and heating to about 200° C. at about 10° C./minute. Both the first and second cycle thermal events are recorded. The melting points reported herein are obtained during the second heating/cooling cycle unless otherwise noted.

All molecular weights are weight average (Mw) unless otherwise noted. All molecular weights are reported in g/mol unless otherwise noted. Melt index (MI) also referred to as I2, reported in g/10 min, is determined according to ASTM D-1238, 190° C., 2.16 kg load. High load melt index (HLMI) also referred to as I21, reported in g/10 min, is determined according to ASTM D-1238, 190° C., 21.6 kg load. Melt index ratio (MIR) is MI divided by HLMI as determined by ASTM D1238.

The specification describes catalysts that can be transition metal complexes. The term complex is used to describe molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal complexes are generally subjected to activation to perform their polymerization or oligomerization function using an activator which is believed to create a cation as a result of the removal of an anionic group, often referred to as a leaving group, from the transition metal.

For the purposes of the present disclosure, the numbering scheme for the Periodic Table Groups is the "New" notation as described in Chemical and Engineering News, 63(5), pg. 27 (1985). Therefore, a "Group 8 metal" is an element from Group 8 of the Periodic Table, e.g., Fe.

The following abbreviations are used through this specification: o-biphenyl is an ortho-biphenyl moiety represented by the structure

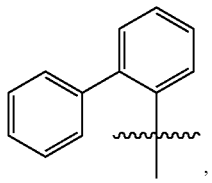 [SMILES: *c1ccccc1-c1ccccc1]

dme is 1,2-dimethoxyethane, Me is methyl, Ph is phenyl, Et is ethyl, Pr is propyl, iPr is isopropyl, n-Pr is normal propyl, cPr is cyclopropyl, Bu is butyl, iBu is isobutyl, tBu is tertiary butyl, p-tBu is para-tertiary butyl, nBu is normal butyl, sBu is sec-butyl, TMS is trimethylsilyl, TIBAL is triisobutylaluminum, TNOAL is tri(n-octyl)aluminum, MAO is methylalumoxane, p-Me is para-methyl, Ph is phenyl, Bn is benzyl (i.e., CH$_2$Ph), THF (also referred to as thf) is tetrahydrofuran, RT is room temperature (and is 23° C. unless otherwise indicated), tol is toluene, EtOAc is ethyl acetate, MeCy is methylcyclohexane, and Cy is cyclohexyl.

Unless otherwise indicated (e.g., the definition of "substituted hydrocarbyl", etc.), the term "substituted" means that at least one hydrogen atom has been replaced with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SIR*, —SiR*$_3$, —GeR*, —GeR*$_3$, —SnR*, —SnR*$_3$, —PbR*$_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a ring structure.

The terms "hydrocarbyl radical," "hydrocarbyl," and "hydrocarbyl group," are used interchangeably throughout this disclosure. Likewise, the terms "group", "radical", and "substituent" are also used interchangeably in this disclosure. For purposes of this disclosure, "hydrocarbyl radical" is defined to be C$_1$-C$_{100}$ radicals of carbon and hydrogen, that may be linear, branched, or cyclic, and when cyclic, aromatic or non-aromatic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like.

Substituted hydrocarbyl radicals are radicals in which at least one hydrogen atom of the hydrocarbyl radical has been replaced with a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SIR*, —SiR*$_3$, —GeR*, —GeR*$_3$, —SnR*, —SnR*$_3$, —PbR*$_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

Substituted cyclopentadienyl, indenyl, tetrahydroindenyl or fluorenyl groups are cyclopentadienyl, indenyl, tetrahydroindenyl or fluorenyl groups where at least one hydrogen atom has been replaced with at least a non-hydrogen group, such as a hydrocarbyl group, a heteroatom, or a heteroatom containing group, such as halogen (such as Br, Cl, F or I) or at least one functional group such as —NR*$_2$, —OR*, —SeR*, —TeR*, —PR*$_2$, —AsR*$_2$, —SbR*$_2$, —SR*, —BR*$_2$, —SIR*, —SiR*$_3$, —GeR*, —GeR*$_3$, —SnR*, —SnR*$_3$, —PbR*$_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a ring structure.

Halocarbyl radicals (also referred to as halocarbyls, halocarbyl groups or halocarbyl substituents) are radicals in which one or more hydrocarbyl hydrogen atoms have been substituted with at least one halogen (e.g., F, Cl, Br, I) or halogen-containing group (e.g., CF$_3$). Substituted halocarbyl radicals are radicals in which at least one halocarbyl hydrogen or halogen atom has been substituted with at least one functional group such as NR*2, OR*, SeR*, TeR*, PR*2, AsR*2, SbR*2, SR*, BR*2, SiR*3, GeR*3, SnR*3, PbR*3, and the like or where at least one non-carbon atom or group has been inserted within the halocarbyl radical such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Ge(R*)$_2$—, —Sn(R*)$_2$—, —Pb(R*)$_2$— and the like, where R* is independently a hydrocarbyl or halocarbyl radical provided that at least one halogen atom remains on the original halocarbyl radical. Additionally, two or more R* may join together to form a substituted or unsubstituted saturated, partially unsaturated or aromatic cyclic or polycyclic ring structure.

Hydrocarbylsilyl groups, also referred to as silylcarbyl groups, are radicals in which one or more hydrocarbyl hydrogen atoms have been substituted with at least one SiR*3 containing group or where at least one —Si(R*)$_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Silylcarbyl radicals can be bonded via a silicon atom or a carbon atom.

Substituted silylcarbyl radicals are silylcarbyl radicals in which at least one hydrogen atom has been substituted with at least one functional group such as NR*$_2$, OR*, SeR*, TeR*, PR*$_2$, AsR*$_2$, SbR*$_2$, SR*, BR*$_2$, GeR*$_3$, SnR*$_3$, PbR$_3$ and the like or where at least one non-hydrocarbon atom or group has been inserted within the silylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Ge(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

Germylcarbyl radicals (also referred to as germylcarbyls, germylcarbyl groups or germylcarbyl substituents) are radicals in which one or more hydrocarbyl hydrogen atoms have been substituted with at least one GeR*$_3$ containing group or where at least one —Ge(R*)$_2$— has been inserted within the hydrocarbyl radical where R* is independently a hydrocarbyl or halocarbyl radical, and two or more R* may join together to form a substituted or unsubstituted saturated, partially unsaturated or aromatic cyclic or polycyclic ring structure. Germylcarbyl radicals can be bonded via a germanium atom or a carbon atom.

Substituted germylcarbyl radicals are germylcarbyl radicals in which at least one hydrogen atom has been substituted with at least one functional group such as $NR^*_2$, $OR^*$, $SeR^*$, $TeR^*$, $PR^*_2$, $AsR^*_2$, $SbR^*_2$, $SR^*$, $BR^*_2$, $SiR^*_3$, $SnR^*_3$, $PbR_3$ and the like or where at least one non-hydrocarbon atom or group has been inserted within the germylcarbyl radical, such as —O—, —S—, —Se—, —Te—, —N(R*)—, =N—, —P(R*)—, =P—, —As(R*)—, =As—, —Sb(R*)—, =Sb—, —B(R*)—, =B—, —Si(R*)$_2$—, —Sn(R*)$_2$—, —Pb(R*)$_2$— and the like, where R* is independently a hydrocarbyl or halocarbyl radical, and two or more R* may join together to form a substituted or unsubstituted saturated, partially unsaturated or aromatic cyclic or polycyclic ring structure.

The terms "alkyl radical," and "alkyl" are used interchangeably throughout this disclosure. For purposes of this disclosure, "alkyl radicals" are defined to be $C_1$-$C_{100}$ alkyls that may be linear, branched, or cyclic. Examples of such radicals can include methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like. Substituted alkyl radicals are radicals in which at least one hydrogen atom of the alkyl radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —$OR^*$, —$SeR^*$, —$TeR^*$, —$PR^*_2$, —$AsR^*_2$, —$SbR^*_2$, —$SR^*$, —$BR^*_2$, —$SiR^*$, —$SiR^*_3$, —$GeR^*$, —$GeR^*_3$, —$SnR^*$, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring.

The term "branched alkyl" means that the alkyl group contains a tertiary or quaternary carbon (a tertiary carbon is a carbon atom bound to three other carbon atoms. A quaternary carbon is a carbon atom bound to four other carbon atoms). For example, 3,5,5 trimethylhexylphenyl is an alkyl group (hexyl) having three methyl branches (hence, one tertiary and one quaternary carbon) and thus is a branched alkyl bound to a phenyl group. Unless otherwise indicated a branched alkyl includes all isomers thereof.

The term "alkenyl" means a straight-chain, branched-chain, or cyclic hydrocarbon radical having one or more carbon-carbon double bonds. These alkenyl radicals may be substituted. Examples of suitable alkenyl radicals can include ethenyl, propenyl, allyl, 1,4-butadienyl cyclopropenyl, cyclobutenyl, cyclopentenyl, cyclohexenyl, cyclooctenyl and the like.

The term "arylalkenyl" means an aryl group where a hydrogen has been replaced with an alkenyl or substituted alkenyl group. For example, styryl indenyl is an indene substituted with an arylalkenyl group (a styrene group).

The term "alkoxy", "alkoxyl", or "alkoxide" means an alkyl ether or aryl ether radical wherein the term alkyl is as defined above and the term aryl is as defined below. Examples of suitable alkyl ether radicals can include methoxy, ethoxy, n-propoxy, iso-propoxy, n-butoxy, iso-butoxy, sec-butoxy, tert-butoxy, phenoxy, and the like.

The term "aryl" or "aryl group" means a carbon-containing aromatic ring such as phenyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic.

Heterocyclic means a cyclic group where a ring carbon atom (or two or three ring carbon atoms) has been replaced with a heteroatom, such as N, O, or S. A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylaminophenyl is a heteroatom substituted ring.

Substituted heterocyclic means a heterocyclic group where at least one hydrogen atom of the heterocyclic radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —$OR^*$, —$SeR^*$, —$TeR^*$, —$PR^*_2$, —$AsR^*_2$, —$SbR^*_2$, —$SR^*$, —$BR^*_2$, —$SIR^*$, —$SiR^*_3$, —$GeR^*$, —$GeR^*_3$, —$SnR^*$, —$SnR^*_3$, —$PbR^*_3$, and the like, where each R* is independently a hydrocarbyl or halocarbyl radical.

A substituted aryl is an aryl group where at least one hydrogen atom of the aryl radical has been substituted with at least a non-hydrogen group, such as a hydrocarbyl group, a heteroatom, or a heteroatom containing group, such as halogen (such as Br, Cl, F or I) or at least one functional group such as —$NR^*_2$, —$OR^*$, —$SeR^*$, —$TeR^*$, —$PR^*_2$, —$AsR^*_2$, —$SbR^*_2$, —$SR^*$, —$BR^*_2$, —$SIR^*$, —$SiR^*_3$, —$GeR^*$, —$GeR^*_3$, —$SnR^*$, —$SnR^*_3$, —$PbR^*_3$, and the like, where each R* is independently a hydrocarbyl or halocarbyl radical, and two or more R* may join together to form a substituted or unsubstituted saturated, partially unsaturated or aromatic cyclic or polycyclic ring structure, or where at least one heteroatom has been inserted within a hydrocarbyl ring, for example 3,5-dimethylphenyl is a substituted phenyl group.

The term "substituted phenyl," or "substituted phenyl group" means a phenyl group having one or more hydrogen groups replaced by a hydrocarbyl, substituted hydrocarbyl, heteroatom or heteroatom containing group, such as halogen (such as Br, Cl, F or I) or at least one functional group such as —$NR^*_2$, —$OR^*$, —$SeR^*$, —$TeR^*$, —$PR^*_2$, —$AsR^*_2$, —$SbR^*_2$, —$SR^*$, —$BR^*_2$, —$SIR^*$, —$SiR^*_3$, —$GeR^*$, —$GeR^*_3$, —$SnR^*$, —$SnR^*_3$, —$PbR^*_3$, and the like, where each R* is independently a hydrocarbyl, halogen, or halocarbyl radical. Preferably the "substituted phenyl" group is represented by the formula:

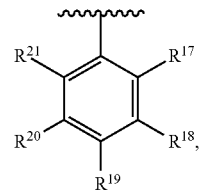

where each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, or a heteroatom-containing group (provided that at least one of $R^{17}$, $R^{18}$, $R^{19}$, $R^{20}$, and $R^{21}$ is not H), or a combination thereof.

A "fluorophenyl" or "fluorophenyl group" is a phenyl group substituted with one, two, three, four or five fluorine atoms.

The term "arylalkyl" means an aryl group where a hydrogen has been replaced with an alkyl or substituted alkyl group. For example, 3,5'-di-tert-butyl-phenyl indenyl is an indene substituted with an arylalkyl group. When an arylalkyl group is a substituent on another group, it is bound to that group via the aryl. For example in Formula (AI), the aryl portion is bound to E.

The term "alkylaryl" means an alkyl group where a hydrogen has been replaced with an aryl or substituted aryl group. For example, phenethyl indenyl is an indene substituted with an ethyl group bound to a benzene group. When an alkylaryl group is a substituent on another group, it is bound to that group via the alkyl. For example in Formula (AI), the alkyl portion is bound to E.

The term "aryloxy" or "aryloxide" means an aryl ether radical wherein the term aryl is as defined above.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl), unless otherwise indicated.

The term "ring atom" means an atom that is part of a cyclic ring structure. Accordingly, a benzyl group has six ring atoms and tetrahydrofuran has 5 ring atoms.

For purposes of the present disclosure, a "catalyst system" is a combination of at least one catalyst compound, an activator, and an optional support material. The catalyst systems may further comprise one or more additional catalyst compounds. For the purposes of the present disclosure, when catalyst systems are described as comprising neutral stable forms of the components, it is well understood by one of ordinary skill in the art, that the ionic form of the component is the form that reacts with the monomers to produce polymers. Catalysts of the presented disclosure and activators represented by Formula (I) or (AI) are intended to embrace ionic forms in addition to the neutral forms of the compounds.

"Complex" as used herein, is also often referred to as catalyst precursor, precatalyst, catalyst, catalyst compound, transition metal compound, or transition metal complex. These words are used interchangeably.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments a co-activator can be pre-mixed with the transition metal compound to form an alkylated transition metal compound.

In the description herein, a catalyst may be described as a catalyst precursor, a precatalyst compound, a catalyst compound or a transition metal compound, and these terms are used interchangeably. A polymerization catalyst system is a catalyst system that can polymerize monomers into polymer. An "anionic ligand" is a negatively charged ligand which donates one or more pairs of electrons to a metal ion. A "neutral donor ligand" is a neutrally charged ligand which donates one or more pairs of electrons to a metal ion.

A metallocene catalyst is defined as an organometallic compound with at least one t-bound cyclopentadienyl moiety or substituted cyclopentadienyl moiety (such as substituted or unsubstituted Cp, Ind, or Flu) and more frequently two (or three) t-bound cyclopentadienyl moieties or substituted cyclopentadienyl moieties (such as substituted or unsubstituted Cp, Ind, or Flu). (Cp=cyclopentadienyl, Ind=indenyl, Flu=fluorenyl).

For purposes of the present disclosure, in relation to catalyst compounds, the term "substituted" means that a hydrogen group has been replaced with a hydrocarbyl group, a heteroatom, or a heteroatom containing group. For example, methyl cyclopentadiene (Cp) is a Cp group substituted with a methyl group.

"Catalyst productivity" is a measure of how many grams of polymer (P) are produced using a polymerization catalyst comprising W g of catalyst (cat), over a period of time of T hours; and may be expressed by the following formula: $P/(T \times W)$ and expressed in units of $gPgcat^{-1}hr^{-1}$. "Conversion" is the amount of monomer that is converted to polymer product, and is reported as mol % and is calculated based on the polymer yield and the amount of monomer fed into the reactor. "Catalyst activity" is a measure of the level of activity of the catalyst and is reported as the mass of product polymer (P) produced per mole (or mmol) of catalyst (cat) used (kgP/molcat or gP/mmolCat), and catalyst activity can also be expressed per unit of time, for example, per hour (hr), e.g., (Kg/mmol h).

For purposes herein an "olefin," alternatively referred to as "alkene," is a linear, branched, or cyclic compound comprising carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have a "propylene" content of 35 wt % to 55 wt %, it is understood that the mer unit in the copolymer is derived from propylene in the polymerization reaction and the derived units are present at 35 wt % to 55 wt %, based upon the weight of the copolymer.

For purposes herein a "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" in reference to mer units indicates that the mer units differ from each other by at least one atom or are different isomerically. Accordingly, copolymer, as used herein, can include terpolymers and the like. An oligomer is typically a polymer having a low molecular weight, such an Mn of less than 25,000 g/mol, or less than 2,500 g/mol, or a low number of mer units, such as 75 mer units or less or 50 mer units or less. An "ethylene polymer" or "ethylene copolymer" is a polymer or copolymer comprising at least 50 mole % ethylene derived units, a "propylene polymer" or "propylene copolymer" is a polymer or copolymer comprising at least 50 mole % propylene derived units, and so on.

As used herein, Mn is number average molecular weight, Mw is weight average molecular weight, and Mz is z average molecular weight, wt % is weight percent, and mol % is mole percent. Molecular weight distribution (MWD), also referred to as polydispersity index (PDI), is defined to be Mw divided by Mn.

The term "continuous" means a system that operates without interruption or cessation for a period of time, such as where reactants are continually fed into a reaction zone and products are continually or regularly withdrawn without stopping the reaction in the reaction zone. For example, a continuous process to produce a polymer would be one where the reactants are continually introduced into one or more reactors and polymer product is continually withdrawn.

A "solution polymerization" means a polymerization process in which the polymerization is conducted in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," Ind. Eng. Chem. Res., v. 39, pp. 4627-4633.

A bulk polymerization means a polymerization process in which the monomers and/or comonomers being polymerized are used as a solvent or diluent using little or no inert solvent or diluent. A small fraction of inert solvent might be used as a carrier for catalyst and scavenger. A bulk polymerization system contains less than about 25 wt % of inert solvent or diluent, such as less than about 10 wt %, such as less than about 1 wt %, such as 0 wt %.

The present disclosure relates to activator compounds that can be used in olefin polymerization processes. For example, the present disclosure provides activators, catalyst systems comprising catalyst compounds and activators, and methods for polymerizing olefins using said catalyst systems. In the present disclosure, activators are described that feature ammonium or phosphonium groups with long-chain aliphatic hydrocarbyl groups for improved solubility of the activator in aliphatic solvents, as compared to conventional activator compounds.

The present disclosure relates to activator compounds that can be used in olefin polymerization processes. For example, the present disclosure provides ammonium borate activators, catalyst systems comprising ammonium borate activators, and methods for polymerizing olefins using ammonium borate activators. In the present disclosure, activators are described that feature ammonium groups with long-chain aliphatic hydrocarbyl groups for improved solubility of the activator in aliphatic solvents, as compared to conventional activator compounds. Useful borate groups of the present disclosure include fluoroaryl (such as fluoronaphthyl borates and or fluorophenyl borates). It has been discovered that activators of the present disclosure having certain borate anions have improved solubility in aliphatic solvents, as compared to conventional activator compounds. Activators having a cation as described herein can provide enhanced activity for polymer production.

In another aspect, the present disclosure relates to polymer compositions obtained from the catalyst systems and processes set forth herein. The components of the catalyst systems according to the present disclosure and used in the polymerization processes of the present disclosure, as well as the resulting polymers, are described in more detail herein below.

The present disclosure relates to a catalyst system comprising a transition metal compound and an activator compound of formula (I) or (AI), to the use of an activator compound of formula (I) or (AI) for activating a transition metal compound in a catalyst system for polymerizing olefins, and to processes for polymerizing olefins, the process comprising contacting under polymerization conditions one or more olefins with a catalyst system comprising a transition metal compound and an activator compound of formula (I) or (AI).

The present disclosure also relates to processes for polymerizing olefins comprising contacting, under polymerization conditions, one or more olefins with a catalyst system comprising a transition metal compound and an activator compound of formula (I) or (AI). The weight average molecular weight of the polymer formed can increase with increasing monomer conversion at a given reaction temperature.

The activator compounds of formula (I) and (AI) will be further illustrated below. Any combinations of cations and non-coordinating anions disclosed herein are suitable to be used in the processes of the present disclosure and are thus incorporated herein.

Non-Coordinating Anion (NCA) Activators

The terms "cocatalyst" and "activator" are used herein interchangeably and are defined to be any compound which can activate any one of the catalyst compounds of the present disclosure by converting the neutral catalyst compound to a catalytically active catalyst compound cation. Noncoordinating anion (NCA) means an anion either that does not coordinate to the catalyst metal cation or that does coordinate to the metal cation, but only weakly. The term NCA is also defined to include multicomponent NCA-containing activators, such as N,N-di-isotridecylanilinium tetrakis(perfluoronaphthyl)borate, that contain an acidic cationic group and the non-coordinating anion. The term NCA is also defined to include neutral Lewis acids, such as tris(pentafluoronaphthyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals can include aluminum, gold, and platinum. Suitable metalloids can include boron, aluminum, phosphorus, and silicon. The term non-coordinating anion activator includes neutral activators, ionic activators, and Lewis acid activators.

"Compatible" non-coordinating anions can be those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with the present disclosure are those that are compatible, stabilize the transition metal cation in the sense of balancing its ionic charge at +1, and yet retain sufficient lability to permit displacement during polymerization.

Activators

The present disclosure provides activators, such as ammonium or phosphonium metallate or metalloid activator compounds, comprising ammonium or phosphonium groups with long-chain aliphatic hydrocarbyl groups combined with metallate or metalloid anions, such as borates or aluminates. When an activator of the present disclosure is used with a catalyst compound (such as a group 4 metallocene compound) in an olefin polymerization, a polymer can be formed having a higher molecular weight and melt temperature than polymers formed using comparative activators. Likewise, when an activator of the present disclosure where $R^1$ is methyl is used with a group 4 metallocene catalyst in an olefin polymerization, the catalyst system activity is substantially better than comparative activators, and can form polymers having a higher molecular weight and/or melt temperature vs. polymers formed using comparative activators. In addition, it has been discovered that activators of the present disclosure are soluble in aliphatic solvent.

In one or more embodiments, a 20 wt % mixture of the compound in n-hexane, isohexane, cyclohexane, methylcyclohexane, or a combination thereof, forms a clear homogeneous solution at 25° C., preferably a 30 wt % mixture of the compound in n-hexane, isohexane, cyclohexane, methylcyclohexane, or a combination thereof, forms a clear homogeneous solution at 25° C.

In embodiments of the invention, the activators described herein have a solubility of more than 10 mM (or more than 20 mM, or more than 50 mM) at 25° C. (stirred 2 hours) in methylcyclohexane.

In embodiments of the invention, the activators described herein have a solubility of more than 1 mM (or more than 10 mM, or more than 20 mM) at 25° C. (stirred 2 hours) in isohexane.

In embodiments of the invention, the activators described herein have a solubility of more than 10 mM (or more than 20 mM, or more than 50 mM) at 25° C. (stirred 2 hours) in methylcyclohexane and a solubility of more than 1 mM (or more than 10 mM, or more than 20 mM) at 25° C. (stirred 2 hours) in isohexane.

The present disclosure relates to a catalyst system comprising a transition metal compound and an activator compound as described herein, to the use of such activator compounds for activating a transition metal compound in a catalyst system for polymerizing olefins, and to processes for polymerizing olefins, the process comprising contacting under polymerization conditions one or more olefins with a catalyst system comprising a transition metal compound and such activator compounds, where aromatic solvents, such as toluene, are absent (e.g. present at zero mol %, alternately present at less than 1 mol %, preferably the catalyst system, the polymerization reaction and/or the polymer produced are free of "detectable aromatic hydrocarbon solvent," such as toluene. For purposes of the present disclosure, "detectable aromatic hydrocarbon solvent" means 0.1 mg/m² or more as determined by gas phase chromatography. For purposes of the present disclosure, "detectable toluene" means 0.1 mg/m² or more as determined by gas phase chromatography.

The polyolefins produced herein preferably contain 0 ppm (alternately less than 1 ppm) of aromatic hydrocarbon. Preferably, the polyolefins produced herein contain 0 ppm (alternately less than 1 ppm) of toluene.

The catalyst systems used herein preferably contain 0 ppm (alternately less than 1 ppm) of aromatic hydrocarbon. Preferably, the catalyst systems used herein contain 0 ppm (alternately less than 1 ppm) of toluene.

This invention relates to activator compounds represented by Formula (AI):

$$[R^1R^2R^3EH]_d^+[M^{k+}Q_n]^{d-} \quad (AI)$$

wherein:

E is nitrogen or phosphorous, preferably nitrogen;

d is 1, 2 or 3; k is 1, 2, or 3; n is 1, 2, 3, 4, 5, or 6; n−k=d (preferably 1, 2, 3, or 4); n−k=d (preferably d is 1, 2 or 3; k is 3;

n is 4, 5, or 6, preferably when M is B, n is 4);

each of $R^1$, $R^2$, and $R^3$ is independently $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl;

wherein $R^1$, $R^2$, and $R^3$ together comprise 15 or more carbon atoms, and provided that at least one of $R^1$, $R^2$, and $R^3$ is a branched alkyl, (such as a $C_3$-$C_{40}$ branched alkyl, alternately such as a $C_7$ to $C_{40}$ branched alkyl);

M is an element selected from group 13 of the Periodic Table of the Elements, preferably B or Al, preferably B; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, preferably a fluorinated aryl group, such fluoro-phenyl or fluoro-naphthyl, more preferably perfluorophenyl or perfluoronaphthyl.

This invention relates to activator compounds represented by Formula (AI):

$$[R^1R^2R^3EH]_d^+[M^{k+}Q_n]^{d-} \quad (AI)$$

wherein:

E is nitrogen or phosphorous;

d is 1, 2 or 3; k is 1, 2, or 3; n is 1, 2, 3, 4, 5, or 6; n−k=d (preferably 1, 2, 3, or 4); n−k=d (preferably d is 1, 2 or 3; k is 3;

n is 4, 5, or 6, preferably when M is B, n is 4);

$R^1$ is a $C_1$-$C_{20}$ alkyl group (preferably a $C_1$-$C_{10}$ alkyl group, preferably $C_1$ to $C_2$ alkyl, preferably methyl), wherein $R^1$ is optionally substituted;

each of $R^2$ and $R^3$ is independently an optionally substituted $C_1$-$C_{40}$ branched or linear alkyl group or mata and/or para-substituted phenyl group, where the meta and para substituents are, independently, an optionally substituted $C_1$ to $C_{40}$ hydrocarbyl group, an optionally substituted alkoxy group, an optionally substituted silyl group, a halogen, or a halogen containing group, wherein $R^1$, $R^2$, and $R^3$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms) and at least one of $R^1$, $R^2$, and $R^3$ is a branched alkyl (such as a $C_3$-$C_{40}$ branched alkyl, alternately $C_7$-$C_{40}$ branched alkyl);

M is an element selected from group 13 of the Periodic Table of the Elements, preferably B or Al, preferably B; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, preferably a fluorinated aryl group, such fluoro-phenyl or fluoro-naphthyl, more preferably perfluorophenyl or perfluoronaphthyl.

This invention also relates to activator compounds represented by Formula (AI):

$$[R^1R^2R^3EH]_d^+[M^{k+}Q_n]^{d-} \quad (AI)$$

wherein:

E is nitrogen or phosphorous;

d is 1, 2 or 3; k is 1, 2, or 3; n is 1, 2, 3, 4, 5, or 6; n−k=d (preferably 1, 2, 3, or 4); n−k=d (preferably d is 1, 2 or 3; k is 3; n is 4, 5, or 6, preferably when M is B, n is 4);

$R^1$ is methyl;

each of $R^2$ and $R^3$ is independently $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl;

wherein $R^1$, $R^2$, and $R^3$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms), and provided that at least one of $R^1$, $R^2$, and $R^3$ is a branched alkyl (such as a $C_3$-$C_{40}$ branched alkyl, such as a $C_7$ to $C_{40}$ branched alkyl);

M is an element selected from group 13 of the Periodic Table of the Elements, preferably B or Al, preferably B; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, preferably a fluorinated aryl group, such fluoro-phenyl or fluoro-naphthyl, more preferably perfluorophenyl or perfluoronaphthyl.

This invention also relates to activator compounds represented by Formula (I):

wherein:

E is nitrogen or phosphorous;

each of $R^1$, $R^2$, and $R^3$ is independently $C_1$-$C_{40}$ linear or branched alkyl or $C_5$-$C_{50}$-aryl (such as $C_5$ to $C_{22}$), wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms (such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms) provided that at least one of $R^1$, $R^2$, and $R^3$ is a $C_3$-$C_{40}$ branched alkyl (such as a $C_7$ to $C_{40}$ branched alkyl); and each of $R^4$, $R^5$, $R^6$, and $R^7$ is phenyl or naphthyl, wherein at least one of $R^4$, $R^5$, $R^6$, and $R^7$ is substituted with from one to seven fluorine atoms.

This invention further relates to activator compounds represented by Formula (AI):

wherein:

E is nitrogen or phosphorous, preferably nitrogen;

d is 1, 2 or 3; k is 1, 2, or 3;

n is 1, 2, 3, 4, 5, or 6 (preferably 1, 2, 3, or 4); n−k=d (preferably d is 1, 2 or 3; k is 3;

n is 4, 5, or 6, preferably when M is B, n is 4);

each of $R^1$, $R^2$, and $R^3$ is independently $C_1$-$C_{40}$ linear or branched alkyl, $C_5$-$C_{50}$-aryl (such as $C_5$ to $C_{22}$), wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms, provided that at least one of $R^1$, $R^2$, and $R^3$ is a branched alkyl (such as a $C_3$-$C_{40}$ branched alkyl), preferably at least two of $R^1$, $R^2$, and $R^3$ are a branched alkyl (such as a $C_3$-$C_{40}$ branched alkyl), preferably each of $R^1$, $R^2$, and $R^3$ is a branched alkyl (such as a $C_3$-$C_{40}$ branched alkyl);

M is an element selected from group 13 of the Periodic Table of the Elements, preferably boron or aluminum; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical. Preferably, each Q is a fluorinated hydrocarbyl group having 1 to 30 carbon atoms, more preferably each Q is a fluorinated aryl (such as phenyl or naphthyl) group, and most preferably each Q is a perflourinated aryl (such as phenyl or naphthyl) group. Examples of suitable $[M^{k+}Q_1]^{d-}$ also include diboron compounds as disclosed in U.S. Pat. No. 5,447,895, which is fully incorporated herein by reference.

In at least one embodiment of the invention, the activator is represented by Formula (I):

wherein:

E is nitrogen or phosphorous, preferably nitrogen;

each of $R^1$, $R^2$, and $R^3$ is independently $C_1$-$C_{40}$ linear or branched alkyl, $C_5$-$C_{22}$-aryl, arylalkyl where the alkyl has from 1 to 30 carbon atoms and the aryl has from 6 to 20 carbon atoms, or five-, six- or seven-membered heterocyclyl comprising at least one atom selected from N, P, O and S, wherein each of $R^1$ $R^2$, and $R^3$ is optionally substituted by halogen, wherein $R^2$ optionally bonds with $R^5$ to independently form a five-, six- or seven-membered ring, preferably wherein, $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms, provided that at least one of $R^1$, $R^2$, and $R^3$ is a branched alkyl (such as a $C_7$-$C_{40}$ branched alkyl), alternately at least two of $R^1$, $R^2$, and $R^3$ are a branched alkyl (such as a $C_7$-$C_{40}$ branched alkyl), alternately all three of $R^1$, $R^2$, and $R^3$ are a branched alkyl (such as a $C_7$-$C_{40}$ branched alkyl); each of $R^4$, $R^5$, $R^6$, and $R^7$ is independently is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, preferably, each of $R^4$, $R^5$, $R^6$, and $R^7$ is independently is a fluorinated hydrocarbyl group having 1 to 30 carbon atoms, more preferably each Q is a fluorinated aryl (such as phenyl or naphthyl) group (substituted with from one to seven fluorine atoms), and most preferably each Q is a perflourinated aryl (such as phenyl or naphthyl) group.

In at least one embodiment of the invention, an activator is an ionic ammonium or phosphonium borate represented by Formula (I):

wherein:

E is nitrogen or phosphorous;

$R^1$ is a $C_1$-$C_{40}$ linear alkyl, preferably methyl;

each of $R^2$, and $R^3$ is independently $C_1$-$C_{40}$ linear or branched alkyl, $C_5$-$C_{22}$-aryl, $C_5$ to $C_{50}$ arylalkyl where the alkyl has from 1 to 30 carbon atoms and the aryl has from 6 to 20 carbon atoms, or five-, six- or seven-membered heterocyclyl comprising at least one atom selected from N, P, O and S, wherein each of $R^1$ $R^2$, and $R^3$ is optionally substituted by halogen, wherein $R^2$ optionally bonds with $R^5$ to independently form a five-, six- or seven-membered ring, preferably wherein, $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms, provided that at least one of $R^2$, and $R^3$ is a $C_3$-$C_{40}$ branched alkyl, alternately both of $R^2$, and $R^3$ are a $C_3$-$C_{40}$ branched alkyl, alternately each of $R^1$, $R^2$, and $R^3$ is a $C_3$-$C_{40}$ branched alkyl; and each of $R^4$, $R^5$, $R^6$, and $R^7$ is independently each a fluorinated hydrocarbyl group having 1 to 30 carbon atoms, more preferably each of $R^4$, $R^5$, $R^6$, and $R^7$ is independently is a fluorinated aryl (such as phenyl or naphthyl) group, and most preferably each of $R^4$, $R^5$, $R^6$, and $R^7$ is independently is a perflourinated aryl (such as phenyl or naphthyl) group, wherein at least one of $R^4$, $R^5$, $R^6$, and $R^7$ is substituted with from one to seven fluorine atoms.

This invention also relates to activator compounds represented by Formula (I):

$$[R^1R^2R^3EH]^+[BR^4R^5R^6R^7]^- \quad (I)$$

wherein:

E is nitrogen or phosphorous, preferably nitrogen;

each of $R^1$, $R^2$, and $R^3$ is independently $C_1$-$C_{40}$ linear or branched alkyl, $C_5$-$C_{50}$-aryl, wherein each of $R^1$, $R^2$, and $R^3$ is independently unsubstituted or substituted with at least one of halide, $C_1$-$C_{50}$ alkyl, $C_5$-$C_{50}$ aryl, $C_6$-$C_{35}$ arylalkyl, or $C_6$-$C_{35}$ alkylaryl, wherein $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 40 or more carbon atoms, provided that at least one of $R^1$, $R^2$, and $R^3$ is a $C_3$-$C_{40}$ branched alkyl, alternately at least two of $R^1$, $R^2$, and $R^3$ are a $C_3$-$C_{40}$ branched alkyl; and each of $R^4$, $R^5$, $R^6$, and $R^7$ is naphthyl, wherein at least one of $R^4$, $R^5$, $R^6$, and $R^7$ is substituted with from one to seven fluorine atoms, preferably seven fluorine atoms.

In a preferred aspect, the activator is an ionic ammonium borate represented by Formula (I):

$$[R^1R^2R^3EH]^+[BR^4R^5R^6R^7]^- \quad (I)$$

wherein:

E is nitrogen or phosphorous;

$R^1$ is a methyl group;

$R^2$ is $C_6$-$C_{50}$ aryl which is optionally substituted with at least one of halide, $C_1$-$C_{35}$ alkyl, $C_5$-$C_{15}$ aryl, $C_6$-$C_{35}$ arylalkyl, and $C_6$-$C_{35}$ alkylaryl;

$R^3$ is $C_1$-$C_{40}$ branched alkyl which is optionally substituted with at least one of halide, $C_1$-$C_{35}$ alkyl, $C_5$-$C_{15}$ aryl, $C_6$-$C_{35}$ arylalkyl, and $C_6$-$C_{35}$ alkylaryl, wherein $R^2$ optionally bonds with $R^3$ to independently form a five-, six- or seven-membered ring, and $R^2$ and $R^3$ together comprise 20 or more carbon atoms, such as 21 or more carbon atoms, such as 22 or more carbon atoms, such as 25 or more carbon atoms, such as 30 or more carbon atoms, such as 35 or more carbon atoms, such as 40 or more carbon atoms, and each of $R^4$, $R^5$, $R^6$, and $R^7$ is independently each a fluorinated hydrocarbyl group having 1 to 30 carbon atoms, wherein at least one of $R^4$, $R^5$, $R^6$, and $R^7$ is substituted with from one to seven fluorine atoms, more preferably each of $R^4$, $R^5$, $R^6$, and $R^7$ is independently is a fluorinated aryl (such as phenyl or naphthyl) group, and most preferably each of $R^4$, $R^5$, $R^6$, and $R^7$ is independently is a perflourinated aryl (such as phenyl or naphthyl) group.

Catalyst systems of the present disclosure may be formed by combining the catalysts with activators in any suitable manner, including by supporting them for use in slurry or gas phase polymerization. The catalyst systems may also be added to or generated in solution polymerization or bulk polymerization (in the monomer, i.e., little or no solvent).

Both the cation part of formulas (AI) and (I) as well as the anion part thereof, which is an NCA, will be further illustrated below. Any combinations of cations and NCAs disclosed herein are suitable to be used in the processes of the present disclosure and are thus incorporated herein.

Activators—The Cations

The cation component of the activators described herein (such as those of formulas (AI) and (I) above), is a protonated Lewis base that can be capable of protonating a moiety, such as an alkyl or aryl, from the transition metal compound. Thus, upon release of a neutral leaving group (e.g. an alkane resulting from the combination of a proton donated from the cationic component of the activator and an alkyl substituent of the transition metal compound) transition metal cation results, which is the catalytically active species.

In any embodiment of formula (I) or (AI), where the cation is $[R^1R^2R^3EH]^+$, E is nitrogen or phosphorous, preferably nitrogen; each of $R^1$, $R^2$, and $R^3$ is independently hydrogen, $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 37 or more carbon atoms, such as 40 or more carbon atoms, such as 45 or more carbon atoms, and provided that at least one (alternately one, two or three) of $R^1$, $R^2$, and $R^3$ is a branched alkyl, (such as a $C_3$-$C_{40}$ branched alkyl, alternately such as a $C_7$ to $C_{40}$ branched alkyl).

In at least one embodiment of formula (I) or (AI), where the cation is $[R^1R^2R^3EH]^+$, E is nitrogen or phosphorous, and each of $R^1$, $R^2$, and $R^3$ is independently $C_1$-$C_{40}$ linear or branched alkyl, $C_5$-$C_{50}$-aryl (such as $C_5$-$C_{22}$-aryl, preferably an arylalkyl (where the alkyl has from 1 to 10 carbon atoms and the aryl has from 6 to 20 carbon atoms), or five-, six- or seven-membered heterocyclyl comprising at least one atom selected from N, P, O and S, wherein each of $R^1$ $R^2$, and $R^3$ is optionally substituted by halogen, —NR'$_2$, —OR' or —SiR'$_3$ (where R' is independently hydrogen or $C_1$-$C_{20}$ hydrocarbyl), wherein $R^2$ optionally bonds with $R^5$ to independently form a five-, six- or seven-membered ring. $R^1$, $R^2$, and $R^3$ together comprise 15 or more carbon atoms, such as 18 or more carbon atoms, such as 20 or more carbon atoms, such as 22 or more carbon atoms, such as 25 or more carbon atoms, such as 30 or more carbon atoms, such as 35 or more carbon atoms, such as 37 or more carbon atoms, such as 40 or more carbon atoms, such as 45 or more carbon atoms, provided that at least one of $R^1$, $R^2$, and $R^3$ is a $C_3$-$C_{40}$ branched alkyl, alternately at least two of $R^1$, $R^2$, and $R^3$ are a $C_3$-$C_{40}$ branched alkyl.

In any embodiment of formula (I) or (AI) described herein one, two or three of $R^1$, $R^2$ and $R^3$ may independently be represented by the formula (AIII):

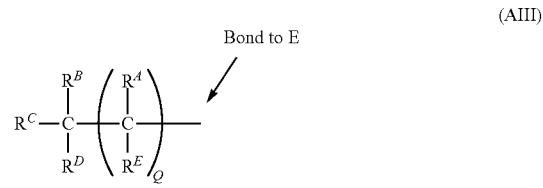

wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$—C—$R^E$) group, one or both of $R^A$ and $R^E$ is not H; and $R^C$, $R^B$ and $R^D$ are hydrogen; and Q is an integer from 5 to 40.

In any embodiment of formula (I) or (AI) herein, one, two or three of $R^1$, $R^2$ and $R^3$ may independently be represented by the formula (IV) where:

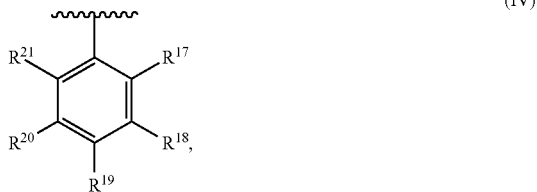

wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$—C—$R^E$) group, one or both of $R^A$ and $R^E$ is not H;

$R^C$, $R^B$ and $R^D$ are hydrogen; and

Q is an integer from 5 to 40, each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, a heteroatom-containing group, or is represented by formula (BIII), provided that at least one of $R^{17}$, $R^{18}$, $R^{19}$, $R^{20}$, and $R^{21}$ is not hydrogen).

In any embodiment of formula (I) or (AI) one, two or three of $R^1$, $R^2$ and $R^3$ may independently be represented by the formula (AIII) or (IV):

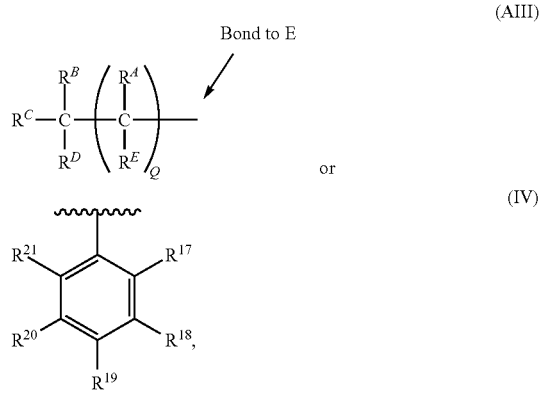

wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$—C—$R^E$) group, one or both of $R^A$ and $R^E$ is not H;

$R^C$, $R^B$ and $R^D$ are hydrogen; and

Q is an integer from 5 to 40, each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, a heteroatom-containing group, or is represented by formula (III) (provided that at least one of $R^{17}$, $R^{18}$, $R^{19}$, $R^{20}$, and $R^{21}$ is a branched alkyl, preferably one, two, three, four, five of $R^{17}$, $R^{18}$, $R^{19}$, $R^{20}$, and $R^{21}$ are represented by formula (III)).

In any embodiment described herein the branched alkyl may have 1 to 30 tertiary or quaternary carbons, alternately 2 to 10 tertiary or quaternary carbons, alternately 2 to 4 tertiary or quaternary carbons, alternately the branched alkyl has 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 tertiary or quaternary carbons.

In any embodiment of formula (I) or (AI), each of $R^1$, $R^2$ and $R^3$ may independently be selected from:

1) optionally substituted linear alkyls (such as methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl, n-pentacosyl, n-hexacosyl, n-heptacosyl, n-octacosyl, n-nonacosyl, or n-tricontyl);

2) optionally substituted branched alkyls (such as alkyl-butyl, alkyl-pentyl, alkyl-hexyl, alkyl-heptyl, alkyl-octyl, alkyl-nonyl, alkyl-decyl, alkyl-undecyl, alkyl-dodecyl, alkyl-tridecyl, alkyl-butadecyl, alkyl-pentadecyl, alkyl-hexadecyl, alkyl-heptadecyl, alkyl-octadecyl, alkyl-nonadecyl, alkyl-icosyl (including multi-alkyl analogs, i.e, dialkyl-butyl, dialkyl-pentyl, dialkyl-hexyl, dialkyl-heptyl, dialkyl-octyl, dialkyl-nonyl, dialkyl-decyl, dialkyl-undecyl, dialkyl-dodecyl, dialkyl-tridecyl, dialkyl-butadecyl, dialkyl-pentadecyl, dialkyl-hexadecyl, dialkyl-heptadecyl, dialkyl-octadecyl, dialkyl-nonadecyl, dialkyl-icosyl, trialkyl-butyl, trialkyl-pentyl, trialkyl-hexyl, trialkyl-heptyl, trialkyl-octyl, trialkyl-nonyl, trialkyl-decyl, trialkyl-undecyl, trialkyl-dodecyl, trialkyl-tridecyl, trialkyl-butadecyl, trialkyl-pentadecyl, trialkyl-hexadecyl, trialkyl-heptadecyl, trialkyl-octadecyl, trialkyl-nonadecyl, and trialkyl-icosyl, etc.), and isomers thereof wherein each alkyl group is independently a $C_1$ to $C_{40}$, (alternately $C_2$ to $C_{30}$, alternately $C_3$ to $C_{20}$) linear, branched or cyclic alkyl group), preferably the alkyl group is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, or tricontyl);

3) optionally substituted arylalkyls, such as (methylphenyl, ethylphenyl, propylphenyl, butylphenyl, pentylphenyl, hexylphenyl, heptylphenyl, octylphenyl, nonylphenyl, decylphenyl, undecylphenyl, dodecylphenyl, tridecylphenyl, tetradecylphenyl, pentadecylphenyl, hexadecylphenyl, heptadecylphenyl, octadecylphenyl, nonadecylphenyl, icosylphenyl, henicosylphenyl, docosylphenyl, tricosylphenyl, tetracosylphenyl, pentacosylphenyl, hexacosylphenyl, heptacosylphenyl, octacosylphenyl, nonacosylphenyl, tricontylphenyl, 3,5,5-trimethylhexylphenyl, dioctylphenyl, 3,3,5-trimethylhexylphenyl, 2,2,3,3,4 pentamethypentylylphenyl, and the like);

4) optionally substituted silyl groups, such as a trialkylsilyl group, where each alkyl is independently an optionally substituted $C_1$ to $C_{20}$ alkyl (such as trimethylsilyl, triethylsilyl, tripropylsilyl, tributylsilyl, trihexylsilyl, triheptylsilyl, trioctylsilyl, trinonylsilyl, tridecylsilyl, triundecylsilyl, tridodecylsilyl, tri-tridecylsilyl, tri-tetradecylsilyl, tri-pentadecylsilyl, tri-hexadecylsilyl, tri-heptadecylsilyl, tri-octadecylsilyl, tri-nonadecylsilyl, tri-icosylsilyl);

5) optionally substituted alkoxy groups (such as —OR*, where R* is an optionally substituted $C_1$ to $C_{20}$ alkyl or aryl (such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, phenyl, alkylphenyl (such as methyl phenyl, propyl phenyl, etc.), naphthyl, or anthracenyl);

6) halogens (such as Br or Cl); and 7) halogen containing groups (such as bromomethyl, bromophenyl, and the like), provided that at least one of $R^1$, $R^2$ and $R^3$ contains a branched alkyl group.

In any embodiment of formula (I) or (AI), $R^1$ is methyl.

In any embodiment of formula (I) or (AI), $R^2$ is unsubstituted phenyl or substituted phenyl. In at least one embodiment, $R^2$ is phenyl, methyl phenyl, n-butyl phenyl, n-octadecyl-phenyl, or an isomer thereof, preferably $R^2$ is meta or para substituted phenyl, such as meta- or para-substituted alkyl substituted phenyl.

In any embodiment of formula (I) or (AI), $R^3$ is branched alkyl such as isopropyl, isobutyl, isopentyl, isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, isohenicosyl, isodocosyl, isotricosyl, isotetracosyl, isopentacosyl, isohexacosyl, isoheptacosyl, isooctacosyl, isononacosyl, or isotricontyl, alkyl-butyl, alkyl-pentyl, alkyl-hexyl, alkyl-heptyl, alkyl-octyl, alkyl-nonyl, alkyl-decyl, alkyl-undecyl, alkyl-dodecyl, alkyl-tridecyl, alkyl-butadecyl, alkyl-pentadecyl, alkyl-hexadecyl, alkyl-heptadecyl, alkyl-octadecyl, alkyl-nonadecyl, alkyl-icosyl (including multi-alkyl analogs, i.e, dialkyl-butyl, dialkyl-pentyl, dialkyl-hexyl, dialkyl-heptyl, dialkyl-octyl, dialkyl-nonyl, dialkyl-decyl, dialkyl-undecyl, dialkyl-dodecyl, dialkyl-tridecyl, dialkyl-butadecyl, dialkyl-pentadecyl, dialkyl-hexadecyl, dialkyl-heptadecyl, dialkyl-octadecyl, dialkyl-nonadecyl, dialkyl-icosyl, trialkyl-butyl, trialkyl-pentyl, trialkyl-hexyl, trialkyl-heptyl, trialkyl-octyl, trialkyl-nonyl, trialkyl-decyl, trialkyl-undecyl, trialkyl-dodecyl, trialkyl-tridecyl, trialkyl-butadecyl, trialkyl-pentadecyl, trialkyl-hexadecyl, trialkyl-heptadecyl, trialkyl-octadecyl, trialkyl-nonadecyl, and trialkyl-icosyl), and isomers thereof wherein each alkyl group is independently a $C_1$ to $C_{40}$, (alternately $C_2$ to $C_{30}$, alternately $C_3$ to $C_{20}$) linear, branched or cyclic alkyl group, preferably the alkyl group is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, or tricontyl).

In any embodiment of formula (I) or (AI), $R^1$ is methyl, and $R^2$ is phenyl, methyl phenyl, n-butyl phenyl, n-octadecyl-phenyl, or an isomer thereof, preferably $R^2$ is meta or para substituted phenyl, such as meta- or para-substituted alkyl substituted phenyl, and $R^3$ is branched alkyl.

In any embodiment of formula (I) or (AI), $R^1$ is methyl, and $R^2$ is branched alkyl, and $R^3$ is branched alkyl.

In a preferred embodiment, $R^1$ is methyl, $R^2$ is substituted phenyl, $R^3$ is $C_{10}$ to $C_{30}$ branched alkyl.

Preferably $R^2$ is not meta substituted phenyl. Preferably $R^2$ is not ortho substituted phenyl.

In a preferred embodiment, $R^1$ is methyl, $R^2$ is $C_1$ to $C_{35}$ alkyl substituted phenyl (preferably ortho- or meta-substituted), $R^3$ is $C_8$ to $C_{30}$ branched alkyl.

In a preferred embodiment, $R^1$ is $C_1$ to $C_{10}$ alkyl, $R^2$ is $C_1$ to $C_{35}$ alkyl substituted phenyl (preferably para substituted phenyl), $R^3$ is $C_8$ to $C_{30}$ branched alkyl.

In a preferred embodiment, $R^1$ is methyl; $R^2$ is $C_1$ to $C_{35}$ alkyl substituted phenyl, such as methylphenyl, ethylphenyl, n-propylphenyl, n-butylphenyl, n-pentylphenyl, n-hexylphenyl, n-heptylphenyl, n-octylphenyl, n-nonylphenyl, n-decylphenyl, n-undecyl, phenyl n-dodecylphenyl, n-tridecylphenyl, n-butadecylphenyl, n-pentadecylphenyl, n-hexadecylphenyl, n-heptadecylphenyl, n-octadecylphenyl, n-nonadecylphenyl, and n-icosylphenyl, n-henicosylphenyl, n-docosylphenyl, n-tricosylphenyl, n-tetracosylphenyl, n-pentacosylphenyl, n-hexacosylphenyl, n-heptacosylphenyl, n-octacosylphenyl, n-nonacosylphenyl, n-triacontylphenyl; and $R^3$ is $C_8$ to $C_{30}$ branched alkyl, such as i-propyl, alkyl-butyl, alkyl-pentyl, alkyl-hexyl, alkyl-heptyl, alkyl-octyl, alkyl-nonyl, alkyl-decyl, alkyl-undecyl, alkyl-dodecyl, alkyl-tridecyl, alkyl-butadecyl, alkyl-pentadecyl, alkyl-hexadecyl, alkyl-heptadecyl, alkyl-octadecyl, alkyl-nonadecyl, and alkyl-icosyl (such as 2-alkyl-pentyl, 2-alkyl-hexyl, 2-alkyl-heptyl, 2-alkyl-octyl, 2-alkyl-nonyl, 2-alkyl-decyl, 2-alkyl-undecyl, 2-alkyl-dodecyl, 2-alkyl-tridecyl, 2-alkyl-butadecyl, 2-alkyl-pentadecyl, 2-alkyl-hexadecyl, 2-alkyl-heptadecyl, 2-alkyl-octadecyl, 2-alkyl-nonadecyl, 2-alkyl-icosyl or a multi-alkyl analogs, i.e, dialkyl-butyl, dialkyl-pentyl, dialkyl-hexyl, dialkyl-heptyl, dialkyl-octyl, dialkyl-nonyl, dialkyl-decyl, dialkyl-undecyl, dialkyl-dodecyl, dialkyl-tridecyl, dialkyl-butadecyl, dialkyl-pentadecyl, dialkyl-hexadecyl, dialkyl-heptadecyl, dialkyl-octadecyl, dialkyl-nonadecyl, dialkyl-icosyl, trialkyl-butyl, trialkyl-pentyl, trialkyl-hexyl, trialkyl-heptyl, trialkyl-octyl, trialkyl-nonyl, trialkyl-decyl, trialkyl-undecyl, trialkyl-dodecyl, trialkyl-tridecyl, trialkyl-butadecyl, trialkyl-pentadecyl, trialkyl-hexadecyl, trialkyl-heptadecyl, trialkyl-octadecyl, trialkyl-nonadecyl, and trialkyl-icosyl, etc.), or an isomer thereof wherein each alkyl group is independently a $C_1$ to $C_{40}$, (alternately $C_2$ to $C_{30}$, alternately $C_3$ to $C_{20}$) linear, branched or cyclic alkyl group), preferably the alkyl group is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, or tricontyl).

In any embodiment herein, $R^2$ is $C_1$ to $C_{35}$ alkyl substituted phenyl, such as methylphenyl, ethylphenyl, n-propylphenyl, n-butylphenyl, n-pentylphenyl, n-hexylphenyl, n-heptylphenyl, n-octylphenyl, n-nonylphenyl, n-decylphenyl, n-undecyl, phenyl n-dodecylphenyl, n-tridecylphenyl, n-butadecylphenyl, n-pentadecylphenyl, n-hexadecylphenyl, n-heptadecylphenyl, n-octadecylphenyl, n-nonadecylphenyl, and n-icosylphenyl, n-henicosylphenyl, n-docosylphenyl, n-tricosylphenyl, n-tetracosylphenyl, n-pentacosylphenyl, n-hexacosylphenyl, n-heptacosylphenyl, n-octacosylphenyl, n-nonacosylphenyl, n-triacontylphenyl; and $R^3$ is $C_8$ to $C_{30}$ branched alkyl, such as i-propyl, alkyl-butyl, alkyl-pentyl, alkyl-hexyl, alkyl-heptyl, alkyl-octyl, alkyl-nonyl, alkyl-decyl, alkyl-undecyl, alkyl-dodecyl, alkyl-tridecyl, alkyl-butadecyl, alkyl-pentadecyl, alkyl-hexadecyl, alkyl-heptadecyl, alkyl-octadecyl, alkyl-nonadecyl, and alkyl-icosyl (such as 2-alkyl-pentyl, 2-alkyl-hexyl, 2-alkyl-heptyl, 2-alkyl-octyl, 2-alkyl-nonyl, 2-alkyl-decyl, 2-alkyl-undecyl, 2-alkyl-dodecyl, 2-alkyl-tridecyl, 2-alkyl-butadecyl, 2-alkyl-pentadecyl, 2-alkyl-hexadecyl, 2-alkyl-heptadecyl, 2-alkyl-octadecyl, 2-alkyl-nonadecyl, 2-alkyl-icosyl or a multi-alkyl analog, i.e, dialkyl-butyl, dialkyl-pentyl, dialkyl-hexyl, dialkyl-heptyl, dialkyl-octyl, dialkyl-nonyl, dialkyl-decyl, dialkyl-undecyl, dialkyl-dodecyl, dialkyl-tridecyl, dialkyl-butadecyl, dialkyl-pentadecyl, dialkyl-hexadecyl, dialkyl-heptadecyl, dialkyl-octadecyl, dialkyl-nonadecyl, dialkyl-icosyl, trialkyl-butyl, trialkyl-pentyl, trialkyl-hexyl, trialkyl-heptyl, trialkyl-octyl, trialkyl-nonyl, trialkyl-decyl, trialkyl-undecyl, trialkyl-dodecyl, trialkyl-tridecyl, trialkyl-butadecyl, trialkyl-pentadecyl, trialkyl-hexadecyl, trialkyl-heptadecyl, trialkyl-octadecyl, trialkyl-nonadecyl, and trialkyl-icosyl, etc.), or an isomer thereof wherein each alkyl group is independently a $C_1$ to $C_{40}$, (alternately $C_2$ to $C_{30}$, alternately $C_3$ to $C_{20}$) linear, branched or cyclic alkyl group), preferably the alkyl group is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, or tricontyl).

In a preferred embodiment of formula (I), $R^1$ is methyl, $R^2$ is substituted phenyl, $R^3$ is $C_5$ to $C_{30}$ branched alkyl, and $R^4$, $R^5$, $R^6$, $R^7$ are perfluoronaphthyl.

In a preferred embodiment of formula (AI), $R^1$ is methyl, $R^2$ is substituted phenyl, $R^3$ is $C_5$ to $C_{30}$ branched alkyl, E is nitrogen, and each Q is perfluoronaphthyl.

In a preferred embodiment, $R^1$ is methyl; $R^2$ is $C_1$ to $C_{35}$ alkyl substituted phenyl, such as methylphenyl, ethylphenyl, n-propylphenyl, n-butylphenyl, n-pentylphenyl, n-hexylphenyl, n-heptylphenyl, n-octylphenyl, n-nonylphenyl, n-decylphenyl, n-undecyl, phenyl n-dodecylphenyl, n-tridecylphenyl, n-butadecylphenyl, n-pentadecylphenyl, n-hexadecylphenyl, n-heptadecylphenyl, n-octadecylphenyl, n-nonadecylphenyl, and n-icosylphenyl, n-henicosylphenyl, n-docosylphenyl, n-tricosylphenyl, n-tetracosylphenyl, n-pentacosylphenyl, n-hexacosylphenyl, n-heptacosylphenyl, n-octacosylphenyl, n-nonacosylphenyl, n-triacontylphenyl; $R^3$ is branched alkyl (such as $C_{10}$ to $C_{30}$ branched alkyl) or alternately is i-propyl, alkyl-butyl, alkyl-pentyl, alkyl-hexyl, alkyl-heptyl, alkyl-octyl, alkyl-nonyl, alkyl-decyl, alkyl-undecyl, alkyl-dodecyl, alkyl-tridecyl, alkyl-butadecyl, alkyl-pentadecyl, alkyl-hexadecyl, alkyl-heptadecyl, alkyl-octadecyl, alkyl-nonadecyl, and alkyl-icosyl (such as 2-alkyl-pentyl, 2-alkyl-hexyl, 2-alkyl-heptyl, 2-alkyl-octyl, 2-alkyl-nonyl, 2-alkyl-decyl, 2-alkyl-undecyl, 2-alkyl-dodecyl, 2-alkyl-tridecyl, 2-alkyl-butadecyl, 2-alkyl-pentadecyl, 2-alkyl-hexadecyl, 2-alkyl-heptadecyl, 2-alkyl-octadecyl, 2-alkyl-nonadecyl, and 2-alkyl-icosyl or a multi-alkyl analog, i.e, dialkyl-butyl, dialkyl-pentyl, dialkyl-hexyl, dialkyl-heptyl, dialkyl-octyl, dialkyl-nonyl, dialkyl-decyl, dialkyl-undecyl, dialkyl-dodecyl, dialkyl-tridecyl, dialkyl-butadecyl, dialkyl-pentadecyl, dialkyl-hexadecyl, dialkyl-heptadecyl, dialkyl-octadecyl, dialkyl-nonadecyl, dialkyl-icosyl, trialkyl-butyl, trialkyl-pentyl, trialkyl-hexyl, trialkyl-heptyl, trialkyl-octyl, trialkyl-nonyl, trialkyl-decyl, trialkyl-undecyl, trialkyl-dodecyl, trialkyl-tridecyl, trialkyl-butadecyl, trialkyl-pentadecyl, trialkyl-hexadecyl, trialkyl-heptadecyl, trialkyl-octadecyl, trialkyl-nonadecyl, trialkyl-icosyl, etc.), or an isomer thereof wherein each alkyl group is independently a $C_1$ to $C_{40}$, (alternately $C_2$ to $C_{30}$, alternately $C_3$ to $C_{20}$) linear, branched or cyclic alkyl group), preferably the alkyl group is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl, or tricontyl); and each Q is or each of $R^4$, $R^5$, $R^6$, $R^7$ are perfluoronaphthyl.

In any embodiment herein the branched alkyl can be isopropyl, isobutyl, isopentyl, isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl, isononadecyl, isoicosyl, isohenicosyl, isodocosyl, isotricosyl, isotetracosyl, isopentacosyl, isohexacosyl, isoheptacosyl, isooctacosyl, isononacosyl, or isotricontyl.

In a preferred embodiment of the invention, $R^1$ is o-MePh, $R^2$ and $R^3$ are isooctadecyl.

In a preferred embodiment of the invention, $R^1$, $R^2$ and $R^3$ together comprise 20 or more carbon atoms, such as 21 or more carbon atoms, such as 22 or more carbon atoms, such as 25 or more carbon atoms, such as 30 or more carbon atoms, such as 35 or more carbon atoms, such as 37 or more carbon atoms, such as 40 or more carbon atoms, such as 45 or more carbon atoms.

Activators—The Anion

The anion component of the activators described herein includes those represented by the formula $[M^{k+}Q_n]$ wherein k is 1, 2, or 3; n is 1, 2, 3, 4, 5, or 6 (preferably 1, 2, 3, or 4); M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halo-substituted-hydrocarbyl radicals, said Q having up to 20 carbon atoms with the proviso that in not more than 1 occurrence is Q a halide. Preferably, each Q is a fluorinated hydrocarbyl group, optionally having 1 to 20 carbon atoms, more preferably each Q is a fluorinated aryl group, and most preferably each Q is a perfluorinated aryl group. Preferably at least one Q is not substituted phenyl, such as perfluorophenyl, preferably all Q are not substituted phenyl, such as perfluorophenyl.

Alternately, in any embodiment described herein, at least one Q is not substituted phenyl, alternately all Q are not substituted phenyl. Alternately, at least one Q is not fluoro-substituted phenyl, alternately all Q are not fluoro-substituted phenyl. Alternately, at least one Q is not perfluorophenyl, alternately, all Q are not perfluorophenyl.

In a preferred embodiment of any embodiment of Formula (AI), when $R^1$ is methyl, $R^2$ is C18 and $R^3$ is C18, then each Q is not perfluorophenyl.

In at least one embodiment, for the borate moiety ($[BR^4R^5R^6R^7]^-$) of the activator represented by formula (I), each of $R^4$, $R^5$, $R^6$, and $R^7$ is independently aryl (such as naphthyl), wherein at least one of $R^4$, $R^5$, $R^6$, and $R^7$ is substituted with from one to seven fluorine atoms. In at least one embodiment, each of $R^4$, $R^5$, $R^6$, and $R^7$ is naphthyl, wherein at least one of $R^4$, $R^5$, $R^6$, and $R^7$ is substituted with from one to seven fluorine atoms.

In at least one embodiment, each of $R^4$, $R^5$, $R^6$, and $R^7$ is independently naphthyl comprising one fluorine atom, two fluorine atoms, three fluorine atoms, four fluorine atoms, five fluorine atoms, six fluorine atoms, or seven fluorine atoms.

In a preferred embodiment of any embodiment of Formula (I), when $R^1$ is methyl, $R^2$ is C18 and $R^3$ is C18, then each of $R^4$, $R^5$, $R^6$, and $R^7$ is not perfluorophenyl.

In at least one embodiment, $R^4$ is independently naphthyl comprising one fluorine atom, two fluorine atoms, three fluorine atoms, four fluorine atoms, five fluorine atoms, six fluorine atoms, or seven fluorine atoms, and each of $R^5$, $R^6$, and $R^7$ is independently phenyl comprising one fluorine atom, two fluorine atoms, three fluorine atoms, four fluorine atoms, or five fluorine atoms or naphthyl comprising one fluorine atom, two fluorine atoms, three fluorine atoms, four fluorine atoms, five fluorine atoms, six fluorine atoms, or seven fluorine atoms.

In any embodiment of formula (I) or (AI), each of $R^4$, $R^5$, $R^6$, and $R^7$ is independently naphthyl, wherein at least one of $R^4$, $R^5$, $R^6$, and $R^7$ is naphthyl substituted with one, two, three, four, five, six or seven fluorine atoms.

In any embodiment of formula (I) or (AI), each of $R^4$, $R^5$, $R^6$, and $R^7$ is independently phenyl, wherein at least one of $R^4$, $R^5$, $R^6$, and $R^7$ is phenyl substituted with one, two, three, four, or five fluorine atoms.

Alternately, in any embodiment of formula (I) or (AI), preferably at least one $R^4$, $R^5$, $R^6$, and $R^7$ is not substituted phenyl, preferably all of $R^4$, $R^5$, $R^6$, and $R^7$ are not substituted phenyl. In a preferred embodiment, $R^1$ is not methyl, $R^2$ is not C18 and $R^3$ is not C18.

In any embodiment of formula (I) or (AI), preferably all Q or all of $R^4$, $R^5$, $R^6$, and $R^7$ are not perfluoroaryl, such as perfluorophenyl.

In any embodiment of formula (I) or (AI), all of $R^4$, $R^5$, $R^6$, and $R^7$ are naphthyl, wherein at least one, two, three, or four of $R^4$, $R^5$, $R^6$, and $R^7$ is/are substituted with one, two, three, four, five, six or seven fluorine atoms.

In any embodiment described herein, preferably each of $R^4$, $R^5$, $R^6$, and $R^7$ is independently a naphthyl comprising one fluorine atom, two fluorine atoms, three fluorine atoms, four fluorine atoms, five fluorine atoms, six fluorine atoms, or seven fluorine atoms, preferably seven fluorine atoms.

In at least one embodiment, $R^4$ is independently naphthyl comprising one fluorine atom, two fluorine atoms, three fluorine atoms, four fluorine atoms, five fluorine atoms, six fluorine atoms, or seven fluorine atoms.

In any embodiment described herein, each of $R^4$, $R^5$, $R^6$, and $R^7$ is independently each a fluorinated hydrocarbyl group having 1 to 30 carbon atoms, more preferably each of $R^4$, $R^5$, $R^6$, and $R^7$ is independently is a fluorinated aryl (such as phenyl, biphenyl, [$(C_6H_3(C_6H_5)_2)_4B$], or naphthyl) group, and most preferably each of $R^4$, $R^5$, $R^6$, and $R^7$ is independently is a perflourinated aryl (such as bi-phenyl, [$(C_6H_3(C_6H_5)_2)_4B$], or naphthyl) group, preferably at least one $R^4$, $R^5$, $R^6$, and $R^7$ is not perfluorophenyl.

In one embodiment, the borate activator comprises tetrakis(heptafluoronaphth-2-yl)borate.

Preferred anions for use in the non-coordinating anion activators described herein include those represented by Formula 7 below:

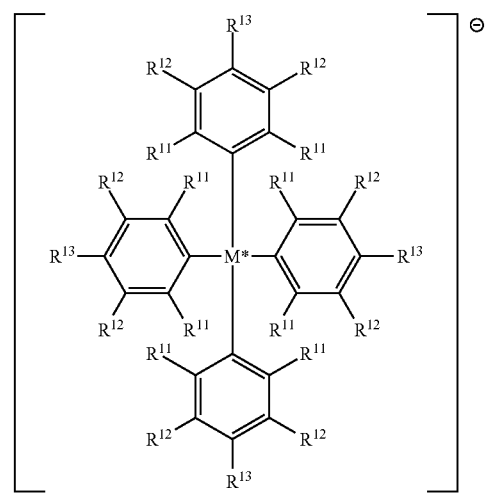

Formula 7 wherein:
M* is a group 13 atom, preferably B or Al, preferably B;
each $R^{11}$ is, independently, a halide, preferably a fluoride;
each $R^{12}$ is, independently, a halide, a $C_6$ to $C_{20}$ substituted aromatic hydrocarbyl group or a siloxy group of the formula —O—Si—$R^a$, where $R^a$ is a $C_1$ to $C_{20}$ hydrocarbyl or hydrocarbylsilyl group, preferably $R^{12}$ is a fluoride or a perfluorinated phenyl group;
each $R^{13}$ is a halide, a $C_6$ to $C_{20}$ substituted aromatic hydrocarbyl group or a siloxy group of the formula —O—Si—$R_a$, where $R^a$ is a $C_1$ to $C_{20}$ hydrocarbyl or hydrocarbylsilyl group, preferably $R^{13}$ is a fluoride or a $C_6$ perfluorinated aromatic hydrocarbyl group;
wherein $R^{12}$ and $R^{13}$ can form one or more saturated or unsaturated, substituted or unsubstituted rings, preferably $R^{12}$ and $R^{13}$ form a perfluorinated phenyl ring. Preferably the anion has a molecular weight of greater than 700 g/mol, and, preferably, at least three of the substituents on the M* atom each have a molecular volume of greater than 180 cubic A.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in Girolami, G. S. (1994) "A Simple "Back of the Envelope" Method for Estimating the Densities and Molecular Volumes of Liquids and Solids," *Journal of Chemical Education*, v. 71(11), November 1994, pp. 962-964. Molecular volume (MV), in units of cubic A, is calculated using the formula: MV=8.3$V_S$, where $V_S$ is the scaled volume. $V_S$ is the sum of the relative volumes of the constituent atoms, and is calculated from the molecular formula of the substituent using Table A below of relative volumes. For fused rings, the $V_S$ is decreased by 7.5% per fused ring. The Calculated Total MV of the anion is the sum of the MV per substituent, for example, the MV of perfluorophenyl is 183 Å$^3$, and the Calculated Total MV for tetrakis(perfluorophenyl)borate is four times 183 Å$^3$, or 732 Å$^3$.

TABLE A

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |

TABLE A-continued

| Element | Relative Volume |
|---|---|
| $2^{nd}$ long period, Rb to I | 7.5 |
| $3^{rd}$ long period, Cs to Bi | 9 |

Exemplary anions useful herein and their respective scaled volumes and molecular volumes are shown in Table 2 below. The dashed bonds indicate bonding to boron.

TABLE 2

| Ion | Structure of Boron Substituents | Molecular Formula of Each Substituent | $V_S$ | MV Per subst. (Å$^3$) | Calculated Total MV (Å$^3$) |
|---|---|---|---|---|---|
| tetrakis(perfluorophenyl)borate | | $C_6F_5$ | 22 | 183 | 732 |
| tris(perfluorophenyl)-(perfluoronaphthyl)borate | | $C_6F_5$<br>$C_{10}F_7$ | 22<br>34 | 183<br>261 | 810 |
| (perfluorophenyl)tris-(perfluoronaphthyl)borate | | $C_6F_5$<br>$C_{10}F_7$ | 22<br>34 | 183<br>261 | 966 |
| tetrakis(perfluoronaphthyl)borate | | $C_{10}F_7$ | 34 | 261 | 1044 |
| tetrakis(perfluorobiphenyl)borate | | $C_{12}F_9$ | 42 | 349 | 1396 |

TABLE 2-continued

| Ion | Structure of Boron Substituents | Molecular Formula of Each Substituent | MV Per subst. $V_S$ (Å³) | Calculated Total MV (Å³) |
|---|---|---|---|---|
| [(C₆F₃(C₆F₅)₂)₄B] | 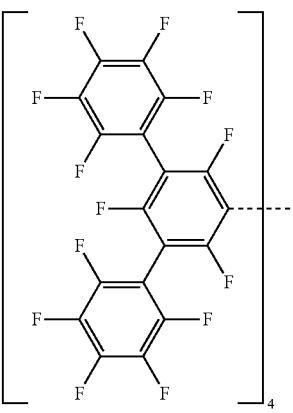 | $C_{18}F_{13}$ | 62 | 515 | 2060 |

The activators may be added to a polymerization in the form of an ion pair using, for example, [DEBAH]+ [NCA]− in which the 4-butyl-N,N-bis(isotridecyl)benzenaminium- ("DEBAH)") cation reacts with a basic leaving group on the transition metal complex to form a transition metal complex cation and [NCA]-. Alternatively, the transition metal complex may be reacted with a neutral NCA precursor, such as B(C₁₀F₇)₃, which abstracts an anionic group from the complex to form an activated species.

In at least one embodiment, the activators obtained in their salt form used for a borate activator compound are: Lithium tetrakis(heptafluoronaphthalen-2-yl)borate etherate (Li—BF28), N,N-Dimethylanilinium tetrakis(heptafluoronaphthalen-2-yl)borate (DMAH-BF28), Sodium tetrakis (heptafluoronaphthalen-2-yl)borate (Na—BF28) and N,N-dimethylanilinium tetrakis(heptafluoronaphthalen-2-yl) borate (DMAH-BF28).

In at least one embodiment, an activator of the present disclosure, when combined with a group 4 metallocene catalyst compound to form an active olefin polymerization catalyst, produces a higher molecular weight polymer (e.g., Mw) than comparative activators that use other borate anions.

In at least one embodiment, an activator of the present disclosure where R¹ is methyl, when combined with a group 4 metallocene to form an active olefin polymerization catalyst, produces a higher molecular weight polymer (e.g., Mw) than comparative activators that use other borate anions.

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1 alternately from 1:1 to 1000:1. A particularly useful range is from 0.5:1 to 10:1, preferably 1:1 to 5:1.

It is also within the scope of the present disclosure that the catalyst compounds can be combined with combinations of alumoxanes and the activators described herein.

Synthesis

In at least one embodiment, the general synthesis of the activators can be performed using a two-step process. In the first step, an amine or phosphine is dissolved in a solvent (e.g. hexane, cyclohexane, methylcyclohexane, ether, dichloromethane, toluene) and an excess (e.g., 1.2 molar equivalents) of hydrogen chloride is added to form a chloride salt. This salt is typically isolated by filtration from the reaction medium and dried under reduced pressure. The isolated chloride is then heated to reflux with about one molar equivalent of an alkali metal metallate or metalloid (such as a borate or aluminate) in a solvent (e.g. cyclohexane, dichloromethane, methylcyclohexane) to form the desired borate or aluminate along with byproduct alkali metal chloride, the latter of which can typically be removed by filtration.

In at least one embodiment, the general synthesis of the ammonium borate activators can be performed using a two-step process. In the first step, an amine is dissolved in a solvent (e.g. hexane, cyclohexane, methylcyclohexane, ether, dichloromethane, toluene) and an excess (e.g., 1.2 molar equivalents) of hydrogen chloride is added to form an ammonium chloride salt. This salt is typically isolated by filtration from the reaction medium and dried under reduced pressure. The isolated ammonium chloride is then heated to reflux with about one molar equivalent of an alkali metal borate in a solvent (e.g. cyclohexane, dichloromethane, methylcyclohexane) to form the ammonium borate along with byproduct alkali metal chloride, the latter of which can typically be removed by filtration.

In at least one embodiment, an activator of the present disclosure is soluble in an aliphatic solvent at a concentration of about 10 mM or greater, such as about 20 mM or greater, such as about 30 mM or greater, such as about 50 mM or greater, such as about 75 mM or greater, such as about 100 mM or greater, such as about 200 mM or greater, such as about 300 mM or greater. In at least one embodiment, an activator of the present disclosure dissolves in isohexane or methylcyclohexane at 25° C. to form a homogeneous solution of at least 10 mM concentration.

In at least one embodiment, the solubility of the borate or aluminate activators of the present disclosure in aliphatic hydrocarbon solvents increases with the number of aliphatic carbons in the cation group (i.e., the ammonium or the phosphonium). In at least one embodiment, a solubility of at least 10 mM is achieved with an activator having an ammonium or phosphonium group of about 21 aliphatic carbon atoms or more, such as about 25 aliphatic carbons atoms or more, such as about 35 carbon atoms or more.

In at least one embodiment, the solubility of the ammonium borate activators of the present disclosure in aliphatic hydrocarbon solvents increases with the number of aliphatic carbons in the ammonium group. In at least one embodiment, a solubility of at least 10 mM is achieved with an activator having an ammonium group of about 21 aliphatic carbon atoms or more, such as about 25 aliphatic carbons atoms or more, such as about 35 carbon atoms or more.

Useful aliphatic hydrocarbon solvent can be isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In at least one embodiment, aromatics are present in the solvent at less than 1 wt %, such as less than 0.5 wt %, such as at 0 wt % based upon the weight of the solvents. The activators of the present disclosure can be dissolved in one or more additional solvents. Additional solvent includes ethereal, halogenated and N,N-dimethylformamide solvents.

In at least one embodiment, the aliphatic solvent is isohexane and/or methylcyclohexane.

Optional Scavengers or Co-Activators

In addition to these activator compounds, scavengers or co-activators may be used. Aluminum alkyl or organoaluminum compounds which may be utilized as scavengers or co-activators include, for example, trimethylaluminum, triethylaluminum, triisobutylaluminum, tri-n-hexylaluminum, tri-n-octylaluminum, and diethyl zinc.

In at least one embodiment, little or no scavenger is used in the process to produce the ethylene polymer. Scavenger (such as trialkyl aluminum) can be present at zero mol %, alternately the scavenger is present at a molar ratio of scavenger metal to transition metal of less than 100:1, such as less than 50:1, such as less than 15:1, such as less than 10:1.

Transition Metal Catalyst Compounds

Any transition metal compound capable of catalyzing a reaction, such as a polymerization reaction, upon activation with an activator as described above is suitable for use in polymerization processes of the present disclosure. Transition metal compounds known as metallocenes are exemplary catalyst compounds according to the present disclosure.

In at least one embodiment, the present disclosure provides a catalyst system comprising a catalyst compound having a metal atom. The catalyst compound can be a metallocene catalyst compound. The metal can be a Group 3 through Group 12 metal atom, such as Group 3 through Group 10 metal atoms, or lanthanide Group atoms. The catalyst compound having a Group 3 through Group 12 metal atom can be monodentate or multidentate, such as bidentate, tridentate, or tetradentate, where a heteroatom of the catalyst, such as phosphorous, oxygen, nitrogen, or sulfur is chelated to the metal atom of the catalyst. Non-limiting examples include bis(phenolate)s. In at least one embodiment, the Group 3 through Group 12 metal atom is selected from Group 5, Group 6, Group 8, or Group 10 metal atoms. In at least one embodiment, a Group 3 through Group 10 metal atom is selected from Cr, Sc, Ti, Zr, Hf, V, Nb, Ta, Mn, Re, Fe, Ru, Os, Co, Rh, Ir, and Ni. In at least one embodiment, a metal atom is selected from Groups 4, 5, and 6 metal atoms. In at least one embodiment, a metal atom is a Group 4 metal atom selected from Ti, Zr, or Hf. The oxidation state of the metal atom can range from 0 to +7, for example +1, +2, +3, +4, or +5, for example +2, +3, or +4.

Metallocene Catalyst Compounds

A "metallocene" catalyst compound is preferably a transition metal catalyst compound having one, two, or three, typically one or two, substituted or unsubstituted cyclopentadienyl ligands (such as substituted or unsubstituted Cp, Ind or Flu) bound to the transition metal. Metallocene catalyst compounds as used herein include metallocenes comprising Group 3 to Group 12 metal complexes, such as, Group 4 to Group 6 metal complexes, for example, Group 4 metal complexes. The metallocene catalyst compound of catalyst systems of the present disclosure may be unbridged metallocene catalyst compounds represented by the formula: $Cp^A Cp^B M'X'_n$, wherein each $Cp^A$ and $Cp^B$ is independently selected from cyclopentadienyl ligands (for example, Cp, Ind, or Flu) and ligands isolobal to cyclopentadienyl, one or both $Cp^A$ and $Cp^B$ may contain heteroatoms, and one or both $Cp^A$ and $Cp^B$ may be substituted by one or more R" groups; M' is selected from Groups 3 through 12 atoms and lanthanide Group atoms; X' is an anionic leaving group; n is 0 or an integer from 1 to 4; each R" is independently selected from alkyl, substituted alkyl, heteroalkyl, alkenyl, substituted alkenyl, heteroalkenyl, alkynyl, substituted alkynyl, heteroalkynyl, alkoxy, aryloxy, alkylthio, arylthio, aryl, substituted aryl, heteroaryl, aralkyl, aralkylene, alkaryl, alkarylene, haloalkyl, haloalkenyl, haloalkynyl, heteroalkyl, heterocycle, heteroaryl, a heteroatom-containing group, hydrocarbyl, substituted hydrocarbyl, heterohydrocarbyl, silyl, boryl, phosphino, phosphine, amino, amine, ether, and thioether.

In at least one embodiment, each $Cp^A$ and $Cp^B$ is independently selected from cyclopentadienyl, indenyl, fluorenyl, indacenyl, tetrahydroindenyl, cyclopentaphenanthreneyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated and substituted versions thereof. Each $Cp^A$ and $Cp^B$ may independently be indacenyl or tetrahydroindenyl.

The metallocene catalyst compound may be a bridged metallocene catalyst compound represented by the formula: $Cp^A(T)Cp^B M'X'_n$, wherein each $Cp^A$ and $Cp^B$ is independently selected from cyclopentadienyl ligands (for example, Cp, Ind, or Flu) and ligands isolobal to cyclopentadienyl, where one or both $Cp^A$ and $Cp^B$ may contain heteroatoms, and one or both $Cp^A$ and $Cp^B$ may be substituted by one or more R" groups; M' is selected from Groups 3 through 12 atoms and lanthanide Group atoms, preferably Group 4; X' is an anionic leaving group; n is 0 or an integer from 1 to 4; (T) is a bridging group selected from divalent alkyl, divalent substituted alkyl, divalent heteroalkyl, divalent alkenyl, divalent substituted alkenyl, divalent heteroalkenyl, divalent alkynyl, divalent substituted alkynyl, divalent heteroalkynyl, divalent alkoxy, divalent aryloxy, divalent alkylthio, divalent arylthio, divalent aryl, divalent substituted aryl, divalent heteroaryl, divalent aralkyl, divalent aralkylene, divalent alkaryl, divalent alkarylene, divalent haloalkyl, divalent haloalkenyl, divalent haloalkynyl, divalent heteroalkyl, divalent heterocycle, divalent heteroaryl, a divalent heteroatom-containing group, divalent hydrocarbyl, divalent substituted hydrocarbyl, divalent heterohydrocarbyl, divalent silyl, divalent boryl, divalent phosphino, divalent phosphine, divalent amino, divalent amine, divalent ether, divalent thioether. R" is selected from alkyl, substituted alkyl, heteroalkyl, alkenyl, substituted alkenyl, heteroalkenyl, alkynyl, substituted alkynyl, heteroalkynyl, alkoxy, aryloxy, alkylthio, arylthio, aryl, substituted aryl, heteroaryl, aralkyl, aralkylene, alkaryl, alkarylene, haloalkyl, haloalkenyl, haloalkynyl, heteroalkyl, heterocycle, heteroaryl, a heteroatom-containing group, hydrocarbyl, substituted hydrocarbyl, heterohydrocarbyl, silyl, boryl, phosphino, phosphine, amino, amine, germanium, ether, and thioether.

In at least one embodiment, each of $Cp^A$ and $Cp^B$ is independently selected from cyclopentadienyl, indenyl, fluorenyl, cyclopentaphenanthreneyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated, and substituted versions thereof, preferably cyclopentadienyl, n-propylcyclopentadienyl, indenyl, pentamethylcyclopentadienyl, tetramethylcyclopentadienyl, and n-butylcyclopentadienyl. Each $Cp^A$ and $Cp^B$ may independently be indacenyl or tetrahydroindenyl.

(T) is a bridging group containing at least one Group 13, 14, 15, or 16 element, in particular boron or a Group 14, 15 or 16 element, preferably (T) is O, S, NR', or SiR'$_2$, where each R' is independently hydrogen or $C_1$-$C_{20}$ hydrocarbyl.

In another embodiment, the metallocene catalyst compound is represented by the formula:

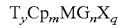

where Cp is independently a substituted or unsubstituted cyclopentadienyl ligand (for example, substituted or unsubstituted Cp, Ind, or Flu) or substituted or unsubstituted ligand isolobal to cyclopentadienyl; M is a Group 4 transition metal; G is a heteroatom group represented by the formula $JR^*_z$ where J is N, P, O or S, and R* is a linear, branched, or cyclic $C_1$-$C_{20}$ hydrocarbyl; z is 1 or 2; T is a bridging group; y is 0 or 1; X is a leaving group; m=1, n=1, 2 or 3, q=0, 1, 2 or 3, and the sum of m+n+q is equal to the coordination number of the transition metal.

In at least one embodiment, J is N, and R* is methyl, ethyl, propyl, butyl, pentyl, hexyl, heptyl, octyl, nonyl, cyclooctyl, cyclododecyl, decyl, undecyl, dodecyl, adamantyl or an isomer thereof.

In at least one embodiment, the catalyst compound is represented by formula (II) or formula (III):

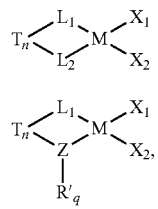

wherein in each of formula (II) and formula (III):

M is the metal center, and is a Group 4 metal, such as titanium, zirconium or hafnium, such as zirconium or hafnium when $L_1$ and $L_2$ are present and titanium when Z is present; n is 0 or 1:

T is an optional bridging group which, if present, is a bridging group containing at least one Group 13, 14, 15, or 16 element, in particular boron or a Group 14, 15 or 16 element (preferably T is selected from dialkylsilyl, diarylsilyl, dialkylmethyl, ethylenyl (—CH$_2$—CH$_2$—) or hydrocarbylethylenyl wherein one, two, three or four of the hydrogen atoms in ethylenyl are substituted by hydrocarbyl, where hydrocarbyl can be independently $C_1$ to $C_{16}$ alkyl or phenyl, tolyl, xylyl and the like), and when T is present, the catalyst represented can be in a racemic or a meso form;

$L_1$ and $L_2$ are independently cyclopentadienyl, indenyl, tetrahydroindenyl or fluorenyl, optionally substituted, that are each bonded to M, or $L_1$ and $L_2$ are independently cyclopentadienyl, indenyl, tetrahydroindenyl or fluorenyl, which are optionally substituted, in which any two adjacent substituents on $L_1$ and $L^2$ are optionally joined to form a substituted or unsubstituted, saturated, partially unsaturated, or aromatic cyclic or polycyclic substituent;

Z is nitrogen, oxygen, sulfur or phosphorus (preferably nitrogen);

q is 1 or 2 (preferably q is 1 when Z is N);

R' is a cyclic, linear or branched $C_1$ to $C_{40}$ alkyl or substituted alkyl group;

$X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or $X_1$ and $X_2$ are joined and bound to the metal atom to form a metallacycle ring containing from about 3 to about 20 carbon atoms; or both together can be an olefin, diolefin or aryne ligand.

Preferably, T in any formula herein is present and is a bridging group containing at least one Group 13, 14, 15, or 16 element, in particular a Group 14 element. Examples of suitable bridging groups include P(=S)R', P(=Se)R', P(=O)R', R'$_2$C, R'$_2$Si, R'$_2$Ge, R'$_2$CCR'$_2$, R'$_2$CCR'$_2$CR'$_2$, R'$_2$CCR'$_2$CR'$_2$CR'$_2$, R'C=CR', R'C=CR'CR'$_2$, R'$_2$CCR'=CR'CR'$_2$, R'C=CR'CR'=CR', R'C=CR'CR'$_2$CR'$_2$, R'$_2$CSiR'$_2$, R'$_2$SiSiR'$_2$, R'$_2$SiOSiR'$_2$, R'$_2$CSiR'$_2$CR'$_2$, R'$_2$SiCR'$_2$SiR'$_2$, R'C=CR'SiR'$_2$, R'$_2$CGeR'$_2$, R'$_2$GeGeR'$_2$, R'$_2$CGeR'$_2$CR'$_2$, R'$_2$GeCR'$_2$GeR'$_2$, R'$_2$SiGeR'$_2$, R'C=CR'GeR'$_2$, R'B, R'$_2$C—BR', R'$_2$C—BR'—CR'$_2$, R'$_2$C—O—CR'$_2$, R'$_2$CR'$_2$C—O—CR'$_2$CR'$_2$, R'$_2$C—O—CR'$_2$CR'$_2$, R'$_2$C—O—CR'=CR', R'$_2$C—S—CR'$_2$, R'$_2$CR'$_2$C—S—CR'$_2$CR'$_2$, R'$_2$C—S—CR'$_2$CR'$_2$, R'$_2$C—S—CR'=CR', R'$_2$C—Se—CR'$_2$, R'$_2$CR'$_2$C—Se—CR'$_2$CR'$_2$, R'$_2$C—Se—CR'$_2$CR'$_2$, R'$_2$C—Se—CR'=CR', R'$_2$C—N=CR', R'$_2$C—NR'—CR'$_2$, R'$_2$C—NR'—CR'$_2$CR'$_2$, R'$_2$C—NR'—CR'=CR', R'$_2$CR'$_2$C—NR'—CR'$_2$CR'$_2$, R'$_2$C—P=CR', R'$_2$C—PR'—CR'$_2$, O, S, Se, Te, NR', PR', AsR', SbR', O—O, S—S, R'N—NR', R'P—PR', O—S, O—NR', O—PR', S—NR', S—PR', and R'N—PR' where R' is hydrogen or a $C_1$-$C_{20}$ containing hydrocarbyl, substituted hydrocarbyl, halocarbyl, substituted halocarbyl, silylcarbyl or germylcarbyl substituent and optionally two or more adjacent R' may join to form a substituted or unsubstituted, saturated, partially unsaturated or aromatic, cyclic or polycyclic substituent. Preferred examples for the bridging group T include CH$_2$, CH$_2$CH$_2$, SiMe$_2$, SiPh$_2$, SiMePh, Si(CH$_2$)$_3$, Si(CH$_2$)$_4$, O, S, NPh, PPh, NMe, PMe, NEt, NPr, NBu, PEt, PPr, Me$_2$SiOSiMe$_2$, and PBu.

In a preferred embodiment of the invention in any embodiment of any formula described herein, T is represented by the formula $R^a_2J$ or $(R^a_2J)_2$, where J is C, Si, or Ge, and each $R^a$ is, independently, hydrogen, halogen, $C_1$ to $C_{20}$ hydrocarbyl (such as methyl, ethyl, propyl, butyl, pentyl, hexyl, heptyl, octyl, nonyl, decyl, undecyl, or dodecyl) or a $C_1$ to $C_{20}$ substituted hydrocarbyl, and two $R^a$ can form a cyclic structure including aromatic, partially saturated, or saturated cyclic or fused ring system. Preferably, T is a bridging group comprising carbon or silica, such as dialkylsilyl, preferably T is selected from CH$_2$, CH$_2$CH$_2$, C(CH$_3$)$_2$, SiMe$_2$, SiPh$_2$, SiMePh, silylcyclobutyl (Si(CH$_2$)$_3$), (Ph)$_2$C, (p-(Et)$_3$SiPh)$_2$C, Me$_2$SiOSiMe$_2$, and cyclopentasilylene (Si(CH$_2$)$_4$).

In at least one embodiment, the catalyst compound has a symmetry that is C2 symmetrical.

The metallocene catalyst component may comprise any combination of any "embodiment" described herein.

Suitable metallocenes useful herein include, but are not limited to, the metallocenes disclosed and referenced in the US patents cited above, as well as those disclosed and referenced in U.S. Pat. Nos. 7,179,876; 7,169,864; 7,157,531; 7,129,302; 6,995,109; 6,958,306; 6,884,748; 6,689,847; US Patent publication 2007/0055028, and published PCT Applications WO 97/22635; WO 00/699/22; WO 01/30860; WO 01/30861; WO 02/46246; WO 02/50088; WO 04/026921; and WO 06/019494, all fully incorporated herein by reference. Additional catalysts suitable for use herein include those referenced in U.S. Pat. Nos. 6,309,997; 6,265,338; US Patent publication 2006/019925, and the following articles: Resconi, L. et al. (2000) "Selectivity in Propene Polymerization with Metallocene Catalysts," *Chem. Rev.*, v. 100(4), pp. 1253-1346; Gibson, V. C. et al. (2003) "Advances in Non-Metallocene Olefin Polymerization Catalysis," *Chem. Rev.*, v. 103(1), pp. 283-316; Nakayama, Y. et al. (2006) "MgCl$_2$/R'$_n$Al(OR)$_{3-n}$: An Excellent Activator/Support for Transition-Metal Complexes for Olefin Polymerization," *Chem. Eur. J.*, v. 12, pp. 7546-7556; Nakayama, Y et al. (2004), "Olefin Polymerization Behavior of bis(phenoxy-imine) Zr, Ti, and V complexes with MgCl$_2$-based Cocatalysts," *J. Mol.* Catalysis A: Chemical, v. 213, pp. 141-150; Nakayama, Y. et al. (2005), Propylene Polymerization Behavior of Fluorinated Bis(phenoxy-imine) Ti Complexes with an MgCl$_2$-Based Compound (MgCl$_2$-Supported Ti-Based Catalysts)," *Macromol. Chem. Phys.*, v. 206(18), pp. 1847-1852; and Matsui, S. et al. (2001) "A Family of Zirconium Complexes Having Two Phenoxy-Imine Chelate Ligands for Olefin Polymerization," *J. Am. Chem. Soc.*, v. 123(28), pp. 6847-6856.

Exemplary metallocene compounds useful herein are include:

bis(cyclopentadienyl)zirconium dichloride,
bis(n-butylcyclopentadienyl)zirconium dichloride,
bis(n-butylcyclopentadienyl)zirconium dimethyl,
bis(pentamethylcyclopentadienyl)zirconium dichloride,
bis(pentamethylcyclopentadienyl)zirconium dimethyl,
bis(pentamethylcyclopentadienyl)hafnium dichloride,
bis(pentamethylcyclopentadienyl)zirconium dimethyl,
bis(1-methyl-3-n-butylcyclopentadienyl)zirconium dichloride,
bis(1-methyl-3-n-butylcyclopentadienyl)zirconium dimethyl,
bis(1-methyl-3-n-butylcyclopentadienyl)hafnium dichloride,
bis(1-methyl-3-n-butylcyclopentadienyl)zirconium dimethyl,
bis(indenyl)zirconium dichloride, bis(indenyl)zirconium dimethyl,
bis(tetrahydro-1-indenyl)zirconium dichloride,
bis(tetrahydro-1-indenyl)zirconium dimethyl,
(n-propyl cyclopentadienyl, pentamethyl cyclopentadienyl) zirconium dichloride, and
(n-propyl cyclopentadienyl, pentamethyl cyclopentadienyl) zirconium dimethyl.

In at least one embodiment, the catalyst compound may be selected from:
dimethylsilylbis(tetrahydroindenyl)MX$_n$,
dimethylsilyl bis(2-methylindenyl)MX$_n$,
dimethylsilyl bis(2-methylfluorenyl)MX$_n$,
dimethylsilyl bis(2-methyl-5,7-propylindenyl)MX$_n$,
dimethylsilyl bis(2-methyl-4-phenylindenyl)MX$_n$,
dimethylsilyl bis(2-ethyl-5-phenylindenyl)MX$_n$,
dimethylsilyl bis(2-methyl-4-biphenylindenyl)MX$_n$,
dimethylsilylene bis(2-methyl-4-carbazolylindenyl)MX$_n$,
rac-dimethylsilyl-bis-(5,6,7,8-tetrahydro-5,5,8,8-tetramethyl-2-methyl-1H-benz(f)indene)MX$_n$,
diphenylmethylene (cyclopentadienyl)(fluoreneyl)MX$_n$,
bis(methylcyclopentadienyl)MX$_n$,
rac-dimethylsiylbis(2-methyl,3-propyl indenyl)MX$_n$,
dimethylsilylbis(indenyl)MX$_n$,
Rac-meso-diphenylsilyl-bis(n-propylcyclopentadienyl) MX$_n$,
1, 1'-bis(4-triethylsilylphenyl)methylene-(cyclopentadienyl) (3,8-di-tertiary-butyl-1-fluorenyl)MX$_n$ (bridge is considered the 1 position),
bis-trimethylsilylphenyl-methylene(cyclopentadienyl)(di-t-butylfluorenyl)MX$_n$,
bis-trimethylsilylphenyl-methylene(cyclopentadienyl)(fluorenyl)MX$_n$,
bisphenylmethylene(cyclopentadienyl)(dimethylfluorenyl) MX$_n$,
bis(n-propylcyclopentadienyl)MX$_n$,
bis(n-butylcyclopentadienyl)MX$_n$,
bis(n-pentylcyclopentadienyl)MX$_n$,
(n-propyl cyclopentadienyl)(n-butylcyclopentadienyl)MX$_n$,
bis[(2-trimethylsilylethyl)cyclopentadienyl]MX$_n$,
bis(trimethylsilyl cyclopentadienyl)MX$_n$,
dimethylsilylbis(n-propylcyclopentadienyl)MX$_n$,
dimethylsilylbis(n-butylcyclopentadienyl)MX$_n$,
bis(1-n-propyl-2-methylcyclopentadienyl)MX$_n$,
(n-propylcyclopentadienyl)(1-n-propyl-3-n-butylcyclopentadienyl)MX$_n$,
bis(1-methyl, 3-n-butyl cyclopentadienyl)MX$_n$,
bis(indenyl)MX$_n$,
dimethylsilyl (tetramethylcyclopentadienyl)(cyclododecylamido)MX$_n$,
dimethylsilyl (tetramethylcyclopentadienyl)(t-butylamido) MX$_n$,
μ-(CH$_3$)$_2$Si(cyclopentadienyl)(1-adamantylamido)MX$_n$,
μ-(CH$_3$)$_2$Si(3-tertbutylcyclopentadienyl)(1-adamantylamido)MX$_n$,
μ-(CH$_3$)$_2$(tetramethylcyclopentadienyl)(1-adamantylamido) MX$_n$,
μ-(CH$_3$)$_2$Si(tetramethylcyclopentadienyl)(1-adamantylamido)MX$_n$,
μ-(CH$_3$)$_2$C(tetramethylcyclopentadienyl)(1-adamantylamido)MX$_n$,
μ-(CH$_3$)$_2$Si(tetramethylcyclopentadienyl)(1-tertbutylamido) MX$_n$,
μ-(CH$_3$)$_2$Si(fluorenyl)(1-tertbutylamido)MX$_n$,
μ-(CH$_3$)$_2$Si(tetramethylcyclopentadienyl)(1-cyclododecylamido)MX$_n$,
μ-(C$_6$H$_5$)$_2$C(tetramethylcyclopentadienyl)(1-cyclododecylamido)MX$_n$,
μ-(CH$_3$)$_2$Si(η5-2,6,6-trimethyl-1,5,6,7-tetrahydro-s-indacen-1-yl)(tertbutylamido)MX$_n$,
where M is selected from Ti, Zr, and Hf; where X is selected from the group consisting of halogens, hydrides, C$_{1-12}$ alkyls, C$_{2-12}$ alkenyls, C$_{6-12}$ aryls, C$_{7-20}$ alkylaryls, C$_{1-12}$ alkoxys, C$_{6-16}$ aryloxys, C$_{7-18}$ alkylaryloxys, C$_{1-12}$ fluoroalkyls, C$_{6-12}$ fluoroaryls, and C$_{1-12}$ heteroatom-containing hydrocarbons, substituted derivatives thereof, and combinations thereof, and where n is zero or an integer from 1 to 4, preferably X is selected from halogens (such as bromide, fluoride, chloride), or C$_1$ to C$_{20}$ alkyls (such as methyl, ethyl, propyl, butyl, and pentyl) and n is 1 or 2, preferably 2.

In other embodiments of the invention, the catalyst is one or more of:

bis(1-methyl, 3-n-butyl cyclopentadienyl)M(R)$_2$;
dimethylsilyl bis(indenyl)M(R)$_2$;
bis(indenyl)M(R)$_2$;
dimethylsilyl bis(tetrahydroindenyl)M(R)$_2$;
bis(n-propylcyclopentadienyl)M(R)$_2$;
dimethylsilyl (tetramethylcyclopentadienyl)(cyclododecylamido)M(R)$_2$;
dimethylsilyl (tetramethylcyclopentadienyl)(cyclododecylamido)M(R)$_2$;
dimethylsilyl (tetramethylcyclopentadienyl)(t-butylamido) M(R)$_2$;
dimethylsilyl (tetramethylcyclopentadienyl)(t-butylamido) M(R)$_2$;
μ-(CH$_3$)$_2$Si(cyclopentadienyl)(1-adamantylamido)M(R)$_2$;
μ-(CH$_3$)$_2$Si(3-tertbutylcyclopentadienyl)(1-adamantylamido)M(R)$_2$;
μ-(CH$_3$)$_2$(tetramethylcyclopentadienyl)(1-adamantylamido) M(R)$_2$;
μ-(CH$_3$)$_2$Si(tetramethylcyclopentadienyl)(1-adamantylamido)M(R)$_2$;
μ-(CH$_3$)$_2$C(tetramethylcyclopentadienyl)(1-adamantylamido)M(R)$_2$;
μ-(CH$_3$)$_2$Si(tetramethylcyclopentadienyl)(1-tertbutylamido) M(R)$_2$;
μ-(CH$_3$)$_2$Si(fluorenyl)(1-tertbutylamido)M(R)$_2$;
μ-(CH$_3$)$_2$Si(tetramethylcyclopentadienyl)(1-cyclododecylamido)M(R)$_2$;
μ-(C$_6$H$_5$)$_2$C(tetramethylcyclopentadienyl)(1-cyclododecylamido)M(R)$_2$;
μ-(CH$_3$)$_2$Si($\eta^5$-2,6,6-trimethyl-1,5,6,7-tetrahydro-s-indacen-1-yl)(tertbutylamido)M(R)$_2$;
where M is selected from Ti, Zr, and Hf; and R is selected from halogen or C$_1$ to C$_5$ alkyl.

In preferred embodiments of the invention, the catalyst compound is one or more of:
dimethylsilyl (tetramethylcyclopentadienyl)(cyclododecylamido)titanium dimethyl;
dimethylsilyl (tetramethylcyclopentadienyl)(cyclododecylamido)titanium dimethyl;
dimethylsilyl (tetramethylcyclopentadienyl)(t-butylamido) titanium dimethyl;
dimethylsilyl (tetramethylcyclopentadienyl)(t-butylamido) titanium dimethyl;
μ-(CH$_3$)$_2$Si(cyclopentadienyl)(1-adamantylamido)titanium dimethyl;
μ-(CH$_3$)$_2$Si(3-tertbutylcyclopentadienyl)(1-adamantylamido)titanium dimethyl;
μ-(CH$_3$)$_2$(tetramethylcyclopentadienyl)(1-adamantylamido) titanium dimethyl;
μ-(CH$_3$)$_2$Si(tetramethylcyclopentadienyl)(1-adamantylamido)titanium dimethyl;
μ-(CH$_3$)$_2$C(tetramethylcyclopentadienyl)(1-adamantylamido)titanium dimethyl;
μ-(CH$_3$)$_2$Si(tetramethylcyclopentadienyl)(1-tertbutylamido) titanium dimethyl$_2$;
μ-(CH$_3$)$_2$Si(fluorenyl)(1-tertbutylamido)titanium dimethyl;
μ-(CH$_3$)$_2$Si(tetramethylcyclopentadienyl)(1-cyclododecylamido)titanium dimethyl;
μ-(C$_6$H$_5$)$_2$C(tetramethylcyclopentadienyl)(1-cyclododecylamido)titanium dimethyl; and
μ-(CH$_3$)$_2$Si($\eta^5$-2,6,6-trimethyl-1,5,6,7-tetrahydro-s-indacen-1-yl)(tertbutylamido)titanium dimethyl.

In at least one embodiment, the catalyst is dimethylsilyl-bis(indenyl)hafnium dimethyl, and or 1, 1'-bis(4-triethylsilylphenyl)methylene-(cyclopentadienyl)(3,8-di-tertiary-butyl-1-fluorenyl)hafnium dimethyl.

In at least one embodiment, the catalyst compound is one or more of:
bis(1-methyl, 3-n-butyl cyclopentadienyl)hafnium dimethyl,
bis(1-methyl, 3-n-butyl cyclopentadienyl)zirconium dimethyl,
dimethylsilyl bis(indenyl)zirconium dimethyl,
dimethylsilyl bis(indenyl)hafnium dimethyl,
bis(indenyl)zirconium dimethyl,
bis(indenyl)hafnium dimethyl,
dimethylsilyl bis(tetrahydroindenyl)zirconium dimethyl,
bis(n-propylcyclopentadienyl)zirconium dimethyl,
dimethylsilylbis(tetrahydroindenyl)hafnium dimethyl,
dimethylsilyl bis(2-methylindenyl)zirconium dimethyl,
dimethylsilyl bis(2-methylfluorenyl)zirconium dimethyl,
dimethylsilyl bis(2-methylindenyl)hafnium dimethyl,
dimethylsilyl bis(2-methylfluorenyl)hafnium dimethyl,
dimethylsilyl bis(2-methyl-5,7-propylindenyl) zirconium dimethyl,
dimethylsilyl bis(2-methyl-4-phenylindenyl) zirconium dimethyl,
dimethylsilyl bis(2-ethyl-5-phenylindenyl) zirconium dimethyl,
dimethylsilyl bis(2-methyl-4-biphenylindenyl) zirconium dimethyl,
dimethylsilylene bis(2-methyl-4-carbazolylindenyl) zirconium dimethyl,
rac-dimethylsilyl-bis-(5,6,7,8-tetrahydro-5,5,8,8-tetramethyl-2-methyl-1H-benz(f)indene)hafnium dimethyl,
diphenylmethylene (cyclopentadienyl)(fluoreneyl)hafnium dimethyl,
bis(methylcyclopentadienyl)zirconium dimethyl,
rac-dimethylsiylbis(2-methyl,3-propyl indenyl)hafnium dimethyl,
dimethylsilylbis(indenyl)hafnium dimethyl,
dimethylsilylbis(indenyl)zirconium dimethyl,
dimethyl rac-dimethylsilyl-bis-(5,6,7,8-tetrahydro-5,5,8,8-tetramethyl-2-methyl-1H-benz(f)indene)hafnium dimethyl,
Rac-meso-diphenylsilyl-bis(n-propylcyclopentadienyl)hafnium dimethyl,
1, 1'-bis(4-triethylsilylphenyl)methylene-(cyclopentadienyl) (3,8-di-tertiary-butyl-1-fluorenyl)hafnium X$_n$ (bridge is considered the 1 position),
bis-trimethylsilylphenyl-methylene(cyclopentadienyl)(di-t-butylfluorenyl)hafnium dimethyl,
bis-trimethylsilylphenyl-methylene(cyclopentadienyl)(fluorenyl)hafnium dimethyl,
bisphenylmethylene(cyclopentadienyl)(dimethylfluorenyl) hafnium dimethyl,
bis(n-propylcyclopentadienyl)hafnium dimethyl,
bis(n-butylcyclopentadienyl)hafnium dimethyl,
bis(n-pentylcyclopentadienyl)hafnium dimethyl,
(n-propyl cyclopentadienyl)(n-butylcyclopentadienyl)hafnium dimethyl,
bis[(2-trimethylsilylethyl)cyclopentadienyl]hafnium dimethyl,
bis(trimethylsilyl cyclopentadienyl)hafnium dimethyl,
dimethylsilylbis(n-propylcyclopentadienyl)hafnium dimethyl,
dimethylsilylbis(n-butylcyclopentadienyl)hafnium dimethyl,
bis(1-n-propyl-2-methylcyclopentadienyl)hafnium dimethyl, and
(n-propylcyclopentadienyl)(1-n-propyl-3-n-butylcyclopentadienyl)hafnium dimethyl,
bis(n-propylcyclopentadienyl)hafnium dimethyl,
bis(n-butylcyclopentadienyl)hafnium dimethyl, bis(n-pentylcyclopentadienyl)hafnium dimethyl,
(n-propyl cyclopentadienyl)(n-butylcyclopentadienyl)hafnium dimethyl,
bis[(2-trimethylsilylethyl)cyclopentadienyl]hafnium dimethyl,
bis(trimethylsilyl cyclopentadienyl)hafnium dimethyl,
dimethylsilylbis(n-propylcyclopentadienyl)hafnium dimethyl,
dimethylsilylbis(n-butylcyclopentadienyl)hafnium dimethyl,
bis(1-n-propyl-2-methylcyclopentadienyl)hafnium dimethyl,
(n-propylcyclopentadienyl)(1-n-propyl-3-n-butylcyclopentadienyl)hafnium dimethyl, and
dimethylsilyl(3-n-propylcyclopentadienyl)(tetramethylcyclopentadienyl)zirconium dimethyl.

Non-Metallocene Catalyst Compounds

Transition metal complexes for polymerization processes can include any olefin polymerization catalyst. Suitable catalyst components may include "non-metallocene complexes" that are defined to be transition metal complexes that do not feature a cyclopentadienyl anion or substituted cyclopentadienyl anion donors (e.g., cyclopentadienyl, fluorenyl, indenyl, methylcyclopentadienyl). Examples of families of non-metallocene complexes that may be suitable can include late transition metal pyridylbisimines (e.g., U.S. Pat. No. 7,087,686), group 4 pyridyldiamidos (e.g., U.S. Pat. No. 7,973,116), quinolinyldiamidos (e.g., US Pub. No. 2018/0002352 A1), pyridylamidos (e.g., U.S. Pat. No. 7,087,690), phenoxyimines (e.g., Makio, H. et al. (2009) "Development and Application of FI Catalysts for Olefin Polymerization: Unique Catalysis and Distinctive Polymer Formation," *Accounts of Chemical Research*, v. 42(10), pp. 1532-1544), and bridged bi-aromatic complexes (e.g., U.S. Pat. No. 7,091,292), the disclosures of which are incorporated herein by reference.

Catalyst complexes that are suitable for use in combination with the activators described herein include: pyridyldiamido complexes; quinolinyldiamido complexes; phenoxyimine complexes; bisphenolate complexes; cyclopentadienyl-amidinate complexes; and iron pyridyl bis(imine) complexes or any combination thereof, including any combination with metallocene complexes.

The term "pyridyldiamido complex" or "pyridyldiamide complex" or "pyridyldiamido catalyst" or "pyridyldiamide catalyst" refers to a class of coordination complexes described in U.S. Pat. No. 7,973,116B2, US 2012/0071616A1, US 2011/0224391A1, US 2011/0301310A1, US 2015/0141601A1, U.S. Pat. Nos. 6,900,321 and 8,592,615 that feature a dianionic tridentate ligand that is coordinated to a metal center through one neutral Lewis basic donor atom (e.g., a pyridine group) and a pair of anionic amido or phosphido (i.e., deprotonated amine or phosphine) donors. In these complexes the pyridyldiamido ligand is coordinated to the metal with the formation of one five membered chelate ring and one seven membered chelate ring. It is possible for additional atoms of the pyridyldiamido ligand to be coordinated to the metal without affecting the catalyst function upon activation; an example of this could be a cyclometalated substituted aryl group that forms an additional bond to the metal center.

The term "quinolinyldiamido complex" or "quinolinyldiamido catalyst" or "quinolinyldiamide complex" or "quinolinyldiamide catalyst" refers to a related class of pyridyldiamido complex/catalyst described in US 2018/0002352 where a quinolinyl moiety is present instead of a pyridyl moiety.

The term "phenoxyimine complex" or "phenoxyimine catalyst" refers to a class of coordination complexes described in EP 0874005 that feature a monoanionic bidentate ligand that is coordinated to a metal center through one neutral Lewis basic donor atom (e.g., an imine moiety) and an anionic aryloxy (i.e., deprotonated phenoxy) donor. Typically two of these bidentate phenoxyimine ligands are coordinated to a group 4 metal to form a complex that is useful as a catalyst component.

The term "bisphenolate complex" or "bisphenolate catalyst" refers to a class of coordination complexes described in U.S. Pat. No. 6,841,502, WO 2017/004462, and WO 2006/020624 that feature a dianionic tetradentate ligand that is coordinated to a metal center through two neutral Lewis basic donor atoms (e.g., oxygen bridge moieties) and two anionic aryloxy (i.e., deprotonated phenoxy) donors.

The term "cyclopentadienyl-amidinate complex" or "cyclopentadienyl-amidinate catalyst" refers to a class of coordination complexes described in U.S. Pat. No. 8,188,200 that typically feature a group 4 metal bound to a cyclopentadienyl anion, a bidentate amidinate anion, and a couple of other anionic groups.

The term "iron pyridyl bis(imine) complex" refers to a class of iron coordination complexes described in U.S. Pat. No. 7,087,686 that typically feature an iron metal center coordinated to a neutral, tridentate pyridyl bis(imine) ligand and two other anionic ligands.

Non-metallocene complexes can include iron complexes of tridentate pyridylbisimine ligands, zirconium and hafnium complexes of pyridylamido ligands, zirconium and hafnium complexes of tridentate pyridyldiamido ligands, zirconium and hafnium complexes of tridentate quinolinyldiamido ligands, zirconium and hafnium complexes of bidentate phenoxyimine ligands, and zirconium and hafnium complexes of bridged bi-aromatic ligands.

Suitable non-metallocene complexes can include zirconium and hafnium non-metallocene complexes. In at least one embodiment, non-metallocene complexes for the present disclosure include group 4 non-metallocene complexes including two anionic donor atoms and one or two neutral donor atoms. Suitable non-metallocene complexes for the present disclosure include group 4 non-metallocene complexes including an anionic amido donor. Suitable non-metallocene complexes for the present disclosure include group 4 non-metallocene complexes including an anionic aryloxide donor atom. Suitable non-metallocene complexes for the present disclosure include group 4 non-metallocene complexes including two anionic aryloxide donor atoms and two additional neutral donor atoms.

A catalyst compounds can be a quinolinyldiamido (QDA) transition metal complex represented by Formula (BI), such as by Formula (BII), such as by Formula (BIII):

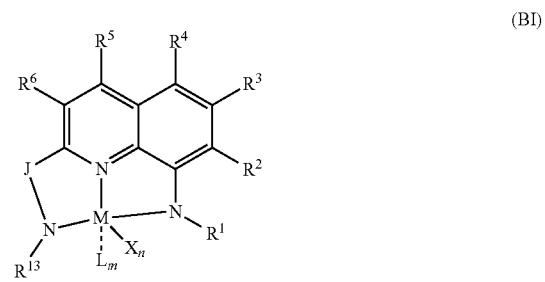

(BI)

-continued (BII)

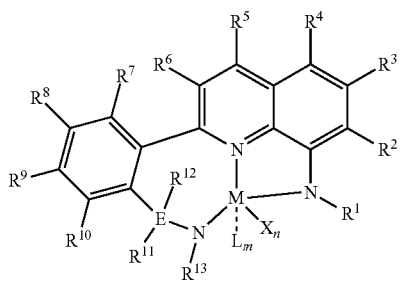

(BIII)

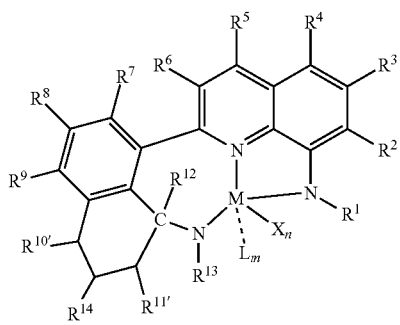

wherein:

M is a group 3, 4, 5, 6, 7, 8, 9, 10, 11, or 12 metal, such as a group 4 metal;

J is group including a three-atom-length bridge between the quinoline and the amido nitrogen, such as a group containing up to 50 non-hydrogen atoms;

E is carbon, silicon, or germanium;

X is an anionic leaving group, (such as a hydrocarbyl group or a halogen);

L is a neutral Lewis base;

$R^1$ and $R^{13}$ are independently selected from the group including of hydrocarbyls, substituted hydrocarbyls, and silyl groups;

$R^2$, $R^3$, $R^4$, $R^5$, $R^6$, R, $R^8$, $R^9$, $R^{10}$, $R^{10'}$, $R^{11}$, $R^{11'}$, $R^{12}$, and $R^{14}$ are independently hydrogen, hydrocarbyl, alkoxy, silyl, amino, aryloxy, substituted hydrocarbyl, halogen, or phosphino;

n is 1 or 2;

m is 0, 1, or 2, where n+m is not greater than 4; and any two R groups (e.g., $R^1$ & $R^2$, $R^2$ & $R^3$, $R^{10}$ and $R^{11}$, etc.) may be joined to form a substituted hydrocarbyl, unsubstituted hydrocarbyl, substituted heterocyclic, or unsubstituted heterocyclic, saturated or unsaturated ring, where the ring has 5, 6, 7, or 8 ring atoms and where substitutions on the ring can join to form additional rings;

any two X groups may be joined together to form a dianionic group;

any two L groups may be joined together to form a bidentate Lewis base; and any X group may be joined to an L group to form a monoanionic bidentate group.

In at least one embodiment, M is a group 4 metal, such as zirconium or hafnium, such as M is hafnium.

Representative non-metallocene transition metal compounds usable for forming poly(alpha-olefin)s of the present disclosure also include tetrabenzyl zirconium, tetra bis(trimethylsilymethyl) zirconium, oxotris(trimethlsilylmethyl) vanadium, tetrabenzyl hafnium, tetrabenzyl titanium, bis(hexamethyl disilazido)dimethyl titanium, tris(trimethyl silyl methyl) niobium dichloride, and tris(trimethylsilylmethyl) tantalum dichloride.

In at least one embodiment, J is an aromatic substituted or unsubstituted hydrocarbyl having from 3 to 30 non-hydrogen atoms, such as J is represented by the formula:

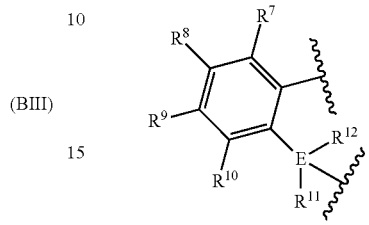

such as J is R

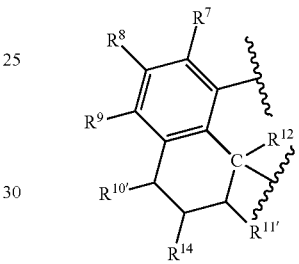

where $R^7$, $R^8$, $R^9$, $R^{10}$, $R^{10'}$, $R^{11}$, $R^{11'}$, $R^{12}$, $R^{14}$ and E are as defined above, and any two R groups (e.g., $R^7$ & $R^8$, $R^8$ & $R^9$, $R^9$ & $R^{10}$, $R^{10}$ & $R^{11}$, etc.) may be joined to form a substituted or unsubstituted hydrocarbyl or heterocyclic ring, where the ring has 5, 6, 7, or 8 ring atoms (such as 5 or 6 atoms), and said ring may be saturated or unsaturated (such as partially unsaturated or aromatic), such as J is an arylalkyl (such as arylmethyl, etc.) or dihydro-1H-indenyl, or tetrahydronaphthalenyl group.

In at least one embodiment, J is selected from the following structures:

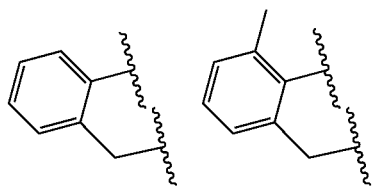

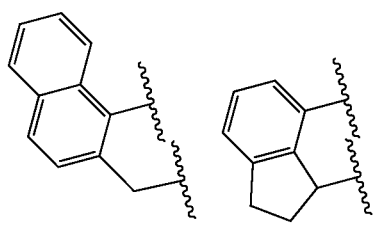

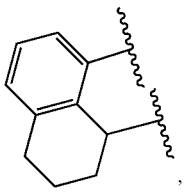, where ⸽ indicates connection to the complex.

In at least one embodiment, E is carbon.

X may be an alkyl (such as alkyl groups having 1 to 10 carbons, such as methyl, ethyl, propyl, butyl, pentyl, hexyl, heptyl, octyl, nonyl, decyl, and isomers thereof), aryl, hydride, alkylsilane, fluoride, chloride, bromide, iodide, triflate, carboxylate, amido (such as $NMe_2$), or alkylsulfonate.

In at least one embodiment, L is an ether, amine or thioether.

In at least one embodiment, $R^7$ and $R^8$ are joined to form a six-membered aromatic ring with the joined $R^7/R^8$ group being —CH=CHCH=CH—.

$R^{10}$ and $R^{11}$ may be joined to form a five-membered ring with the joined $R^{10}R^{11}$ group being —$CH_2CH_2$—.

In at least one embodiment, $R^{10}$ and $R^{11}$ are joined to form a six-membered ring with the joined $R^{10}R^{11}$ group being —$CH_2CH_2CH_2$—.

$R^1$ and $R^{13}$ may be independently selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment, the QDA transition metal complex represented by the Formula (BII) above where:

M is a group 4 metal (such hafnium);

E is selected from carbon, silicon, or germanium (such as carbon);

X is an alkyl, aryl, hydride, alkylsilane, fluoride, chloride, bromide, iodide, triflate, carboxylate, amido, alkoxo, or alkylsulfonate;

L is an ether, amine, or thioether;

$R^1$ and $R^{13}$ are independently selected from the group consisting of hydrocarbyls, substituted hydrocarbyls, and silyl groups (such as aryl);

$R^2$, $R^3$, $R^4$, $R^5$, $R^6$, $R^7$, $R^8$, $R^9$, $R^{10}$, $R^{11}$, and $R^{12}$ are independently hydrogen, hydrocarbyl, alkoxy, silyl, amino, aryloxy, substituted hydrocarbyls, halogen, and phosphino;

n is 1 or 2;

m is 0, 1, or 2;

n+m is from 1 to 4;

two X groups may be joined together to form a dianionic group;

two L groups may be joined together to form a bidentate Lewis base;

an X group may be joined to an L group to form a monoanionic bidentate group;

$R^7$ and $R^8$ may be joined to form a ring (such as an aromatic ring, a six-membered aromatic ring with the joined $R^7R^8$ group being —CH=CHCH=CH—); and $R^{10}$ and $R^{11}$ may be joined to form a ring (such as a five-membered ring with the joined $R^{10}R^{11}$ group being —$CH_2CH_2$—, a six-membered ring with the joined $R^{10}R^{11}$ group being —$CH_2CH_2CH_2$—).

In at least one embodiment of Formula (BI), (BII), and (BIII), $R^4$, $R^5$, and $R^6$ are independently selected from the group including hydrogen, hydrocarbyls, substituted hydrocarbyls, alkoxy, aryloxy, halogen, amino, and silyl, and wherein adjacent R groups ($R^4$ and $R^5$ and/or $R^5$ and $R^6$) are joined to form a substituted hydrocarbyl, unsubstituted hydrocarbyl, unsubstituted heterocyclic ring or substituted heterocyclic ring, where the ring has 5, 6, 7, or 8 ring atoms and where substitutions on the ring can join to form additional rings.

In at least one embodiment of Formula (BI), (BII), and (BIII), $R^7$, $R^8$, $R^9$, and $R^{10}$ are independently selected from the group including hydrogen, hydrocarbyls, substituted hydrocarbyls, alkoxy, halogen, amino, and silyl, and wherein adjacent R groups ($R^7$ and $R^8$ and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

In at least one embodiment of Formula (BI), (BII), and (BIII), $R^2$ and $R^3$ are each, independently, selected from the group including hydrogen, hydrocarbyls, and substituted hydrocarbyls, alkoxy, silyl, amino, aryloxy, halogen, and phosphino, $R^2$ and $R^3$ may be joined to form a saturated, substituted or unsubstituted hydrocarbyl ring, where the ring has 4, 5, 6, or 7 ring carbon atoms and where substitutions on the ring can join to form additional rings, or $R^2$ and $R^3$ may be joined to form a saturated heterocyclic ring, or a saturated substituted heterocyclic ring where substitutions on the ring can join to form additional rings.

In at least one embodiment of Formula (BI), (BII), and (BIII), $R^{11}$ and $R^{12}$ are each, independently, selected from the group including hydrogen, hydrocarbyls, and substituted hydrocarbyls, alkoxy, silyl, amino, aryloxy, halogen, and phosphino, $R^{11}$ and $R^{12}$ may be joined to form a saturated, substituted or unsubstituted hydrocarbyl ring, where the ring has 4, 5, 6, or 7 ring carbon atoms and where substitutions on the ring can join to form additional rings, or $R^1$ and $R^{12}$ may be joined to form a saturated heterocyclic ring, or a saturated substituted heterocyclic ring where substitutions on the ring can join to form additional rings, or $R^{11}$ and $R^{10}$ may be joined to form a saturated heterocyclic ring, or a saturated substituted heterocyclic ring where substitutions on the ring can join to form additional rings.

In at least one embodiment of Formula (BI), (BII), and (BIII), $R^1$ and $R^{13}$ are independently selected from phenyl groups that are variously substituted with between zero to five substituents that include F, Cl, Br, I, $CF_3$, $NO_2$, alkoxy, dialkylamino, aryl, and alkyl groups having 1 to 10 carbons, such as methyl, ethyl, propyl, butyl, pentyl, hexyl, heptyl, octyl, nonyl, decyl, and isomers thereof.

In at least one embodiment of Formula (BII), suitable $R^{12}$-E-$R^{11}$ groups include $CH_2$, $CMe_2$, $SiMe_2$, $SiEt_2$, $SiPr_2$, $SiBu_2$, $SiPh_2$, $Si(aryl)_2$, $Si(alkyl)_2$, CH(aryl), CH(Ph), CH(alkyl), and CH(2-isopropylphenyl), where alkyl is a $C_1$ to $C_{40}$ alkyl group (such as $C_1$ to $C_{20}$ alkyl, such as one or more of methyl, ethyl, propyl, butyl, pentyl, hexyl, heptyl, octyl, nonyl, decyl, undecyl, dodecyl, and isomers thereof), aryl is a $C_5$ to $C_{40}$ aryl group (such as a $C_6$ to $C_{20}$ aryl group, such as phenyl or substituted phenyl, such as phenyl, 2-isopropylphenyl, or 2-tertbutylphenyl).

In at least one embodiment of Formula (BIII), $R^{11}$, $R^{12}$, $R^9$, $R^{14}$, and $R^{10}$ are independently selected from the group consisting of hydrogen, hydrocarbyls, substituted hydrocarbyls, alkoxy, halogen, amino, and silyl, and wherein adjacent R groups ($R^{10}$ and $R^{14}$ and/or $R^{11}$ and $R^{14}$, and/or $R^9$ and $R^{10}$) may be joined to form a saturated, substituted hydrocarbyl, unsubstituted hydrocarbyl, unsubstituted heterocyclic ring or substituted heterocyclic ring, where the ring has 5, 6, 7, or 8 ring carbon atoms and where substitutions on the ring can join to form additional rings.

The R groups above (i.e., any of $R^2$ to $R^{14}$) and other R groups mentioned hereafter may contain from 1 to 30, such as 2 to 20 carbon atoms, such as from 6 to 20 carbon atoms. The R groups above (i.e., any of $R^2$ to $R^{14}$) and other R groups mentioned hereafter, may be independently selected from the group including hydrogen, methyl, ethyl, phenyl, isopropyl, isobutyl, trimethylsilyl, and —$CH_2$—$Si(Me)_3$.

In at least one embodiment, the quinolinyldiamide complex is linked to one or more additional transition metal complex, such as a quinolinyldiamide complex or another suitable non-metallocene, through an R group in such a fashion as to make a bimetallic, trimetallic, or multimetallic complex that may be used as a catalyst component for olefin polymerization. The linker R-group in such a complex may contain 1 to 30 carbon atoms.

In at least one embodiment, E is carbon and $R^{11}$ and $R^{12}$ are independently selected from phenyl groups that are substituted with 0, 1, 2, 3, 4, or 5 substituents selected from the group consisting of F, Cl, Br, I, $CF_3$, $NO_2$, alkoxy, dialkylamino, hydrocarbyl, and substituted hydrocarbyl groups with from one to ten carbons.

In at least one embodiment of Formula (BII) or (BIII), $R^{11}$ and $R^{12}$ are independently selected from hydrogen, methyl, ethyl, phenyl, isopropyl, isobutyl, —$CH_2$—$Si(Me)_3$, and trimethylsilyl.

In at least one embodiment of Formula (BII), and (BIII), R, $R^8$, $R^9$, and $R^{10}$ are independently selected from hydrogen, methyl, ethyl, propyl, isopropyl, phenyl, cyclohexyl, fluoro, chloro, methoxy, ethoxy, phenoxy, —$CH_2$—$Si(Me)_3$, and trimethylsilyl.

In at least one embodiment of Formula (BI), (BII), and (BIII), $R^2$, $R^3$, $R^4$, $R^5$, and $R^6$ are independently selected from the group consisting of hydrogen, hydrocarbyls, alkoxy, silyl, amino, substituted hydrocarbyls, and halogen.

In at least one embodiment of Formula (BIII), $R^{10}$, $R^{11}$ and $R^{14}$ are independently selected from hydrogen, methyl, ethyl, phenyl, isopropyl, isobutyl, —$CH_2$—$Si(Me)_3$, and trimethylsilyl.

In at least one embodiment of Formula (BI), (BII), and (BIII), each L is independently selected from $Et_2O$, MeOtBu, $Et_3N$, $PhNMe_2$, $MePh_2N$, tetrahydrofuran, and dimethylsulfide.

In at least one embodiment of Formula (BI), (BII), and (BIII), each X is independently selected from methyl, benzyl, trimethylsilyl, neopentyl, ethyl, propyl, butyl, phenyl, hydrido, chloro, fluoro, bromo, iodo, dimethylamido, diethylamido, dipropylamido, and diisopropylamido.

In at least one embodiment of Formula (BI), (BII), and (BIII), $R^1$ is 2,6-diisopropylphenyl, 2,4,6-triisopropylphenyl, 2,6-diisopropyl-4-methylphenyl, 2,6-diethylphenyl, 2-ethyl-6-isopropylphenyl, 2,6-bis(3-pentyl)phenyl, 2,6-dicyclopentylphenyl, or 2,6-dicyclohexylphenyl.

In at least one embodiment of Formula (BI), (BII), and (BIII), $R^{13}$ is phenyl, 2-methylphenyl, 2-ethylphenyl, 2-propylphenyl, 2,6-dimethylphenyl, 2-isopropylphenyl, 4-methylphenyl, 3,5-dimethylphenyl, 3,5-di-tert-butylphenyl, 4-fluorophenyl, 3-methylphenyl, 4-dimethylaminophenyl, or 2-phenylphenyl.

In at least one embodiment of Formula (BII), J is dihydro-1H-indenyl and $R^1$ is 2,6-dialkylphenyl or 2,4,6-trialkylphenyl.

In at least one embodiment of Formula (BI), (BII), and (BIII), $R^1$ is 2,6-diisopropylphenyl and $R^{13}$ is a hydrocarbyl group containing 1, 2, 3, 4, 5, 6, or 7 carbon atoms.

An exemplary catalyst used for polymerizations of the present disclosure is (QDA-1)$HfMe_2$, as described in US Pub. No. 2018/0002352 A1.

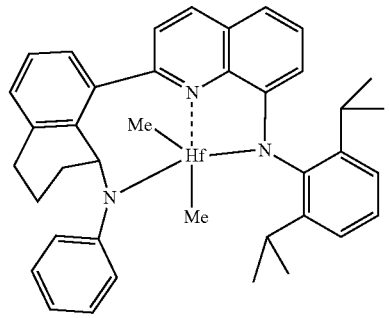

(QDA-1)$HfMe_2$

In at least one embodiment, the catalyst compound is a bis(phenolate) catalyst compound represented by Formula (CI):

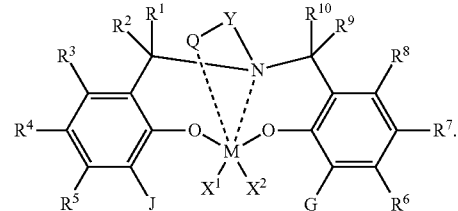

(CI)

M is a Group 4 metal, such as Hf or Zr. $X^1$ and $X^2$ are independently a univalent $C_1$-$C_{20}$ hydrocarbyl, $C_1$-$C_{20}$ substituted hydrocarbyl, a heteroatom or a heteroatom-containing group, or $X^1$ and $X^2$ join together to form a $C_4$-$C_{62}$ cyclic or polycyclic ring structure. $R^1$, $R^2$, $R^3$, $R^4$, $R^5$, $R^6$, $R^7$, $R^8$, $R^9$, and $R^{10}$ is independently hydrogen, $C_1$-$C_{40}$ hydrocarbyl, $C_1$-$C_{40}$ substituted hydrocarbyl, a heteroatom or a heteroatom-containing group, or two or more of $R^1$, $R^2$, $R^3$, $R^4$, $R^5$, $R^6$, $R^7$, $R^8$, $R^9$, or $R^{10}$ are joined together to form a $C_4$-$C_{62}$ cyclic or polycyclic ring structure, or a combination thereof, Q is a neutral donor group; J is heterocycle, a substituted or unsubstituted $C_7$-$C_{60}$ fused polycyclic group, where at least one ring is aromatic and where at least one ring, which may or may not be aromatic, has at least five ring atoms' G is as defined for J or may be hydrogen, $C_2$-$C_{60}$ hydrocarbyl, $C_1$-$C_{60}$ substituted hydrocarbyl, or may independently form a $C_4$-$C_{60}$ cyclic or polycyclic ring structure with $R^6$, $R^7$, or $R^8$ or a combination thereof, Y is divalent $C_1$-$C_{20}$ hydrocarbyl or divalent $C_1$-$C_{20}$ substituted hydrocarbyl or (-Q*-Y—) together form a heterocycle; and heterocycle may be aromatic and/or may have multiple fused rings.

In at least one embodiment, the catalyst compound represented by Formula (CI) is represented by Formula (CII) or Formula (CIII):

(CII)

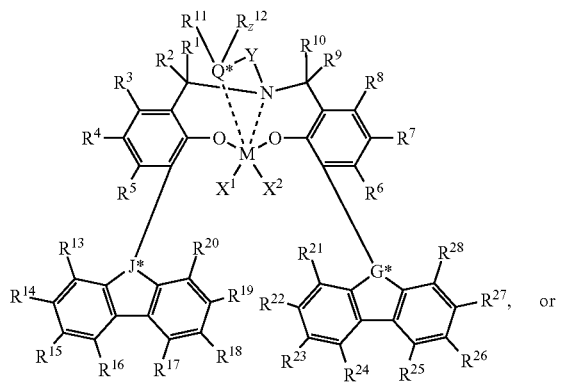

(IV)

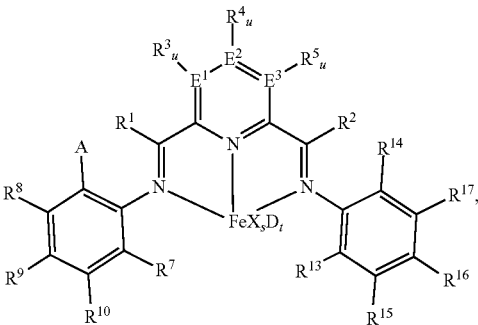

(CIII)

M is Hf, Zr, or Ti. $X^1$, $X^2$, $R^1$, $R^2$, $R^3$, $R^4$, $R^5$, $R^6$, $R^7$, $R^8$, $R^9$, $R^{10}$, and Y are as defined for Formula (CI). $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ is independently a hydrogen, $C_1$-$C_{40}$ hydrocarbyl, $C_1$-$C_{40}$ substituted hydrocarbyl, a functional group comprising elements from Groups 13 to 17, or two or more of $R^1$, $R^2$, $R^3$, $R^4$, $R^5$, $R^6$, $R^7$, $R^8$, $R^9$, $R^{10}$ $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, and $R^{28}$ may independently join together to form a $C_4$-$C_{62}$ cyclic or polycyclic ring structure, or a combination thereof; $R^{11}$ and $R^{12}$ may join together to form a five- to eight-membered heterocycle;

Q* is a group 15 or 16 atom; z is 0 or 1;

J* is CR" or N, and G* is CR" or N, where R" is $C_1$-$C_{20}$ hydrocarbyl or carbonyl-containing $C_1$-$C_{20}$ hydrocarbyl; and z=0 if Q* is a group 16 atom, and z=1 if Q* is a group 15 atom.

In at least one embodiment the catalyst is an iron complex represented by formula (IV):

wherein:

A is chlorine, bromine, iodine, —$CF_3$ or —$OR^{11}$;

each of $R^1$ and $R^2$ is independently hydrogen, $C_1$-$C_{22}$-alkyl, $C_2$-$C_{22}$-alkenyl, $C_6$-$C_{22}$-aryl, arylalkyl where alkyl has from 1 to 10 carbon atoms and aryl has from 6 to 20 carbon atoms, or five-, six- or seven-membered heterocyclyl comprising at least one atom selected from the group consisting of N, P, O and S;

wherein each of $R^1$ and $R^2$ is optionally substituted by halogen, —$NR^{11}_2$, —$OR^{11}$ or —$SiR^{12}_3$;

wherein $R^1$ optionally bonds with $R^3$, and $R^2$ optionally bonds with $R^5$, in each case to independently form a five-, six- or seven-membered ring;

$R^7$ is a $C_1$-$C_{20}$ alkyl;

each of $R^3$, $R^4$, $R^5$, $R^8$, $R^9$, $R^{10}$, $R^{15}$, $R^{16}$, and $R^{17}$ is independently hydrogen, $C_1$-$C_{22}$-alkyl, $C_2$-$C_{22}$-alkenyl, $C_6$-$C_{22}$-aryl, arylalkyl where alkyl has from 1 to 10 carbon atoms and aryl has from 6 to 20 carbon atoms, —$NR^{11}_2$, —$OR^{11}$, halogen, —$SiR^{12}_3$ or five-, six- or seven-membered heterocyclyl comprising at least one atom selected from the group consisting of N, P, O, and S;

wherein $R^3$, $R^4$, $R^5$, $R^7$, $R^8$, $R^9$, $R^{10}$, $R^{15}$, $R^{16}$, and $R^{17}$ are optionally substituted by halogen, —$NR^{11}_2$, —$OR^{11}$ or —$SiR^{12}_3$;

wherein $R^3$ optionally bonds with $R^4$, $R^4$ optionally bonds with $R^5$, $R^7$ optionally bonds with $R^{10}$, $R^{10}$ optionally bonds with $R^9$, $R^9$ optionally bonds with $R^8$, $R^{17}$ optionally bonds with $R^{16}$, and $R^{16}$ optionally bonds with $R^{15}$, in each case to independently form a five-, six- or seven-membered carbocyclic or heterocyclic ring, the heterocyclic ring comprising at least one atom from the group consisting of N, P, O and S;

$R^{13}$ is $C_1$-$C_{20}$-alkyl bonded with the aryl ring via a primary or secondary carbon atom;

$R^{14}$ is chlorine, bromine, iodine, —$CF_3$ or —$OR^{11}$, or $C_1$-$C_{20}$-alkyl bonded with the aryl ring;

each $R^{11}$ is independently hydrogen, $C_1$-$C_{22}$-alkyl, $C_2$-$C_{22}$-alkenyl, $C_6$-$C_{22}$-aryl, arylalkyl where alkyl has from 1 to 10 carbon atoms and aryl has from 6 to 20 carbon atoms, or —$SiR^{12}_3$, wherein $R^{11}$ is optionally substituted by halogen, or two $R^{11}$ radicals optionally bond to form a five- or six-membered ring;

each $R^{12}$ is independently hydrogen, $C_1$-$C_{22}$-alkyl, $C_2$-$C_{22}$-alkenyl, $C_6$-$C_{22}$-aryl, arylalkyl where alkyl has from 1 to 10 carbon atoms and aryl has from 6 to 20 carbon atoms, or two $R^{12}$ radicals optionally bond to form a five- or six-membered ring;

each of $E^1$, $E^2$, and $E^3$ is independently carbon, nitrogen or phosphorus;

each u is independently 0 if $E^1$, $E^2$, and $E^3$ is nitrogen or phosphorus and is 1 if $E^1$, $E^2$, and $E^3$ is carbon;

each X is independently fluorine, chlorine, bromine, iodine, hydrogen, $C_1$-$C_{20}$-alkyl, $C_2$-$C_{10}$-alkenyl, $C_6$-$C_{20}$-aryl, arylalkyl where alkyl has from 1 to 10 carbon atoms and aryl has from 6 to 20 carbon atoms, —$NR^{18}{}_2$, —OR", —SR", —$SO_3R^{18}$, —$OC(O)R^{18}$, —CN, —SCN, 1-diketonate, —CO, —$BF_4$—, —$PF_6$ or bulky non-coordinating anions, and the radicals X can be bonded with one another;

each $R^{18}$ is independently hydrogen, $C_1$-$C_{20}$-alkyl, $C_2$-$C_{20}$-alkenyl, $C_6$-$C_{20}$-aryl, arylalkyl where alkyl has from 1 to 10 carbon atoms and aryl has from 6 to 20 carbon atoms, or —$SiR^{19}{}_3$, wherein $R^{18}$ can be substituted by halogen or nitrogen- or oxygen-containing groups and two $R^{18}$ radicals optionally bond to form a five- or six-membered ring;

each $R^{19}$ is independently hydrogen, $C_1$-$C_{20}$-alkyl, $C_2$-$C_{20}$-alkenyl, $C_6$-$C_{20}$-aryl or arylalkyl where alkyl has from 1 to 10 carbon atoms and aryl has from 6 to 20 carbon atoms, wherein $R^{19}$ can be substituted by halogen or nitrogen- or oxygen-containing groups or two $R^{19}$ radicals optionally bond to form a five- or six-membered ring;

s is 1, 2, or 3;

D is a neutral donor; and t is 0 to 2.

In another embodiment, the catalyst is a phenoxyimine compound represented by the formula (VII):

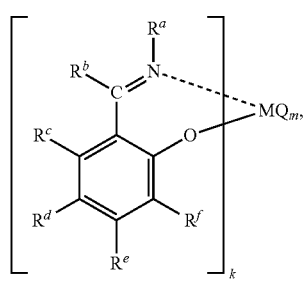

wherein M represents a transition metal atom selected from the groups 3 to 11 metals in the periodic table; k is an integer of 1 to 6; m is an integer of 1 to 6; $R^a$ to $R^f$ may be the same or different from one another and each represent a hydrogen atom, a halogen atom, a hydrocarbon group, a heterocyclic compound residue, an oxygen-containing group, a nitrogen-containing group, a boron-containing group, a sulfur-containing group, a phosphorus-containing group, a silicon-containing group, a germanium-containing group or a tin-containing group, among which 2 or more groups may be bound to each other to form a ring; when k is 2 or more, $R^a$ groups, $R^b$ groups, $R^c$ groups, $R^d$ groups, $R^e$ groups, or $R^f$ groups may be the same or different from one another, one group of $R^a$ to $R^f$ contained in one ligand and one group of $R^a$ to $R^f$ contained in another ligand may form a linking group or a single bond, and a heteroatom contained in $R^a$ to $R^f$ may coordinate with or bind to M; m is a number satisfying the valence of M; Q represents a hydrogen atom, a halogen atom, an oxygen atom, a hydrocarbon group, an oxygen-containing group, a sulfur-containing group, a nitrogen-containing group, a boron-containing group, an aluminum-containing group, a phosphorus-containing group, a halogen-containing group, a heterocyclic compound residue, a silicon-containing group, a germanium-containing group or a tin-containing group; when m is 2 or more, a plurality of groups represented by Q may be the same or different from one another, and a plurality of groups represented by Q may be mutually bound to form a ring.

In another embodiment, the catalyst is a bis(imino)pyridyl of the formula (VIII):

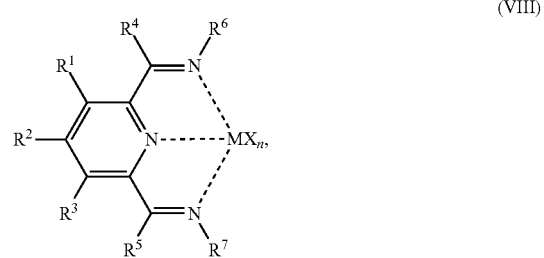

wherein:

M is Co or Fe; each X is an anion; n is 1, 2 or 3, so that the total number of negative charges on said anion or anions is equal to the oxidation state of a Fe or Co atom present in (VIII);

$R^1$, $R^2$ and $R^3$ are each independently hydrogen, hydrocarbyl, substituted hydrocarbyl, or an inert functional group;

$R^4$ and $R^5$ are each independently hydrogen, hydrocarbyl, an inert functional group or substituted hydrocarbyl;

$R^6$ is formula (IX):

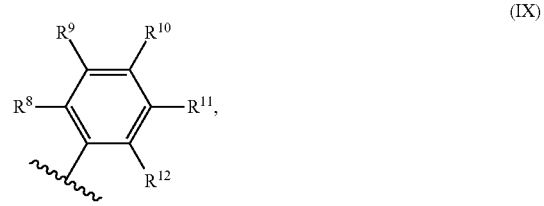

and $R^7$ is formula (X):

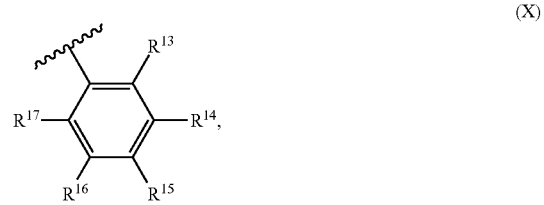

$R^8$ and $R^{13}$ are each independently hydrocarbyl, substituted hydrocarbyl or an inert functional group;

$R^9$, $R^{10}$, $R^{11}$, $R^{14}$, $R^{15}$ and $R^{16}$ are each independently hydrogen, hydrocarbyl, substituted hydrocarbyl or an inert functional group;

$R^{12}$ and $R^{17}$ are each independently hydrogen, hydrocarbyl, substituted hydrocarbyl or an inert functional group;

and provided that any two of $R^8$, $R^9$, $R^{10}$, $R^{11}$, $R^{12}$, $R^{13}$, $R^{14}$, $R^{15}$, $R^{16}$ and $R^{17}$ that are adjacent to one another, together may form a ring.

In at least one embodiment, the catalyst compound is represented by the formula (XI):

(XI)

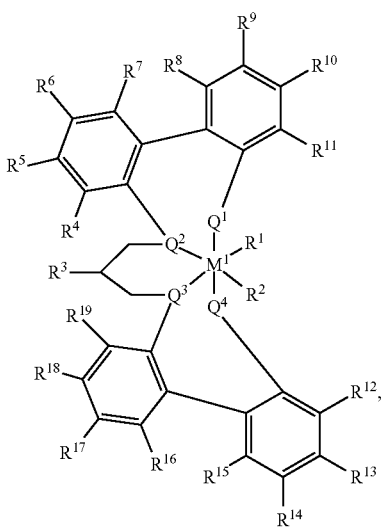

$M^1$ is selected from the group consisting of titanium, zirconium, hafnium, vanadium, niobium, tantalum, chromium, molybdenum and tungsten. In at least one embodiment, $M^1$ is zirconium.

Each of $Q^1$, $Q^2$, $Q^3$, and $Q^4$ is independently oxygen or sulfur. In at least one embodiment, at least one of $Q^1$, $Q^2$, $Q^3$, and $Q^4$ is oxygen, alternately all of $Q^1$, $Q^2$, $Q^3$, and $Q^4$ are oxygen.

$R^1$ and $R^2$ are independently hydrogen, halogen, hydroxyl, hydrocarbyl, or substituted hydrocarbyl (such as $C_1$-$C_{10}$ alkyl, $C_1$-$C_{10}$ alkoxy, $C_6$-$C_{20}$ aryl, $C_6$-$C_{10}$ aryloxy, $C_2$-$C_{10}$ alkenyl, $C_2$-$C_{40}$ alkenyl, $C_7$-$C_{40}$ arylalkyl, $C_7$-$C_{40}$ alkylaryl, $C_8$-$C_{40}$ arylalkenyl, or conjugated diene which is optionally substituted with one or more hydrocarbyl, tri(hydrocarbyl) silyl or tri(hydrocarbyl) silylhydrocarbyl, the diene having up to 30 atoms other than hydrogen). $R^1$ and $R^2$ can be a halogen selected from fluorine, chlorine, bromine, or iodine. Preferably, $R^1$ and $R^2$ are chlorine.

Alternatively, $R^1$ and $R^2$ may also be joined together to form an alkanediyl group or a conjugated $C_4$-$C_{40}$ diene ligand which is coordinated to $M^1$. $R^1$ and $R^2$ may also be identical or different conjugated dienes, optionally substituted with one or more hydrocarbyl, tri(hydrocarbyl) silyl or tri(hydrocarbyl) silylhydrocarbyl, the dienes having up to 30 atoms not counting hydrogen and/or forming a in-complex with $M^1$.

Exemplary groups suitable for $R^1$ and or $R^2$ can include 1,4-diphenyl, 1,3-butadiene, 1,3-pentadiene, 2-methyl 1,3-pentadiene, 2,4-hexadiene, 1-phenyl, 1,3-pentadiene, 1,4-dibenzyl, 1,3-butadiene, 1,4-ditolyl-1,3-butadiene, 1,4-bis(trimethylsilyl)-1,3-butadiene, and 1,4-dinaphthyl-1,3-butadiene. $R^1$ and $R^2$ can be identical and are $C_1$-$C_3$ alkyl or alkoxy, $C_6$-$C_{10}$ aryl or aryloxy, $C_2$-$C_4$ alkenyl, $C_7$-$C_{10}$ arylalkyl, $C_7$-$C_{12}$ alkylaryl, or halogen.

Each of $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, and $R^{19}$ is independently hydrogen, halogen, $C_1$-$C_{40}$ hydrocarbyl or $C_1$-$C_{40}$ substituted hydrocarbyl (such as $C_1$-$C_{10}$ alkyl, $C_1$-$C_{10}$ alkoxy, $C_6$-$C_{20}$ aryl, $C_6$-$C_{10}$ aryloxy, $C_2$-$C_{10}$ alkenyl, $C_2$-$C_{40}$ alkenyl, $C_7$-$C_{40}$ arylalkyl, $C_7$-$C_{40}$ alkylaryl, $C_8$-$C_{40}$ arylalkenyl, or conjugated diene which is optionally substituted with one or more hydrocarbyl, tri(hydrocarbyl) silyl or tri(hydrocarbyl) silylhydrocarbyl, the diene having up to 30 atoms other than hydrogen), —$NR'_2$, —$SR'$, —$OR$, —$OSiR'_3$, —$PR'_2$, where each R' is hydrogen, halogen, $C_1$-$C_{10}$ alkyl, or $C_6$-$C_{10}$ aryl, or one or more of $R^4$ and $R^5$, $R^5$ and $R^6$, $R^6$ and $R^7$, $R^8$ and $R^9$, $R^9$ and $R^{10}$, $R^{10}$ and $R^{11}$, $R^{12}$ and $R^{13}$, $R^{13}$ and $R^{14}$, $R^{14}$ and $R^{15}$, $R^{16}$ and $R^{17}$, $R^{17}$ and $R^{18}$, and $R^{18}$ and $R^{19}$ are joined to form a saturated ring, unsaturated ring, substituted saturated ring, or substituted unsaturated ring. In at least one embodiment, $C_1$-$C_{40}$ hydrocarbyl is selected from methyl, ethyl, propyl, n-propyl, isopropyl, n-butyl, isobutyl, sec-butyl, n-pentyl, isopentyl, sec-pentyl, n-hexyl, isohexyl, sec-hexyl, n-heptyl, isoheptyl, sec-heptyl, n-octyl, isooctyl, sec-octyl, n-nonyl, isononyl, sec-nonyl, n-decyl, isodecyl, and sec-decyl. Preferably, $R^{11}$ and $R^{12}$ are $C_6$-$C_{10}$ aryl such as phenyl or naphthyl optionally substituted with $C_1$-$C_{40}$ hydrocarbyl, such as $C_1$-$C_{10}$ hydrocarbyl. Preferably, $R^6$ and $R^{17}$ are $C_{1-40}$ alkyl, such as $C_1$-$C_{10}$ alkyl.

In at least one embodiment, each of $R^4$, $R^5$, $R^6$, $R^7$, $R^8$, $R^9$, $R^{10}$, $R^{13}$, $R^{14}$, $R^{15}$, $R^{16}$, $R^{17}$, $R^{18}$, and $R^{19}$ is independently hydrogen or $C_1$-$C_{40}$ hydrocarbyl. In at least one embodiment, $C_1$-$C_{40}$ hydrocarbyl is selected from methyl, ethyl, propyl, n-propyl, isopropyl, n-butyl, isobutyl, sec-butyl, n-pentyl, isopentyl, sec-pentyl, n-hexyl, isohexyl, sec-hexyl, n-heptyl, isoheptyl, sec-heptyl, n-octyl, isooctyl, sec-octyl, n-nonyl, isononyl, sec-nonyl, n-decyl, isodecyl, and sec-decyl. Preferably, each of $R^6$ and $R^{17}$ is $C_1$-$C_{40}$ hydrocarbyl and $R^4$, $R^5$, $R^7$, $R^8$, $R^9$, $R^{10}$, $R^{13}$, $R^{14}$, $R^{15}$, $R^{16}$, $R^{18}$, and $R^{19}$ is hydrogen. In at least one embodiment, $C_1$-$C_{40}$ hydrocarbyl is selected from methyl, ethyl, propyl, n-propyl, isopropyl, n-butyl, isobutyl, sec-butyl, n-pentyl, isopentyl, sec-pentyl, n-hexyl, isohexyl, sec-hexyl, n-heptyl, isoheptyl, sec-heptyl, n-octyl, isooctyl, sec-octyl, n-nonyl, isononyl, sec-nonyl, n-decyl, isodecyl, and sec-decyl.

$R^3$ is a $C_1$-$C_{40}$ unsaturated alkyl or substituted $C_1$-$C_{40}$ unsaturated alkyl (such as $C_1$-$C_{10}$ alkyl, $C_1$-$C_{10}$ alkoxy, $C_6$-$C_{20}$ aryl, $C_6$-$C_{10}$ aryloxy, $C_2$-$C_{10}$ alkenyl, $C_2$-$C_{40}$ alkenyl, $C_7$-$C_{40}$ arylalkyl, $C_8$-$C_{40}$ arylalkenyl, or conjugated diene which is optionally substituted with one or more hydrocarbyl, tri(hydrocarbyl) silyl or tri(hydrocarbyl) silylhydrocarbyl, the diene having up to 30 atoms other than hydrogen).

Preferably, $R^3$ is a hydrocarbyl comprising a vinyl moiety. As used herein, "vinyl" and "vinyl moiety" are used interchangeably and include a terminal alkene, e.g., represented by the structure

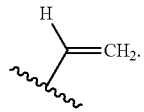

Hydrocarbyl of $R^3$ may be further substituted (such as $C_1$-$C_{10}$ alkyl, $C_1$-$C_{10}$ alkoxy, $C_6$-$C_{20}$ aryl, $C_6$-$C_{10}$ aryloxy, $C_2$-$C_{10}$ alkenyl, $C_2$-$C_{40}$ alkenyl, $C_7$-$C_{40}$ arylalkyl, $C_7$-$C_{40}$ alkylaryl, $C_5$-$C_{40}$ arylalkenyl, or conjugated diene which is optionally substituted with one or more hydrocarbyl, tri(hydrocarbyl) silyl or tri(hydrocarbyl) silylhydrocarbyl, the diene having up to 30 atoms other than hydrogen). Preferably, $R^3$ is $C_1$-$C_{40}$ unsaturated alkyl that is vinyl or substituted $C_1$-$C_{40}$ unsaturated alkyl that is vinyl. $R^3$ can be represented by the structure —$R'CH=CH_2$ where R' is $C_1$-$C_{40}$ hydrocarbyl or $C_1$-$C_{40}$ substituted hydrocarbyl (such as $C_1$-$C_{10}$ alkyl, $C_1$-$C_{10}$ alkoxy, $C_6$-$C_{20}$ aryl, $C_6$-$C_{10}$ aryloxy, $C_2$-$C_{10}$ alkenyl, $C_2$-$C_{40}$ alkenyl, $C_7$-$C_{40}$ arylalkyl, $C_8$-$C_{40}$ arylalkenyl, or conjugated diene which is optionally substituted with one or more hydrocarbyl, tri(hydrocarbyl) silyl or tri(hydrocarbyl) silylhydrocarbyl, the diene having up to 30 atoms other than hydrogen). In at least one embodiment, $C_1$-$C_{40}$ hydrocarbyl is selected from methyl, ethyl, propyl, n-propyl, isopropyl, n-butyl, isobutyl, sec-butyl, n-pentyl, isopentyl, sec-pentyl, n-hexyl, isohexyl, sec-hexyl, n-heptyl, isoheptyl, sec-heptyl, n-octyl, isooctyl, sec-octyl, n-nonyl, isononyl, sec-nonyl, n-decyl, isodecyl, and sec-decyl.

In at least one embodiment, $R^3$ is 1-propenyl, 1-butenyl, 1-pentenyl, 1-hexenyl, 1-heptenyl, 1-octenyl, 1-nonenyl, or 1-decenyl.

In at least one embodiment, the catalyst is a Group 15-containing metal compound represented by Formulas (XII) or (XIII):

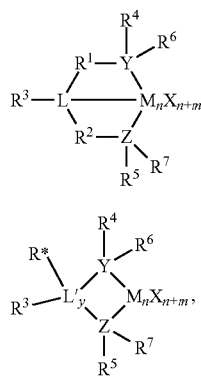

wherein M is a Group 3 to 12 transition metal or a Group 13 or 14 main group metal, a Group 4, 5, or 6 metal. In many embodiments, M is a Group 4 metal, such as zirconium, titanium, or hafnium. Each X is independently a leaving group, such as an anionic leaving group. The leaving group may include a hydrogen, a hydrocarbyl group, a heteroatom, a halogen, or an alkyl; y is 0 or 1 (when y is 0 group L' is absent). The term 'n' is the oxidation state of M. In various embodiments, n is +3, +4, or +5. In many embodiments, n is +4. The term 'm' represents the formal charge of the YZL or the YZL' ligand, and is 0, −1, −2 or −3 in various embodiments. In many embodiments, m is −2. L is a Group 15 or 16 element, such as nitrogen or oxygen; L' is a Group 15 or 16 element or Group 14 containing group, such as carbon, silicon or germanium. Y is a Group 15 element, such as nitrogen or phosphorus. In many embodiments, Y is nitrogen. Z is a Group 15 element, such as nitrogen or phosphorus. In many embodiments, Z is nitrogen. $R^1$ and $R^2$ are, independently, a $C_1$ to $C_{20}$ hydrocarbon group, a heteroatom containing group having up to twenty carbon atoms, silicon, germanium, tin, lead, or phosphorus. In many embodiments, $R^1$ and $R^2$ are a $C_2$ to $C_{20}$ alkyl, aryl or aralkyl group, such as a $C_2$ to $C_{20}$ linear, branched or cyclic alkyl group, or a $C_2$ to $C_{20}$ hydrocarbon group. $R^1$ and $R^2$ may also be interconnected to each other. $R^3$ may be absent or may be a hydrocarbon group, a hydrogen, a halogen, a heteroatom containing group. In many embodiments, $R^3$ is absent, for example, if L is an oxygen, or a hydrogen, or a linear, cyclic, or branched alkyl group having 1 to 20 carbon atoms. $R^4$ and $R^5$ are independently an alkyl group, an aryl group, substituted aryl group, a cyclic alkyl group, a substituted cyclic alkyl group, a cyclic aralkyl group, a substituted cyclic aralkyl group, or multiple ring system, often having up to 20 carbon atoms. In many embodiments, $R^4$ and $R^5$ have between 3 and 10 carbon atoms, or are a $C_1$ to $C_{20}$ hydrocarbon group, a $C_1$ to $C_{20}$ aryl group or a $C_1$ to $C_{20}$ aralkyl group, or a heteroatom containing group. $R^4$ and $R^5$ may be interconnected to each other. $R^6$ and $R^7$ are independently absent, hydrogen, an alkyl group, halogen, heteroatom, or a hydrocarbyl group, such as a linear, cyclic or branched alkyl group having 1 to 20 carbon atoms. In many embodiments, $R^6$ and $R^7$ are absent. $R^*$ may be absent, or may be a hydrogen, a Group 14 atom containing group, a halogen, or a heteroatom containing group.

By "formal charge of the YZL or YZL' ligand," it is meant the charge of the entire ligand absent the metal and the leaving groups X. By "$R^1$ and $R^2$ may also be interconnected" it is meant that $R^1$ and $R^2$ may be directly bound to each other or may be bound to each other through other groups. By "$R^4$ and $R^5$ may also be interconnected" it is meant that $R^4$ and $R^5$ may be directly bound to each other or may be bound to each other through other groups. An alkyl group may be linear, branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals, straight, branched or cyclic, alkylene radicals, or combination thereof. An aralkyl group is defined to be a substituted aryl group.

In one or more embodiments, $R^4$ and $R^5$ are independently a group represented by structure (XIV):

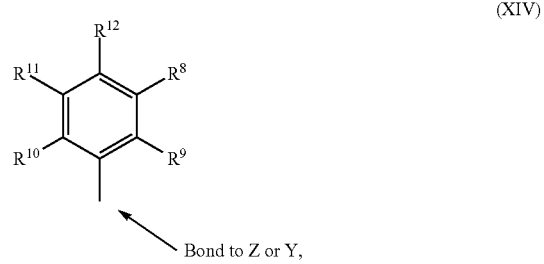

wherein $R^8$ to $R^{12}$ are each independently hydrogen, a $C_1$ to $C_{40}$ alkyl group, a halide, a heteroatom, a heteroatom containing group containing up to 40 carbon atoms. In many embodiments, $R^8$ to $R^{12}$ are a $C_1$ to $C_{20}$ linear or branched alkyl group, such as a methyl, ethyl, propyl, or butyl group. Any two of the R groups may form a cyclic group and/or a heterocyclic group. The cyclic groups may be aromatic. In one embodiment $R^9$, $R^{10}$ and $R^{12}$ are independently a methyl, ethyl, propyl, or butyl group (including all isomers). In another embodiment, $R^9$, $R^{10}$ and $R^{12}$ are methyl groups, and $R^8$ and $R^{11}$ are hydrogen.

In one or more embodiments, $R^4$ and $R^5$ are both a group represented by structure (XV):

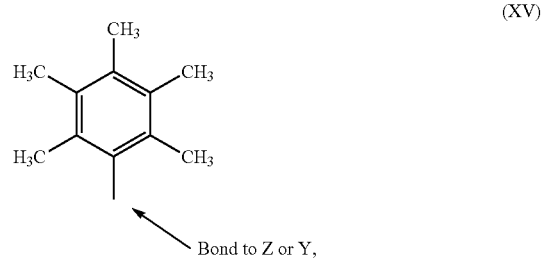

wherein M is a Group 4 metal, such as zirconium, titanium, or hafnium. In at least one embodiment, M is zirconium. Each of L, Y, and Z may be a nitrogen. Each of $R^1$ and $R^2$ may be —$CH_2$—$CH_2$—. $R^3$ may be hydrogen, and $R^6$ and $R^7$ may be absent.

In preferred embodiments, the catalyst compounds described in PCT/US2018/051345, filed Sep. 17, 2018 may be used with the activators described herein, particularly the catalyst compounds described at Page 16 to Page 32 of the application as filed.

In some embodiments, a co-activator is combined with the catalyst compound (such as halogenated catalyst compounds described above) to form an alkylated catalyst compound. Organoaluminum compounds which may be utilized as co-activators include, for example, trialkyl aluminum compounds, such as trimethylaluminum, triethylaluminum, triisobutylaluminum, tri-n-hexylaluminum, tri-n-octylaluminum, and the like, or alumoxanes.

In some embodiments, two or more different catalyst compounds are present in the catalyst system used herein. In some embodiments, two or more different catalyst compounds are present in the reaction zone where the process (es) described herein occur. When two transition metal compound based catalysts are used in one reactor as a mixed catalyst system, the two transition metal compounds are preferably chosen such that the two are compatible. A simple screening method such as by $^1H$ or $^{13}C$ NMR, known to those of ordinary skill in the art, can be used to determine which transition metal compounds are compatible. It is preferable to use the same activator for the transition metal compounds, however, two different activators can be used in combination. If one or more transition metal compounds contain an anionic ligand as a leaving group which is not a hydride, hydrocarbyl, or substituted hydrocarbyl, then the alumoxane or other alkyl aluminum is typically contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, and alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Support Materials

In embodiments herein, the catalyst system may comprise a support material. In at least one embodiment, the support material is a porous support material, for example, talc, or inorganic oxides. Other support materials include zeolites, clays, organoclays, or any other suitable organic or inorganic support material and the like, or mixtures thereof.

In at least one embodiment, the support material is an inorganic oxide. Suitable inorganic oxide materials for use in catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be used, for example, functionalized polyolefins, such as polypropylene. Supports include magnesia, titania, zirconia, montmorillonite, phyllosilicate, zeolites, talc, clays, and the like. Also, combinations of these support materials may be used, for example, silica-chromium, silica-alumina, silica-titania, and the like. Support materials include $Al_2O_3$, $ZrO_2$, $SiO_2$, $SiO_2/Al_2O_3$, $SiO_2/TiO_2$, silica clay, silicon oxide/clay, or mixtures thereof.

The support material, such as an inorganic oxide, can have a surface area of from 10 $m^2/g$ to 700 $m^2/g$, pore volume in the range of from 0.1 cc/g to 4.0 cc/g and average particle size in the range of from 5 μm to 500 μm. In at least one embodiment, the surface area of the support material is in the range of from 50 $m^2/g$ to 500 $m^2/g$, pore volume of from 0.5 cc/g to 3.5 cc/g and average particle size of from 10 μm to 200 μm. In at least one embodiment, the surface area of the support material is in the range is from 100 $m^2/g$ to 400 $m^2/g$, pore volume from 0.8 cc/g to 3.0 cc/g and average particle size is from 5 μm to 100 μm. The average pore size of the support material useful in the present disclosure is in the range of from 10 Å to 1000 Å, such as 50 Å to 500 Å, such as 75 Å to 350 Å. In some embodiments, the support material is a high surface area, amorphous silica (surface area=300 $m^2/gm$; pore volume of 1.65 $cm^3/gm$). Exemplary silicas are marketed under the tradenames of DAVISON 952 or DAVISON 955 by the Davison Chemical Division of W.R. Grace and Company. In other embodiments DAVISON 948 is used.

The support material should be dry, that is, substantially free of absorbed water. Drying of the support material can be effected by heating or calcining at 100° C. to 1,000° C., such as at least about 600° C. When the support material is silica, it is heated to at least 200° C., such as 200° C. to 850° C., such as at about 600° C.; and for a time of 1 minute to about 100 hours, from 12 hours to 72 hours, or from 24 hours to 60 hours. The calcined support material should have at least some reactive hydroxyl (OH) groups to produce supported catalyst systems of the present disclosure. The calcined support material is then contacted with at least one polymerization catalyst comprising at least one catalyst compound and an activator.

The support material, having reactive surface groups, typically hydroxyl groups, is slurried in a non-polar solvent and the resulting slurry is contacted with a solution of a catalyst compound and an activator. In some embodiments, the slurry of the support material is first contacted with the activator for a period of time in the range of from 0.5 hours to 24 hours, from 2 hours to 16 hours, or from 4 hours to 8 hours. The solution of the catalyst compound is then contacted with the isolated support/activator. In some embodiments, the supported catalyst system is generated in situ. In at least one embodiment, the slurry of the support material is first contacted with the catalyst compound for a period of time in the range of from 0.5 hours to 24 hours, from 2 hours to 16 hours, or from 4 hours to 8 hours. The slurry of the supported catalyst compound is then contacted with the activator solution.

The mixture of the catalyst, activator and support is heated to 0° C. to 70° C., such as to 23° C. to 60° C., such as at room temperature. Contact times typically range from 0.5 hours to 24 hours, from 2 hours to 16 hours, or from 4 hours to 8 hours.

Suitable non-polar solvents are materials in which all of the reactants used herein, e.g., the activator, and the catalyst compound, are at least partially soluble and which are liquid at room temperature. Non-limiting example non-polar solvents are alkanes, such as isopentane, hexane, n-heptane, octane, nonane, and decane, cycloalkanes, such as cyclohexane, aromatics, such as benzene, toluene, and ethylbenzene.

In at least one embodiment, the support material comprises a support material treated with an electron-withdrawing anion. The support material can be silica, alumina, silica-alumina, silica-zirconia, alumina-zirconia, aluminum phosphate, heteropolytungstates, titania, magnesia, boria, zinc oxide, mixed oxides thereof, or mixtures thereof; and the electron-withdrawing anion is selected from fluoride, chloride, bromide, phosphate, triflate, bisulfate, sulfate, or any combination thereof.

The electron-withdrawing component used to treat the support material can be any component that increases the Lewis or Brønsted acidity of the support material upon treatment (as compared to the support material that is not treated with at least one electron-withdrawing anion). In at least one embodiment, the electron-withdrawing component is an electron-withdrawing anion derived from a salt, an acid, or other compound, such as a volatile organic compound, that serves as a source or precursor for that anion. Electron-withdrawing anions can be sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or mixtures thereof, or combinations thereof. An electron-withdrawing anion can be fluoride, chloride, bromide, phosphate, triflate, bisulfate, or sulfate, or any combination thereof, at least one embodiment of this disclosure. In at least one embodiment, the electron-withdrawing anion is sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof.

Thus, for example, the support material suitable for use in the catalyst systems of the present disclosure can be one or more of fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, sulfated silica-coated alumina, phosphated silica-coated alumina, or combinations thereof. In at least one embodiment, the activator-support can be, or can comprise, fluorided alumina, sulfated alumina, fluorided silica-alumina, sulfated silica-alumina, fluorided silica-coated alumina, sulfated silica-coated alumina, phosphated silica-coated alumina, or combinations thereof. In another embodiment, the support material includes alumina treated with hexafluorotitanic acid, silica-coated alumina treated with hexafluorotitanic acid, silica-alumina treated with hexafluorozirconic acid, silica-alumina treated with trifluoroacetic acid, fluorided boria-alumina, silica treated with tetrafluoroboric acid, alumina treated with tetrafluoroboric acid, alumina treated with hexafluorophosphoric acid, or combinations thereof. Further, any of these activator-supports optionally can be treated with a metal ion.

Nonlimiting examples of cations suitable for use in the present disclosure in the salt of the electron-withdrawing anion include ammonium, trialkyl ammonium, tetraalkyl ammonium, tetraalkyl phosphonium, H+, [H(OEt$_2$)$_2$]+, or combinations thereof.

Further, combinations of one or more different electron-withdrawing anions, in varying proportions, can be used to tailor the specific acidity of the support material to a desired level. Combinations of electron-withdrawing components can be contacted with the support material simultaneously or individually, and in any order that provides a desired chemically-treated support material acidity. For example, in at least one embodiment, two or more electron-withdrawing anion source compounds in two or more separate contacting steps.

In at least one embodiment of the present disclosure, one example of a process by which a chemically-treated support material is prepared is as follows: a selected support material, or combination of support materials, can be contacted with a first electron-withdrawing anion source compound to form a first mixture; such first mixture can be calcined and then contacted with a second electron-withdrawing anion source compound to form a second mixture; the second mixture can then be calcined to form a treated support material. In such a process, the first and second electron-withdrawing anion source compounds can be either the same or different compounds.

The method by which the oxide is contacted with the electron-withdrawing component, typically a salt or an acid of an electron-withdrawing anion, can include gelling, co-gelling, impregnation of one compound onto another, or combinations thereof. Following a contacting method, the contacted mixture of the support material, electron-withdrawing anion, and optional metal ion, can be calcined.

According to another embodiment of the present disclosure, the support material can be treated by a process comprising: (i) contacting a support material with a first electron-withdrawing anion source compound to form a first mixture; (ii) calcining the first mixture to produce a calcined first mixture; (iii) contacting the calcined first mixture with a second electron-withdrawing anion source compound to form a second mixture; and (iv) calcining the second mixture to form the treated support material.

Polymer Processes

In embodiments herein, the present disclosure provides polymerization processes where monomer (such as propylene or ethylene), and optionally comonomer, are contacted with a catalyst system comprising an activator and at least one catalyst compound, as described above. The catalyst compound and activator may be combined in any order, and are combined typically prior to contacting with the monomer.

In at least one embodiment, a polymerization process includes a) contacting one or more olefin monomers with a catalyst system comprising: i) an activator and ii) a catalyst compound of the present disclosure. The activator is a non-coordination anion activator. The one or more olefin monomers may be propylene and/or ethylene and the polymerization process further comprises heating the one or more olefin monomers and the catalyst system to 70° C. or more to form propylene polymers or ethylene polymers, such as propylene polymers.

Monomers useful herein include substituted or unsubstituted $C_2$ to $C_{40}$ alpha olefins, such as $C_2$ to $C_{20}$ alpha olefins, such as $C_2$ to $C_{12}$ alpha olefins, such as ethylene, propylene, butene, pentene, hexene, heptene, octene, nonene, decene, undecene, dodecene and isomers thereof. In at least one embodiment, the monomer comprises propylene and an optional comonomers comprising one or more propylene or $C_4$ to $C_{40}$ olefins, such as $C_4$ to $C_{20}$ olefins, such as $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In at least one embodiment, the monomer comprises propylene and an optional comonomers comprising one or more $C_3$ to $C_{40}$ olefins, such as $C_4$ to $C_{20}$ olefins, such as $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include propylene, propylene, butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, such as hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, such as norbornene, norbornadiene, and dicyclopentadiene.

In at least one embodiment, one or more dienes are present in the polymer produced herein at up to 10 wt %, such as at 0.00001 to 1.0 wt %, such as 0.002 to 0.5 wt %, such as 0.003 to 0.2 wt %, based upon the total weight of the composition. In some embodiments, 500 ppm or less of diene is added to the polymerization, such as 400 ppm or less, such as 300 ppm or less. In other embodiments at least 50 ppm of diene is added to the polymerization, or 100 ppm or more, or 150 ppm or more.

Diene monomers include any hydrocarbon structure, such as $C_4$ to $C_{30}$, having at least two unsaturated bonds, wherein at least two of the unsaturated bonds are readily incorporated into a polymer by either a stereospecific or a non-stereospecific catalyst(s). The diene monomers can be selected from alpha, omega-diene monomers (i.e. di-vinyl monomers). The diolefin monomers are linear di-vinyl monomers, such as those containing from 4 to 30 carbon atoms. Examples of dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Cyclic dienes include cyclopentadiene, vinylnorbornene, norbornadiene, ethylidene norbornene, divinylbenzene, dicyclopentadiene or higher ring containing diolefins with or without substituents at various ring positions.

Polymerization processes of the present disclosure can be carried out in any suitable manner. Any suitable suspension, homogeneous, bulk, solution, slurry, or gas phase polymerization process can be used. Such processes can be run in a batch, semi-batch, or continuous mode. Homogeneous polymerization processes and slurry processes can be performed. (A useful homogeneous polymerization process is one where at least 90 wt % of the product is soluble in the reaction media.) A bulk homogeneous process can be used. (An example bulk process is one where monomer concentration in all feeds to the reactor is 70 volume % or more.) Alternately, no solvent or diluent is present or added in the reaction medium, (except for the small amounts used as the carrier for the catalyst system or other additives, or amounts typically found with the monomer; e.g., propane in propylene). In at least one embodiment, the process is a slurry polymerization process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_4$-$C_{10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In at least one embodiment, the solvent is not aromatic, such that aromatics are present in the solvent at less than 1 wt %, such as less than 0.5 wt %, such as less than 0 wt % based upon the weight of the solvents.

In at least one embodiment, the feed concentration of the monomers and comonomers for the polymerization is 60 vol % solvent or less, such as 40 vol % or less, such as 20 vol % or less, based on the total volume of the feedstream. The polymerization can be performed in a bulk process.

Polymerizations can be performed at any temperature and/or pressure suitable to obtain the desired polymers, such as ethylene and or propylene polymers. Typical temperatures and/or pressures include a temperature in the range of from 0° C. to 300° C., such as 20° C. to 200° C., such as 35° C. to 150° C., such as 40° C. to 120° C., such as 45° C. to 80° C., for example about 74° C., and at a pressure in the range of from 0.35 MPa to 10 MPa, such as 0.45 MPa to 6 MPa, such as 0.5 MPa to 4 MPa.

In a typical polymerization, the run time of the reaction is up to 300 minutes, such as in the range of from 5 to 250 minutes, such as 10 to 120 minutes.

In at least one embodiment, hydrogen is present in the polymerization reactor at a partial pressure of 0.001 to 50 psig (0.007 to 345 kPa), such as from 0.01 to 25 psig (0.07 to 172 kPa), such as 0.1 to 10 psig (0.7 to 70 kPa).

In at least one embodiment, the activity of the catalyst is from 50 gP/mmolCat/hour to 200,000 gP/mmolCat/hr, such as from 10,000 gP/mmolCat/hr to 150,000 gP/mmolCat/hr, such as from 40,000 gP/mmolCat/hr to 100,000 gP/mmolCat/hr, such as about 50,000 gP/mmolCat/hr or more, such as 70,000 gP/mmolCat/hr or more. In at least one embodiment, the conversion of olefin monomer is at least 10%, based upon polymer yield and the weight of the monomer entering the reaction zone, such as 20% or more, such as 30% or more, such as 50% or more, such as 80% or more.

In at least one embodiment, a catalyst system of the present disclosure is capable of producing a polyolefin. In at least one embodiment, a polyolefin is a homopolymer of ethylene or propylene or a copolymer of ethylene such as a copolymer of ethylene having from 0.1 to 25 wt % (such as from 0.5 to 20 wt %, such as from 1 to 15 wt %, such as from 5 to 17 wt %) of ethylene with the remainder balance being one or more $C_3$ to $C_{20}$ olefin comonomers (such as $C_3$ to $C_{12}$ alpha-olefin, such as propylene, butene, hexene, octene, decene, dodecene, such as propylene, butene, hexene, octene). A polyolefin can be a copolymer of propylene such as a copolymer of propylene having from 0.1 to 25 wt % (such as from 0.5 to 20 wt %, such as from 1 to 15 wt %, such as from 3 to 10 wt %) of propylene and from 99.9 to 75 wt % of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In at least one embodiment, a catalyst system of the present disclosure is capable of producing polyolefins, such as polypropylene (e.g., iPP) or ethylene-octene copolymers, having an Mw from 40,000 to 1,500,000 g/mol, such as from 70,000 to 1,000,000 g/mol, such as from 90,000 to 500,000 g/mol, such as from 90,000 to 250,000 g/mol, such as from 90,000 to 200,000 g/mol, such as from 90,000 to 110,000 g/mol.

In at least one embodiment, a catalyst system of the present disclosure is capable of producing polyolefins, such as polypropylene (e.g., iPP) or ethylene-octene copolymers, having an Mn from 5,000 to 1,000,000 g/mol, such as from 20,000 to 160,000 g/mol, such as from 30,000 to 70,000 g/mol, such as from 40,000 to 70,000 g/mol. In at least one embodiment, a catalyst system of the present disclosure is capable of producing propylene polymers having an Mw/Mn value from 1 to 10, such as from 1.5 to 9, such as from 2 to 7, such as from 2 to 4, such as from 2.5 to 3, for example about 2.

In at least one embodiment, little or no scavenger is used in the process to produce polymer, such as propylene polymer. Scavenger (such as trialkyl aluminum) can be present at zero mol %, alternately the scavenger is present at a molar ratio of scavenger metal to transition metal of less than 100:1, such as less than 50:1, such as less than 15:1, such as less than 10:1.

In at least one embodiment, the polymerization: 1) is conducted at temperatures of 0 to 300° C. (such as 25 to 150° C., such as 40 to 120° C., such as 70 to 110° C., such as 85 to 100° C.); 2) is conducted at a pressure of atmospheric pressure to 10 MPa (such as 0.35 to 10 MPa, such as from 0.45 to 6 MPa, such as from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, where aromatics are present in the solvent at less than 1 wt %, such as less than 0.5 wt %, such as at 0 wt % based upon the weight of the solvents); and 4) the productivity of the catalyst compound is at least 30,000 gP/mmolCat/hr (such as at least 50,000 gP/mmolCat/hr, such as at least 60,000 gP/mmolCat/hr, such as at least 80,000 gP/mmolCat/hr, such as at least 100,000 gP/mmolCat/hr).

In at least one embodiment, the catalyst system used in the polymerization comprises no more than one catalyst compound. A "reaction zone" also referred to as a "polymerization zone" is a vessel where polymerization takes place, for example a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In at least one embodiment, the polymerization occurs in one reaction zone.

Other additives may also be used in the polymerization, as desired, such as one or more scavengers, promoters, modifiers, chain transfer agents (such as diethyl zinc), hydrogen, or aluminum alkyls. Useful chain transfer agents are typically alkylalumoxanes, a compound represented by the formula $AlR_3$, $ZnR_2$ (where each R is, independently, a $C_1$-$C_8$ aliphatic radical, such as methyl, ethyl, propyl, butyl, phenyl, hexyl, octyl or an isomer thereof) or a combination thereof, such as diethyl zinc, methylalumoxane, trimethylaluminum, triisobutylaluminum, trioctylaluminum, or a combination thereof.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See, for example, U.S. Pat. Nos. 4,543,399; 4,588,790; 5,028,670; 5,317,036; 5,352,749; 5,405,922; 5,436,304; 5,453,471; 5,462,999; 5,616,661; and 5,668,228; all of which are fully incorporated herein by reference.)

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers, along with catalysts, are added. The suspension including diluent is intermittently or continuously removed from the reactor where the volatile components are separated from the polymer and recycled, optionally after a distillation, to the reactor. The liquid diluent used in the polymerization medium is typically an alkane having from 3 to 7 carbon atoms, such as a branched alkane. The medium employed should be liquid under the conditions of polymerization and relatively inert. When a propane medium is used, the process must be operated above the reaction diluent critical temperature and pressure. For example, a hexane or an isobutane medium is employed.

In at least one embodiment, a polymerization process is a particle form polymerization, or a slurry process, where the temperature is kept below the temperature at which the polymer goes into solution. Such technique is well known in the art, and described in for instance U.S. Pat. No. 3,248,179 which is fully incorporated herein by reference. The temperature in the particle form process can be from about 85° C. to about 110° C. Two example polymerization methods for the slurry process are those using a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isohexane or as a dry free flowing powder, is injected regularly to the reactor loop, which is itself filled with circulating slurry of growing polymer particles in a diluent of isohexane containing monomer and optional comonomer. Hydrogen, optionally, may be added as a molecular weight control. (In one embodiment hydrogen is added from 50 ppm to 500 ppm, such as from 100 ppm to 400 ppm, such as 150 ppm to 300 ppm.)

The reactor may be maintained at a pressure of 2,000 kPa to 5,000 kPa, such as from 3,620 kPa to 4,309 kPa, and at a temperature of from about 60° C. to about 120° C. depending on the desired polymer melting characteristics.

Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isohexane diluent and all unreacted monomer and comonomer. The resulting hydrocarbon free powder is then compounded for use in various applications.

Other additives may also be used in the polymerization, as desired, such as one or more scavengers, promoters, modifiers, chain transfer agents (such as diethyl zinc), reducing agents, oxidizing agents, hydrogen, aluminum alkyls, or silanes.

Useful chain transfer agents are typically alkylalumoxanes, a compound represented by the formula $AlR^3$, $ZnR_2$ (where each R is, independently, a $C_1$-$C_8$ hydrocarbyl, such as methyl, ethyl, propyl, butyl, penyl, hexyl octyl or an isomer thereof). Examples can include diethyl zinc, methylalumoxane, trimethylaluminum, triisobutylaluminum, trioctylaluminum, or a combination thereof.

Solution Polymerization

A solution polymerization is a polymerization process in which the polymer is dissolved in a liquid polymerization medium, such as an inert solvent or monomer(s) or their blends. A solution polymerization is typically homogeneous. A homogeneous polymerization is one where the polymer product is dissolved in the polymerization medium. Such systems are typically not turbid as described in Oliveira, J. V. et al. (2000) "High-Pressure Phase Equilibria for Polypropylene-Hydrocarbon Systems," *Ind. Eng. Chem. Res.*, v. 39, pp. 4627-4633. Generally solution polymerization involves polymerization in a continuous reactor in which the polymer formed and the starting monomer and catalyst materials supplied, are agitated to reduce or avoid concentration gradients and in which the monomer acts as a diluent or solvent or in which a hydrocarbon is used as a diluent or solvent. Suitable processes typically operate at temperatures from about 0° C. to about 250° C., such as about 10° C. to about 150° C., such as about 40° C. to about 140° C., such as about 50° C. to about 120° C., and at pressures of about 0.1 MPa or more, such as 2 MPa or more. The upper pressure limit is not critically constrained but typically can be about 200 MPa or less, such as 120 MPa or less. Temperature control in the reactor can generally be obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds can also be used. The purity, type, and amount of solvent can be optimized for the maximum catalyst productivity for a particular type of polymerization. The solvent can be also introduced as a catalyst carrier. The solvent can be introduced as a gas phase or as a liquid phase depending on the pressure and temperature. Advantageously, the solvent can be kept in the liquid phase and introduced as a liquid. Solvent can be introduced in the feed to the polymerization reactors.

Polyolefin Products

The present disclosure also provides compositions of matter which can be produced by the methods described herein.

In at least one embodiment, a polyolefin is a propylene homopolymer, an ethylene homopolymer or an ethylene copolymer, such as propylene-ethylene and/or ethylene-alphaolefin (such as $C_4$ to $C_{20}$) copolymer (such as an ethylene-hexene copolymer or an ethylene-octene copolymer). A polyolefin can have an Mw/Mn of greater than 1 to 4 (such as greater than 1 to 3).

In at least one embodiment, a polyolefin is a homopolymer of ethylene or propylene or a copolymer of ethylene such as a copolymer of ethylene having from 0.1 to 25 wt % (such as from 0.5 to 20 wt %, such as from 1 to 15 wt %, such as from 5 to 17 wt %) of ethylene with the remainder balance being one or more $C_3$ to $C_{20}$ olefin comonomers (such as $C_3$ to $C_{12}$ alpha-olefin, such as propylene, butene, hexene, octene, decene, dodecene, such as propylene, butene, hexene, octene). A polyolefin can be a copolymer of propylene such as a copolymer of propylene having from 0.1 to 25 wt % (such as from 0.5 to 20 wt %, such as from 1 to 15 wt %, such as from 3 to 10 wt %) of propylene and from 99.9 to 75 wt % of one or more of $C_2$ or $C_4$ to $C_{20}$ olefin comonomer (such as ethylene or $C_4$ to $C_{12}$ alpha-olefin, such as butene, hexene, octene, decene, dodecene, such as ethylene, butene, hexene, octene).

In at least one embodiment, a polyolefin, such as a polypropylene (e.g., iPP) or an ethylene-octene copolymer, has an Mw from 40,000 to 1,500,000, such as from 70,000 to 1,000,000, such as from 90,000 to 500,000, such as from 90,000 to 250,000, such as from 90,000 to 200,000, such as from 90,000 to 110,000.

In at least one embodiment, a polyolefin, such as a polypropylene (e.g., iPP) or an ethylene-octene copolymer, has an Mn from 5,000 to 1,000,000, such as from 20,000 to 160,000, such as from 30,000 to 70,000, such as from 40,000 to 70,000. In at least one embodiment, a polyolefin, such as a polypropylene (e.g., iPP) or an ethylene-octene copolymer, has an Mw/Mn value from 1 to 10, such as from 1.5 to 9, such as from 2 to 7, such as from 2 to 4, such as from 2.5 to 3, for example about 2.

In at least one embodiment, a polyolefin, such as a polypropylene (e.g., iPP) or an ethylene-octene copolymer, has a melt temperature (Tm) of from 100° C. to 150° C., such as 110° C. to 140° C., such as 120° C. to 1350, such as 130° C. to 135° C.

In at least one embodiment, a polymer of the present disclosure has a g' vis of greater than 0.9, such as greater than 0.92, such as greater than 0.95.

In at least one embodiment, the polymer is an ethylene copolymer, and the comonomer is octene, at a comonomer content of from 1 wt % to 18 wt % octene, such as from 5 wt % to 15 wt %, such as from 8 wt % to 13 wt %, such as from 9 wt % to 12 wt %.

In at least one embodiment, the polymer produced herein has a unimodal or multimodal molecular weight distribution as determined by Gel Permeation Chromatography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versus).

In at least one embodiment, the polymer produced herein has a composition distribution breadth index (CDBI) of 50% or more, such as 60% or more, such as 70% or more. CDBI is a measure of the composition distribution of monomer within the polymer chains and is measured by the procedure described in PCT publication WO 93/03093, published Feb. 18, 1993, specifically columns 7 and 8 as well as in Wild, L. et al. (1982) "Determination of Branching Distributions in Polyethylene and ethylene Copolymers," *J. Poly. Sci., Poly. Phys. Ed.*, v. 20, pp. 441-455 and U.S. Pat. No. 5,008,204, including that fractions having a weight average molecular weight (Mw) below 15,000 are ignored when determining CDBI.

In at least one embodiment of the present disclosure, the polymer produced by the processes described herein includes ethylene and one or more comonomers and the polymer has: 1) an RCI,m of 30 or more (alternatively from 30 to 250).

Molecular Weight, Comonomer Composition and Long Chain Branching Determination by Polymer Char GPC-IR Hyphenated with Multiple Detectors The distribution and the moments of molecular weight (Mw, Mn, Mw/Mn, etc.), the comonomer content ($C_2$, $C_3$, $C_6$, etc.) and the long chain branching (g') are determined by using a high temperature Gel Permeation Chromatography (Polymer Char GPC-IR) equipped with a multiple-channel band-filter based Infrared detector IR5, an 18-angle light scattering detector and a viscometer. Three Agilent PLgel 10 μm Mixed-B LS columns are used to provide polymer separation. Aldrich reagent grade 1,2,4-trichlorobenzene (TCB) with 300 ppm antioxidant butylated hydroxytoluene (BHT) is used as the mobile phase. The TCB mixture is filtered through a 0.1 μm Teflon filter and degassed with an online degasser before entering the GPC instrument. The nominal flow rate is 1.0 mL/min and the nominal injection volume is 200 μL. The whole system including transfer lines, columns, detectors are contained in an oven maintained at 145° C. Given amount of polymer sample is weighed and sealed in a standard vial with 80 μL flow marker (Heptane) added to it. After loading the vial in the autosampler, polymer is automatically dissolved in the instrument with 8 mL added TCB solvent. The polymer is dissolved at 160° C. with continuous shaking for about 1 hour for most PE samples or 2 hour for PP samples. The TCB densities used in concentration calculation are 1.463 g/ml at room temperature and 1.284 g/ml at 145° C. The sample solution concentration is from 0.2 to 2.0 mg/ml, with lower concentrations being used for higher molecular weight samples.

The concentration (c), at each point in the chromatogram is calculated from the baseline-subtracted IR5 broadband signal intensity (I), using the following equation:

$$c = \beta I$$

where β is the mass constant determined with PE or PP standards. The mass recovery is calculated from the ratio of the integrated area of the concentration chromatography over elution volume and the injection mass which is equal to the pre-determined concentration multiplied by injection loop volume.

The conventional molecular weight (IR MW) is determined by combining universal calibration relationship with the column calibration which is performed with a series of monodispersed polystyrene (PS) standards ranging from 700 to 10M. The MW at each elution volume is calculated with following equation.

$$\log M = \frac{\log(K_{PS}/K)}{a+1} + \frac{a_{PS}+1}{a+1} \log M_{PS}$$

where the variables with subscript "PS" stands for polystyrene while those without a subscript are for the test samples. In this method, $a_{PS}=0.67$ and $K_{PS}=0.000175$ while a and K are calculated as described in the published in literature (Sun, T. et al. (2001) "Effect of Short Chain Branching on the Coil Dimensions of Polyolefins in Dilute Solutions," *Macromolecules*, v. 34(19), pp. 6812-6820), except that for purposes of this invention and claims thereto, $\alpha=0.695$ and $K=0.000579$ for polyethylene, $\alpha=0.705$ and $K=0.0002288$ for polypropylene, $\alpha=0.695+(0.01*(\text{wt. fraction propylene}))$ and $K=0.000579-(0.0003502*(\text{wt. fraction propylene}))$ for ethylene-propylene copolymers and ethylene-propylene-diene terpolymers, $\alpha=0.695$ and $K=0.000181$ for linear butene polymers, α is 0.695 and K is $0.000579*(1-0.0087*w2b+0.000018*(w2b)^2)$ for ethylene-butene copolymer where w2b is a bulk weight percent of butene comonomer, α is 0.695 and K is $0.000579*(1-0.0075*w2b)$ for ethylene-hexene copolymer where w2b is a bulk weight percent of hexene comonomer, and α is 0.695 and K is $0.000579*(1-0.0077*w2b)$ for ethylene-octene copolymer where w2b is a bulk weight percent of octene comonomer. Concentrations are expressed in g/cm³, molecular weight is expressed in g/mole, and intrinsic viscosity (hence K in the Mark-Houwink equation) is expressed in dL/g unless otherwise noted.

The comonomer composition is determined by the ratio of the IR5 detector intensity corresponding to $CH_2$ and $CH_3$ channel calibrated with a series of PE and PP homo/copolymer standards whose nominal value are predetermined by NMR or FTIR such as EMCC commercial grades about LLDPE, Vistamaxx, ICP, etc.

The LS detector is the 18-angle Wyatt Technology High Temperature DAWN HELEOSII. The LS molecular weight (M) at each point in the chromatogram is determined by analyzing the LS output using the Zimm model for static light scattering (M. B. Huglin, *Light Scattering from Polymer Solutions*, Academic Press, 1971):

$$\frac{K_o c}{\Delta R(\theta)} = \frac{1}{MP(\theta)} + 2A_2 c$$

Here, $\Delta R(\theta)$ is the measured excess Rayleigh scattering intensity at scattering angle θ, c is the polymer concentration determined from the IR5 analysis, $A_2$ is the second virial coefficient. P(θ) is the form factor for a monodisperse random coil, and $K_o$ is the optical constant for the system:

$$K_o = \frac{4\pi^2 n^2 (dn/dc)^2}{\lambda^4 N_A}$$

where $N_A$ is Avogadro's number, and (dn/dc) is the refractive index increment for the system. The refractive index, n=1.500 for TCB at 145° C. and λ=665 nm.

A high temperature Agilent (or Viscotek Corporation) viscometer, which has four capillaries arranged in a Wheatstone bridge configuration with two pressure transducers, is used to determine specific viscosity. One transducer measures the total pressure drop across the detector, and the other, positioned between the two sides of the bridge, measures a differential pressure. The specific viscosity, $\eta_s$, for the solution flowing through the viscometer is calculated from their outputs. The intrinsic viscosity, [η], at each point in the chromatogram is calculated from the following equation:

$$[\eta] = \eta_s/c$$

where c is concentration and was determined from the IR5 broadband channel output. The viscosity MW at each point is calculated from the below equation:

$$M = K_{PS} M^{\alpha PS+1}/[\eta].$$

The branching index ($g'_{vis}$) is calculated using the output of the GPC-IR5-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits. The branching index $g'_{vis}$ is defined as:

$$g'_{vis} = \frac{[\eta]_{avg}}{k M_v^\alpha}$$

$M_v$ is the viscosity-average molecular weight based on molecular weights determined by LS analysis. The K/a are for the reference linear polymers are as described above.

All the concentration is expressed in g/cm$^3$, molecular weight is expressed in g/mole, and intrinsic viscosity is expressed in dL/g unless otherwise noted.

All molecular weights are reported in g/mol unless otherwise noted.

Differential Scanning Calorimetry (DSC-Procedure-2). Melting Temperature, Tm, is measured by differential scanning calorimetry ("DSC") using a DSCQ200 unit. The sample is first equilibrated at 25° C. and subsequently heated to 220° C. using a heating rate of 10° C./min (first heat). The sample is held at 220° C. for 3 min. The sample is subsequently cooled down to −100° C. with a constant cooling rate of 10° C./min (first cool). The sample is equilibrated at −100° C. before being heated to 220° C. at a constant heating rate of 10° C./min (second heat). The exothermic peak of crystallization (first cool) is analyzed using the TA Universal Analysis software and the corresponding to 10° C./min cooling rate is determined. The endothermic peak of melting (second heat) is also analyzed using the TA Universal Analysis software and the peak melting temperature (Tm) corresponding to 10° C./min heating rate is determined. In the event of conflict between the DSC Procedure-1 and DSC procedure-2, DSC procedure-2 is used.

Blends

In another embodiment, the polymer (such as the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, low density polyethylene (LDPE), linear low density polyethylene (LLDPE), high density polyethylene (HDPE), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In at least one embodiment, the polymer (such as polyethylene or polypropylene) is present in the above blends, at from 10 to 99 wt %, based upon the weight of the polymers in the blend, such as 20 to 95 wt %, such as at least 30 to 90 wt %, such as at least 40 to 90 wt %, such as at least 50 to 90 wt %, such as at least 60 to 90 wt %, such as at least 70 to 90 wt %.

The blends described above may be produced by mixing the polymers of the present disclosure with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; and talc.

Films

One or more of the foregoing polymers, such as the foregoing polyethylenes, polypropylenes, or blends thereof, may be used in a variety of end-use applications. Such applications include, for example, mono- or multi-layer blown, extruded, and/or shrink films. These films may be formed by any number of well-known extrusion or coextrusion techniques, such as a blown bubble film processing technique, wherein the composition can be extruded in a molten state through an annular die and then expanded to form a uni-axial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or a double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then optionally the combination could be oriented even further. Typically the films are oriented in the Machine Direction (MD) at a ratio of up to 15, such as between 5 and 7, and in the Transverse Direction (TD) at a ratio of up to 15, such as 7 to 9. However, in at least one embodiment the film is oriented to the same extent in both the MD and TD directions.

The films may vary in thickness depending on the intended application; however, films of a thickness from 1 μm to 50 μm are usually suitable. Films intended for packaging are usually from 10 μm to 50 μm thick. The thickness of the sealing layer is typically 0.2 μm to 50 μm. There may be a sealing layer on both the inner and outer surfaces of the film or the sealing layer may be present on only the inner or the outer surface.

In at least one embodiment, one or more layers may be modified by corona treatment, electron beam irradiation, gamma irradiation, flame treatment, or microwave. In at least one embodiment, one or both of the surface layers is modified by corona treatment.

This invention further relates to:

1. A compound represented by Formula (AI):

$$[R^1R^2R^3EH]_d^+[M^{k+}Q_n]^{d-} \quad (AI)$$

wherein:

E is nitrogen or phosphorous;

d is 1, 2 or 3; k is 1, 2, or 3; n is 1, 2, 3, 4, 5, or 6; n–k=d;

each of $R^1$, $R^2$, and $R^3$ is independently hydrogen, a $C_1$-$C_{40}$ branched or linear alkyl, or a $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms; M is an element selected from group 13 of the Periodic Table of the Elements; and each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical, provided that at least one of $R^1$, $R^2$, and $R^3$ is a branched alkyl.

2. A compound represented by Formula (I):

$$[R^1R^2R^3EH]^+[BR^4R^5R^6R^7]^- \quad (I)$$

wherein:

E is nitrogen or phosphorous;

each of $R^1$, $R^2$, and $R^3$ is independently $C_1$-$C_{40}$ branched or linear alkyl or $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms; and each of $R^4$, $R^5$, $R^6$, and $R^7$ is naphthyl, wherein at least one of $R^4$, $R^5$, $R^6$, and $R^7$ is substituted with from one to seven fluorine atoms and provided that at least one of $R^1$, $R^2$, and $R^3$ is a branched alkyl.

3. The compound of paragraph 1 or 2, wherein: at least one (or two, or three) of $R^1$, $R^2$, and $R^3$ is independently a $C_3$-$C_{40}$ branched alkyl; and each of $R^1$, $R^2$, and $R^3$ is independently unsubstituted or substituted with at least one of halide, $C_5$-$C_{15}$ aryl, $C_6$-$C_{25}$ arylalkyl, and $C_6$-$C_{25}$ alkylaryl.

4. The compound of paragraph 1 or 2, wherein: $R^1$ is a methyl group; $R^2$ is $C_{10}$-$C_{42}$ aryl; $R^3$ is independently $C_1$-$C_{40}$ branched alkyl; wherein each of $R^2$ and $R^3$ is independently unsubstituted or substituted with at least one of halide, $C_5$-$C_{15}$ aryl, $C_6$-$C_{25}$ arylalkyl, $C_6$-$C_{25}$ alkylaryl, and in the case of the $C_{10}$ to $C_{42}$ aryl, $C_1$-$C_{10}$ alkyl; and $R^2$ and $R^3$ together comprise 20 or more carbon atoms.

5. The compound of paragraph 1, 2, 3, or 4 wherein E is nitrogen.

6. The compound of any of paragraphs 1, 2, 3, 4 or 5, wherein $R^4$, $R^5$, $R^6$, and $R^7$ are perfluoroaryl.

7. The compound of any of paragraphs 1, 2, 3, 4, or 5, wherein each of $R^4$, $R^5$, $R^6$, and $R^7$ is substituted with from one to seven fluorine atoms, preferably seven fluorine atoms.

8. The compound of any of paragraphs 1, 2, 3, 4, 5, 6, or 7, wherein $R^1$, $R^2$, and $R^3$ together comprise 21 (or 22, or 25, or 30, or 35, or 40, or 43, or 45) or more carbon atoms.

9. The compound of any of paragraphs 1 to 7, wherein all Q in formula (AI) are not perfluorophenyl, and each of $R^4$, $R^5$, $R^6$, and $R^7$ in formula (I) are not perfluorophenyl.

10. The compound of paragraph 1 or 2, wherein the branched alkyl is represented by the formula:

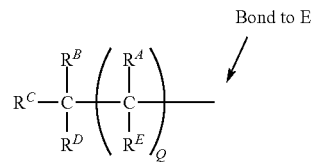

wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$—C—$R^E$) group, one or both of $R^A$ and $R^E$ is not H; and $R^C$, $R^B$ and $R^D$ are hydrogen; and Q is an integer from 5 to 40.

11. The compound of any of the above paragraphs wherein one, two or three of $R^1$, $R^2$ and $R^3$ are independently represented by the formula (IV) where:

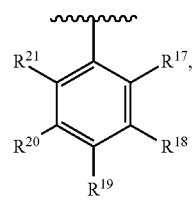

each of $R^{17}$, $R^{18}$, $R^{19}$, $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, a heteroatom-containing group, or is represented by formula (BIII), provided that at least one of $R^{17}$, $R^{18}$, $R^{19}$, $R^{20}$, and $R^{21}$ is not hydrogen, where formula (BIII) is:

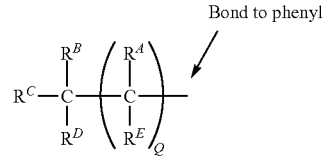

wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$—C—$R^E$) group, one or both of $R^A$ and $R^E$ is not H;
$R^C$, $R^B$ and $R^D$ are hydrogen; and
Q is an integer from 5 to 40.

12. The compound of paragraph 1 or 2, wherein $R^1$ is $C_1$-$C_{10}$ alkyl, preferably methyl, and each of $R^2$ and $R^3$ is independently a branched $C_{10}$-$C_{40}$ alkyl.

13. The compound of paragraph 1 or 2, wherein $R^1$ is $C_5$-$C_{22}$-aryl and each of each of $R^2$ and $R^3$ is $C_1$-$C_{40}$ branched alkyl, wherein $R^1$ is unsubstituted or substituted with at least one $C_1$-$C_{10}$ alkyl.

14. The compound of paragraph 13, wherein $R^1$ is phenyl, $R^2$ is methyl, and $R^3$ is $C_{10}$-$C_{40}$ branched alkyl.

15. The compound of any of the above claims 1 to 14, wherein the compound has a solubility of more than 10 mM (or more than 20 mM, or more than 50 mM) at 25° C. (stirred 2 hours) in methylcyclohexane and/or a solubility of more than 1 mM (or more than 10 mM, or more than 20 mM) at 25° C. (stirred 2 hours) in isohexane.

16. A catalyst system comprising a catalyst and the activator compound of any of paragraphs 1 to 15.

17. The catalyst system of paragraph 16, further comprising a support material, preferably selected from $Al_2O_3$, $ZrO_2$, $SiO_2$, $SiO_2/Al_2O_3$, $SiO_2/TiO_2$, silica clay, silicon oxide/clay, or mixtures thereof.

18. The catalyst system of paragraph 16 or 17, wherein the catalyst is represented by formula (II) or formula (III):

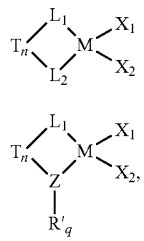

wherein in each of formula (II) and formula (III): M is the metal center, and is a Group 4 metal; n is 0 or 1; T is an optional bridging group selected from dialkylsilyl, diarylsilyl, dialkylmethyl, ethylenyl or hydrocarbylethylenyl wherein one, two, three or four of the hydrogen atoms in ethylenyl are substituted by hydrocarbyl; Z is nitrogen, oxygen, sulfur, or phosphorus; R' is a cyclic, linear or branched $C_1$ to $C_{40}$ alkyl or substituted alkyl group, and Z—R' may optionally form a cyclic group, preferably R' is a linear $C_1$-$C_{40}$ alkyl or substituted alkyl group; q is 1 or 2; and $X_1$ and $X_2$ are, independently, hydrogen, halogen, hydride radicals, hydrocarbyl radicals, substituted hydrocarbyl radicals, halocarbyl radicals, substituted halocarbyl radicals, silylcarbyl radicals, substituted silylcarbyl radicals, germylcarbyl radicals, or substituted germylcarbyl radicals; or both $X_1$ and $X_2$ are joined and bound to the metal atom to form a metallacycle ring containing from about 3 to about 20 carbon atoms; or both together can be an olefin, diolefin or aryne ligand.

19. The catalyst system of paragraph 18, wherein the catalyst is $C_2$ symmetrical.

20. The catalyst system of paragraph 16 or 17, wherein the catalyst is rac-dimethylsilyl-bis(indenyl)hafnium dimethyl.

21. The catalyst system of paragraph 16 or 17, wherein the catalyst is one or more of:
dimethylsilylbis(tetrahydroindenyl)$MX_n$,
dimethylsilyl bis(2-methylindenyl)$MX_n$,
dimethylsilyl bis(2-methylfluorenyl)$MX_n$,
dimethylsilyl bis(2-methyl-5,7-propylindenyl)$MX_n$,
dimethylsilyl bis(2-methyl-4-phenylindenyl)$MX_n$,
dimethylsilyl bis(2-ethyl-5-phenylindenyl)$MX_n$,
dimethylsilyl bis(2-methyl-4-biphenylindenyl)$MX_n$,
dimethylsilylene bis(2-methyl-4-carbazolylindenyl)$MX_n$,
rac-dimethylsilyl-bis-(5,6,7,8-tetrahydro-5,5,8,8-tetramethyl-2-methyl-1H-benz(f)indene)$MX_n$,
diphenylmethylene (cyclopentadienyl)(fluoreneyl)$MX_n$,
bis(methylcyclopentadienyl)$MX_n$,
rac-dimethylsiylbis(2-methyl,3-propyl indenyl)$MX_n$,
dimethylsilylbis(indenyl)$MX_n$,
Rac-meso-diphenylsilyl-bis(n-propylcyclopentadienyl) $MX_n$,
1, 1'-bis(4-triethylsilylphenyl)methylene-(cyclopentadienyl) (3,8-di-tertiary-buty-1-fluorenyl)$MX_n$ (bridge is considered the 1 position),
bis-trimethylsilylphenyl-methylene(cyclopentadienyl)(di-t-butylfluorenyl)$MX_n$,
bis-trimethylsilylphenyl-methylene(cyclopentadienyl)(fluorenyl)$MX_n$,
bisphenylmethylene(cyclopentadienyl)(dimethylfluorenyl) $MX_n$,
bis(n-propylcyclopentadienyl)$MX_n$,
bis(n-butylcyclopentadienyl)$MX_n$,
bis(n-pentylcyclopentadienyl)$MX_n$,
(n-propyl cyclopentadienyl)(n-butylcyclopentadienyl)$MX_n$,
bis[(2-trimethylsilylethyl)cyclopentadienyl]$MX_n$,
bis(trimethylsilyl cyclopentadienyl)$MX_n$,
dimethylsilylbis(n-propylcyclopentadienyl)$MX_n$,
dimethylsilylbis(n-butylcyclopentadienyl)$MX_n$,
bis(1-n-propyl-2-methylcyclopentadienyl)$MX_n$,
(n-propylcyclopentadienyl)(1-n-propyl-3-n-butylcyclopentadienyl)$MX_n$,
bis(1-methyl, 3-n-butyl cyclopentadienyl)$MX_n$,
bis(indenyl)$MX_n$,
dimethylsilyl (tetramethylcyclopentadienyl)(cyclododecylamido)$MX_n$,
dimethylsilyl (tetramethylcyclopentadienyl)(t-butylamido) $MX_n$,
$\mu$-$(CH_3)_2$Si(cyclopentadienyl)(1-adamantylamido)$MX_n$,
$\mu$-$(CH_3)_2$Si(3-tertbutylcyclopentadienyl)(1-adamantylamido)$MX_n$,
$\mu$-$(CH_3)_2$(tetramethylcyclopentadienyl)(1-adamantylamido) $MX_n$,
$\mu$-$(CH_3)_2$Si(tetramethylcyclopentadienyl)(1-adamantylamido)$MX_n$,
$\mu$-$(CH_3)_2$C(tetramethylcyclopentadienyl)(1-adamantylamido)$MX_n$,
$\mu$-$(CH_3)_2$Si(tetramethylcyclopentadienyl)(1-tertbutylamido) $MX_n$,
$\mu$-$(CH_3)_2$Si(fluorenyl)(1-tertbutylamido)$MX_n$,
$\mu$-$(CH_3)_2$Si(tetramethylcyclopentadienyl)(1-cyclododecylamido)$MX_n$,
$\mu$-$(C_6H_5)_2$C(tetramethylcyclopentadienyl)(1-cyclododecylamido)$MX_n$,
$\mu$-$(CH_3)_2$Si($\eta^5$-2,6,6-trimethyl-1,5,6,7-tetrahydro-s-indacen-1-yl)(tertbutylamido)$MX_n$,
where M is selected from Ti, Zr, and Hf; X is selected from the group consisting of halogens, hydrides, $C_{1-12}$ alkyls, $C_{2-12}$ alkenyls, $C_{6-12}$ aryls, $C_{7-20}$ alkylaryls, $C_{1-12}$ alkoxys, $C_{6-16}$ aryloxys, $C_{7-18}$ alkylaryloxys, $C_{1-12}$ fluoroalkyls, $C_{6-12}$ fluoroaryls, and $C_{1-12}$ heteroatom-containing hydrocarbons, substituted derivatives thereof, and combinations thereof, and where n is zero or an integer from 1 to 4, preferably X is selected from halogens (such as bromide, fluoride, chloride), or $C_1$ to $C_{20}$ alkyls (such as methyl, ethyl, propyl, butyl, and pentyl) and n is 1 or 2, preferably 2.

22. The catalyst system of paragraph 16 or 17, wherein the catalyst is one or more of:
bis(1-methyl, 3-n-butyl cyclopentadienyl)M(R)$_2$;
dimethylsilyl bis(indenyl)M(R)$_2$;
bis(indenyl)M(R)$_2$;
dimethylsilyl bis(tetrahydroindenyl)M(R)$_2$;
bis(n-propylcyclopentadienyl)M(R)$_2$;
dimethylsilyl (tetramethylcyclopentadienyl)(cyclododecylamido)M(R)$_2$;
dimethylsilyl (tetramethylcyclopentadienyl)(cyclododecylamido)M(R)$_2$;
dimethylsilyl (tetramethylcyclopentadienyl)(t-butylamido) M(R)$_2$;
dimethylsilyl (tetramethylcyclopentadienyl)(t-butylamido) M(R)$_2$;
μ-(CH$_3$)$_2$Si(cyclopentadienyl)(1-adamantylamido)M(R)$_2$;
μ-(CH$_3$)$_2$Si(3-tertbutylcyclopentadienyl)(1-adamantylamido)M(R)$_2$;
μ-(CH$_3$)$_2$(tetramethylcyclopentadienyl)(1-adamantylamido) M(R)$_2$;
μ-(CH$_3$)$_2$Si(tetramethylcyclopentadienyl)(1-adamantylamido)M(R)$_2$;
μ-(CH$_3$)$_2$C(tetramethylcyclopentadienyl)(1-adamantylamido)M(R)$_2$;
μ-(CH$_3$)$_2$Si(tetramethylcyclopentadienyl)(1-tertbutylamido) M(R)$_2$;
μ-(CH$_3$)$_2$Si(fluorenyl)(1-tertbutylamido)M(R)$_2$;
μ-(CH$_3$)$_2$Si(tetramethylcyclopentadienyl)(1-cyclododecylamido)M(R)$_2$;
μ-(C$_6$H$_5$)$_2$C(tetramethylcyclopentadienyl)(1-cyclododecylamido)M(R)$_2$;
μ-(CH$_3$)$_2$Si(η$^5$-2,6,6-trimethyl-1,5,6,7-tetrahydro-s-indacen-1-yl)(tertbutylamido)M(R)$_2$;
where M is selected from Ti, Zr, and Hf; and R is selected from halogen or $C_1$ to $C_5$ alkyl.

23. The catalyst system of paragraph 16 or 17, wherein the catalyst is represented by the catalyst compound (BI) (BII), (BIII), (CI), (CII), (CIII), (IV), (VII), (VIII), (IX), (X), (XI), (XII), (XIII), (XIV), or (XV), as described herein.

24. A method of polymerizing olefins to produce at least one polyolefin, the method comprising contacting at least one olefin with the catalyst system of any of paragraphs 16 to 23, and obtaining a polyolefin.

25. The method of paragraph 24, wherein the at least one olefin is propylene and the polyolefin is isotactic polypropylene.

26. A method of polymerizing olefins to produce at least one polyolefin, the method comprising contacting two or more different olefins with the catalyst system of any of paragraphs 16 to 23; and obtaining a polyolefin.

27. The method of paragraph 26, wherein the two or more olefins are ethylene and propylene.

28. The method of paragraph 26 or 27, wherein the two or more olefins further comprise a diene.

29. The method of any of paragraphs 24 to 28, wherein the method is performed in the gas phase or slurry phase.

30. The method of any of paragraphs 24 to 28, wherein the method is performed in the solution phase.

EXPERIMENTAL

Lithium tetrakis(pentafluorophenyl)borate etherate (Li—BF20) was purchased from Boulder Scientific. N,N-Dimethylanilinium tetrakis(pentafluorophenyl)borate (DMAH-BF20) was purchased from Grace Davison and converted to sodium tetrakis(heptafluoronaphthalen-2-yl)borate (Na—BF28) by reaction with sodium hydride in toluene. N,N-dimethylanilinium tetrakis(heptafluoronaphthalen-2-yl)borate (DMAH-BF28) were purchased from Grace Davison. Exxal™ 13 is an oxo alcohol produced by ExxonMobil Chemical Company, Houston, Tex., and is a mixture of isomers. Bis(4-(2,4,4-trimethylpentan-2-yl)phenyl)amine was purchased from Oakwood chemical. All other reagents were purchased from Sigma-Aldrich and used as received. All anhydrous solvents were purchased from Sigma-Aldrich. Solvents (Sigma-Aldrich) were sparged with nitrogen and stored over molecular sieves.

BF20 is tetrakis(pentafluorophenyl)borate.

BF28 is tetrakis(heptafluoronaphthalen-2-yl)borate.

MCN-1 is dimethylsilylbis(indenyl)hafnium dimethyl.

$^1$H NMR for Compound Characterization:

Chemical structures are determined by 1H NMR. 1H NMR data are collected at room temperature (e.g., 23° C.) in a 5 mm probe. The $^1$H NMR measurements were recorded on a 400 MHz or 500 MHz Bruker spectrometer with chemical shifts referenced to residual solvent peaks (CDCl$_3$: 7.27 ppm for $^1$H, 77.23 ppm for $^{13}$C).

Exxal™ 13 Isotridecyl Alcohol is a $C_{13}$ branched alcohol available from ExxonMobil Chemical Company, Houston, Tex.

Examples

Borate anions and ammonium cations used as activator components are shown in Scheme 1.

Scheme 1: Borate Anions and Ammonium Cations used as Activator Components.

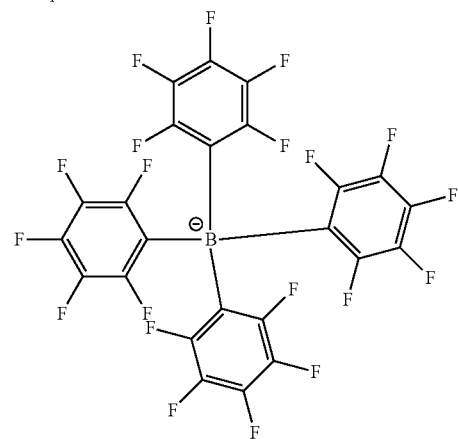

-continued

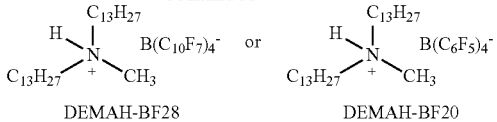

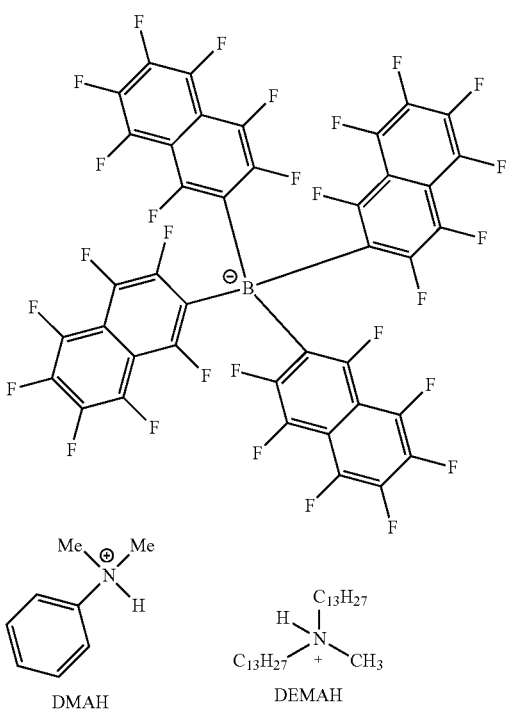

Synthesis of Activators

General Synthesis of Ammonium Borate Activators:

Ammonium borate activators were prepared using a two-step process. In the first step, an amine was prepared from a branched alkyl bromide; and then the amine was dissolved in a solvent (e.g. hexane, cyclohexane, methylcyclohexane, ether, dichloromethane, toluene) and an excess (ca. 1.2 molar equivalents) of hydrogen chloride was added to form an ammonium chloride salt. This salt was isolated by filtration from the reaction medium and dried under reduced pressure. The isolated ammonium chloride was then heated to reflux with one molar equivalent of an alkali metal borate in a solvent (e.g. cyclohexane, dichloromethane, methylcyclohexane) to form the ammonium borate along with byproduct alkali metal chloride, the latter which typically is removed by filtration. Examples describing the synthetic details for selected ammonium borates are given below. For example:

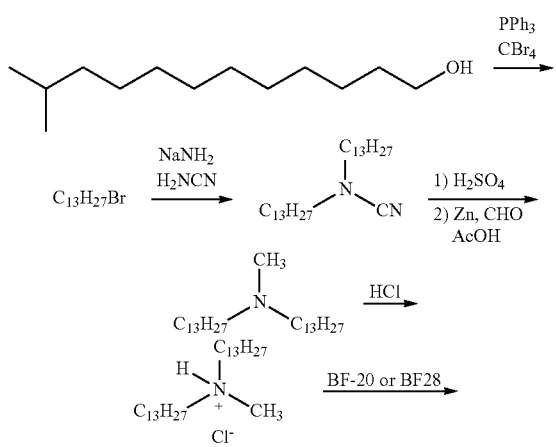

Isotridecyl Bromide (Br—$C_{13}$):

(Exxal™ 13 Alcohols, obtained from ExxonMobil Chemical Company) (45.0 g, 225 mmol) and triphenylphosphine (117.8 g, 449 mmol) were dissolved in methylene chloride (200 mL). Carbon tetrabromide (89.3 g, 270 mmol) was added at a slow rate to prevent reflux. Upon completion, diethyl ether was added to cause a white precipitate, which was filtered away. The filtrate was concentrated to a white solid and the solid extracted with pentane. The pentane fractions were concentrated to a colorless oil. NMR analysis indicated the presence of triphenylphosphine oxide, thus the oil was extracted with pentane twice more. The bromide was obtained in 60% yield as a pale yellow oil.

N,N-Di-Isotridecylcyanamide:

Sodium amide (2.04 g, 52.3 mmol) was added to a solution of cyanamide (1.0 g, 23.8 mmol) in anhydrous dimethylformamide (13 mL) at 0° C. and stirred for 30 minutes. Then Br—$C_{13}$ prepared above (12.5 g, 47.5 mmol, 2.0 equiv) in anhydrous dimethylformamide (12 mL) was added and stirred the reaction was stirred at room temperature for 4 days. The reaction was diluted with ethyl acetate (250 mL), and washed with saturated brine solution (200 mL). The organic layer separated and the aqueous layer was extracted with ethyl acetate (2×250 mL). The combined organic layers were dried over sodium sulfate (100 g) and concentrated under reduced pressure. The crude product was purified over silica gel (300.0 g), eluting with 10% ethyl acetate in heptanes to give the dialkylcyanamide (5.5 g, 56% yield) as a colorless viscous liquid.

Di-Isotridecylamine:

A solution of 2.75 M sulfuric acid (11.0 mL) and N,N-di-isotridecylcyanamide (2.0 g, 4.9 mmol) was refluxed for 6.0 hours. When the reaction was determined to be complete by NMR analysis, it was cooled to room temperature and diluted with water (10.0 mL) and 24% sodium hydroxide solution (10.0 mL). The mixture was extracted with chloroform (3×200 mL). The combined organic layers were washed with saturated brine (100.0 mL), dried over sodium sulfate (100.0 g) and concentrated at 20° C. under reduced pressure. The product was dried in high vacuum chamber at room-temperature for 2.0 hours to give di-isotridecylamine (1.75 g, 93% yield) as a light yellow oil.

N-Methyl-N-Tridecyltridecan-1-Amine (DEMA):

37% Aqueous formaldehyde (1.06 ml, 13.2 mmol), acetic acid (2.0 mL, 35.0 mmol) and zinc (1.15 g, 17.5 mmol) were sequentially added to a solution of di-isotridecylamine (3.35 g, 8.8 mmol) in 1,4-dioxane (10.0 mL) at room temperature. After stirring for 24 hours, NMR analysis indicated the reaction was complete. The reaction mixture was diluted with ammonium hydroxide solution (10.0 mL) and stirred at room-temperature for 2 hours. The reaction was diluted with ethyl acetate (100 mL) and passed through Celite (50.0 g). The Celite bed was washed with additional ethyl acetate (100.0 mL). The combined filtrates were washed with saturated sodium bicarbonate (100 mL) and water (100 mL). The combined aqueous layers were extracted with ethyl acetate (2×250 mL). All the organic layers were combined, dried over sodium sulfate and concentrated under reduced pressure to give compound 5 (2.5 g, 72% yield) as an yellow oil.

N-Methyl-N-Tridecyltridecan-1-Aminium Chloride (DEMAH-Cl):

4.0 M HCL in dioxane (3.16 mL, 12.6 mmol) was added to a solution of DEMA (2.5 g, 6.3 mmol) in 1,4-dioxane (32.0 mL). After stirring at room-temperature for 2.0 hours, the reaction was concentrated under reduced pressure. The product was dissolved in diethyl ether (5×250 mL) and concentrated under reduced pressure to give DEMAH (2.72 g, 99.8% yield) as a brown viscous liquid.

N-Methyl-N-Tridecyltridecan-1-Aminium BF20 (DEMAH-BF20):

The HCl salt (0.5 g, 1.1 mmol) described above, was suspended in 100 mL of cyclohexane and combined with a suspension of Li—BF20 (0.89 g, 1.1 mmol) in 100 mL of cyclohexane. The mixture was heated at 80° C. for 1.5 h, then cooled to ambient. The solvent was decanted away and the pink oil remaining in the flask was dissolved in methylene chloride, filtered through Celite, and concentrated under vacuum to give the product in 48% yield.

N-Methyl-N-Tridecyltridecan-1-Aminium BF28 (DEMAH-BF28):

The HCl salt (0.5 g, 1.1 mmol) described above, was suspended in 100 mL of cyclohexane and combined with a suspension of Na—BF-28 (1.2 g, 1.1 mmol) in 100 mL of cyclohexane. The mixture was heated at 80° C. for 1.5 hours, then cooled to ambient and filtered through Celite. The filtrate was concentrated to a brown oil, redissolved in methylene chloride, filtered through Celite, and then concentrated under vacuum to a viscous oil in a 54% yield.

purified by silica gel chromatography using 20% acetone/isohexane as eluent. MEA was obtained as a yellow oil in 41% yield. $^1$H NMR (400 MHz, CDCl$_3$, δ): 0.88 (m, 12H), 1.29 (m, 11H), 1.57 (m, 2H), 2.95 (s, 3H), 3.31 (m, 2H), 6.70 (m, 3H), 7.25 (d, 2H).

N-Methyl-N-Isotridecylbenzenaminium-BF20 (MEAH-BF20):

The above N-methyl-N-isotridecylaniline (1.5 g, 5.2 mmol) was dissolved in 100 mL of hexane. A 2 M ethereal solution of HCl (2.9 mL, 5.7 mmol) was added slowly, causing a small amount of white precipitate to form. After stirring for 2 hours, the solution was filtered and the clear, colorless filtrate was dried under vacuum to give the anilinium salt as a yellow oil in 92% yield. A slurry of the aniline HCl salt (500 mg, 1.5 mmol) and Li—BF20 (1.2 g, 1.5 mmol) was heated at reflux for 1.5 h in 100 mL cyclohexane. Once cooled to ambient, the mixture was filtered. The filtrate was concentrated, redissolved in dichloromethane, filtered through Celite, and then concentrated to give the product as a colorless oil in 49% yield. $^1$H NMR (400 MHz, CDCl$_3$, δ): 0.76 (m, 12H), 1.20 (m, 11H), 1.60 (m, 2H), 3.25 (d, J=4.9 Hz, 3H), 3.49 (m, 2H), 7.34 (m, 2H), 7.61 (m, 3H).

N-Methyl-N-Isotridecylbenzenaminium-BF28 (MEAH-BF28):

A slurry of the above aniline HCl salt (500 mg, 1.5 mmol) and Na—BF28 (1.6 g, 1.5 mmol) in 100 mL cyclohexane

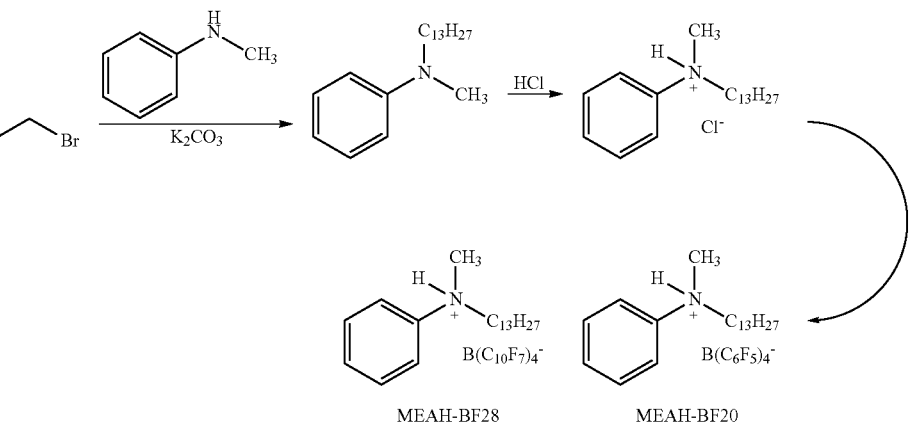

N-Methyl-N-Isotridecylaniline (MEA):

N-methylaniline (2.0 g, 18 mmol), isotridecyl bromide (5.8 g, 22 mmol), potassium carbonate (7.7 g, 55 mmol), and a catalytic amount of tetrabutylammonium iodide (approx. 100 mg) were combined in 200 mL of acetonitrile and heated at 80° C. for 16 hours. After cooling, the solution was filtered and dried under vacuum. The alkylated product was was heated at reflux for 1.5 hours. Once cooled to ambient, the supernatant was decanted away from a brown solid. The solid was dissolved in dichloromethane, filtered through Celite, and then concentrated to give the product as a brown solid in 41% yield. $^1$H NMR (400 MHz, CDCl$_3$, δ): 0.71 (m, 12H), 1.06 (m, 11H), 1.60 (m, 2H), 3.23 (d, J=4.6 Hz, 3H), 3.48 (m, 2H), 7.32 (m, 2H), 7.53 (m, 3H).

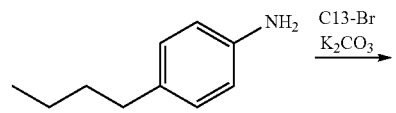

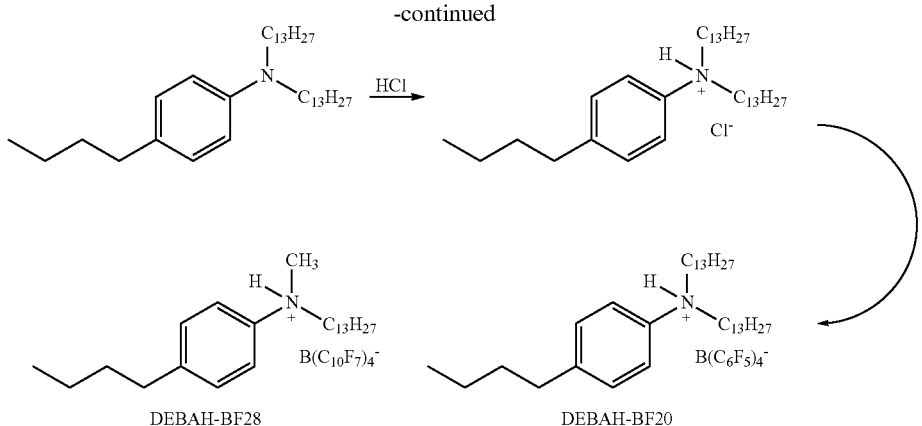

DEBAH-BF28            DEBAH-BF20

4-Butyl-N,N-Bis(Isotridecyl)Aniline (DEBA):

4-butylaniline (1.6 g, 11 mmol), isotridecyl bromide (6.2 g, 24 mmol), potassium carbonate (4.4 g, 32 mmol), and a catalytic amount of tetrabutylammonium iodide (approx. 100 mg) were combined in 200 mL of DMF and heated at 120° C. for 48 hours. After cooling, the solution was diluted with water and extracted with three portions of ethyl acetate. Combined organic fractions were washed twice with water and once with brine, then dried with MgSO$_4$, filtered and concentrated to a white solid. The dialkylated product was purified by silica gel chromatography using isohexane as eluent. It was obtained as a yellow oil in 5% yield. $^1$H NMR (400 MHz, CDCl$_3$, δ): 0.86 (m, 29H), 1.29 (m, 22H), 1.53 (m, 4H), 2.49 (t, J=7.7 Hz, 2H), 3.20 (m, 4H), 6.57 (d, J=8.2 Hz, 2H), 7.02 (d, J=8.9 Hz, 2H).

4-Butyl-N,N-Bis(Isotridecyl)Benzenaminium-BF20 (DEBAH-BF20):

The above 4-butyl-N,N-bis(isotridecyl)aniline (0.25 g, 0.49 mmol) was dissolved in 20 mL of hexane. A 2 M ethereal solution of HCl (0.26 mL, 0.51 mmol) was added slowly, causing the solution to turn pink. After stirring for 30 min, the clear solution was dried under vacuum to give the anilinium salt as a pink oil in 98% yield. A slurry of the aniline HCl salt (133 mg, 0.24 mmol) and Li—BF20 (184 mg, 0.24 mmol) was heated at reflux for 1.5 hours in 75 mL cyclohexane. Once cooled to ambient, the mixture was filtered. The filtrate was concentrated, redissolved in dichloromethane, filtered through Celite, and then concentrated to give the product as a light yellow oil in 79% yield. $^1$H NMR (400 MHz, CDCl$_3$, δ): 0.80 (m, 24H), 0.95 (t, J=7.3 Hz, 3H), 1.17 (m, 28H), 1.63 (m, 2H), 2.71 (t, J=7.7 Hz, 2H), 3.46 (m, 4H), 7.06 (m, 2H), 7.38 (d, J=8.0 Hz, 2H).

4-Butyl-N,N-Bis(Isotridecyl)Benzenaminium-BF28 (DEBAH-BF28):

A slurry of the above aniline HCl salt (133 mg, 0.24 mmol) and Na—BF28 (253 mg, 0.24 mmol) in 75 mL cyclohexane was heated at reflux for 1.5 hours. Once cooled to ambient, the mixture was filtered. The filtrate was concentrated, redissolved in dichloromethane, filtered through Celite, and then concentrated to give the product as a white solid in 70% yield. $^1$H NMR (400 MHz, CDCl$_3$, δ): 0.73 (m, 24H), 0.94 (t, J=7.3 Hz, 3H), 1.10 (m, 28H), 1.58 (m, 4H), 2.65 (t, J=7.7 Hz, 2H), 3.36 (m, 2H), 3.49 (m, 2H), 7.18 (m, 2H), 7.28 (m, 2H).

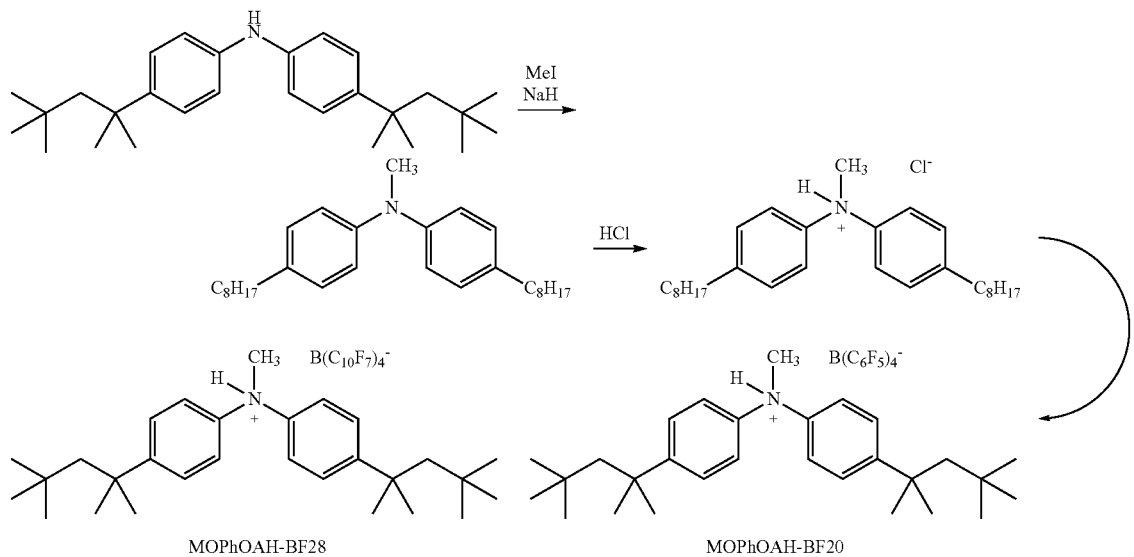

MOPhOAH-BF28            MOPhOAH-BF20

N-methyl-4-(2,4,4-trimethylpentan-2-yl)-N-(4-(2,4,4-trimethylpentan-2-yl)phenyl)aniline (MOPhOA)

Sodium hydride (0.193 g, 8.04 mmol) was added slowly to a solution of bis(2,4,4-trimethylpentan-2-yl)phenyl) amine (2.50 g, 6.35 mmol) in 100 mL THF. After stirring for 1.5 hours, methyl iodide (0.40 mL, 6.43 mmol) was added and the solution stirred an additional 16 hours. The solution was diluted with water and extracted with three portions of ethyl acetate. Combined organic fractions were washed with brine, dried with $MgSO_4$, filtered and concentrated. The methylated product was purified by silica gel chromatography using 20% acetone/isohexane solution as eluent. It was obtained as a white solid in 32% yield. $^1$H NMR (400 MHz, $CDCl_3$, δ): 0.75 (s, 18H), 1.36 (s, 8H), 1.70 (s, 4H), 3.29 (s, 3H), 6.93 (d, J=8.8 Hz, 2H), 7.25 (d, J=9.0 Hz, 2H).

N-methyl-4-(2,4,4-trimethylpentan-2-yl)-N-(4-(2,4,4-trimethylpentan-2-yl)phenyl)benzenaminium-BF20 (MOPhOAH-BF20)

N-methyl-4-(2,4,4-trimethylpentan-2-yl)-N-(4-(2,4,4-trimethylpentan-2-yl)phenyl)aniline (0.835 g, 2.05 mmol) was dissolved in 50 mL of n-hexane. A 2 M ethereal solution of HCl (1.02 mL, 2.05 mmol) was added slowly, and the reaction was stirred for 16 hours. The solution was separated into two equal portions. One portion was combined with Li—BF20 (0.770 g, 1.01 mmol) and diluted to 50 mL with cyclohexane. The mixture was heated at reflux for 1.5 hours, then cooled to ambient. The supernatant was decanted away from the residual blue oil, which was dissolved in dichloromethane and filtered. The filtrate was concentrated to give the product as a blue solid in 56% yield. $^1$H NMR (400 MHz, $CDCl_3$, δ): 0.70 (s, 18H), 1.40 (s, 8H), 1.78 (s, 4H), 3.65 (s, 3H), 7.18 (d, J=8.9 Hz, 2H), 7.60 (d, J=8.9 Hz, 2H), 9.39 (br s, 1H).

N-methyl-4-(2,4,4-trimethylpentan-2-yl)-N-(4-(2,4,4-trimethylpentan-2-yl)phenyl)benzenaminium-BF28 (MOPhOAH-BF28)

The remaining portion of N-methyl-4-(2,4,4-trimethylpentan-2-yl)-N-(4-(2,4,4-trimethylpentan-2-yl)phenyl)benzenaminium chloride solution above in n-hexane was diluted to 50 mL with cyclohexane. Na—BF28 (1.06 g, 1.01 mmol) was added and the mixture was heated at reflux for 1.5 hours. After cooling to ambient temperature, the supernatant was decanted away from the residual brown oil, which was dissolved in dichloromethane and filtered. The filtrate was concentrated to give the product as a brown solid in 36% yield. $^1$H NMR (400 MHz, $CDCl_3$, δ): 0.65 (s, 18H), 1.34 (s, 8H), 1.72 (s, 4H), 3.62 (s, 3H), 7.15 (d, J=8.4 Hz, 2H), 7.49 (d, J=8.6 Hz, 2H), 9.42 (br s, 1H).

Polymerization in Parallel Pressure Reactor

Solvents, polymerization-grade toluene, and isohexane were supplied by ExxonMobil Chemical Company and purified by passing through a series of columns: two 500 cc Oxyclear cylinders in series from Labclear (Oakland, Calif.), followed by two 500 cc columns in series packed with dried 3 Å mole sieves (8-12 mesh; Aldrich Chemical Company), and two 500 cc columns in series packed with dried 5 Å mole sieves (8-12 mesh; Aldrich Chemical Company). 1-octene (C8) and 1-hexene (C6) (98%, Aldrich Chemical Company) were dried by stirring over NaK overnight followed by filtration through basic alumina (Aldrich Chemical Company, Brockman Basic 1).

Polymerization-grade ethylene (C2) was used and further purified by passing the gas through a series of columns: 500 cc Oxyclear cylinder from Labclear (Oakland, Calif.) followed by a 500 cc column packed with dried 3 Å mole sieves (8-12 mesh; Aldrich Chemical Company) and a 500 cc column packed with dried 5 Å mole sieves (8-12 mesh; Aldrich Chemical Company).

Polymerization grade propylene (C3) was used and further purified by passing it through a series of columns: 2250 cc Oxiclear cylinder from Labclear followed by a 2250 cc column packed with 3 Å mole sieves (8-12 mesh; Aldrich Chemical Company), then two 500 cc columns in series packed with 5 Å mole sieves (8-12 mesh; Aldrich Chemical Company), then a 500 cc column packed with Selexsorb CD (BASF), and finally a 500 cc column packed with Selexsorb COS (BASF).

Solutions of the metal complexes and activators were prepared in a drybox using toluene or methylcyclohexane. Concentrations were typically 0.2 mmol/L. Tri-n-octylaluminum (TNOAL, neat, AkzoNobel) was typically used as a scavenger. Concentration of the TNOAL solution in toluene ranged from 0.5 to 2.0 mmol/L.

Polymerizations were carried out in a parallel pressure reactor, as generally described in U.S. Pat. Nos. 6,306,658; 6,455,316; 6,489,168; WO 00/09255; and Murphy, V. et al. (2003) "A Fully Integrated High-Throughput Screening Methodology for the Discovery of New Polyolefin Catalysts: Discovery of a New Class of High Temperature Single-Site Group (IV) Copolymerization Catalysts," *J. Am. Chem. Soc.*, v. 125, pp. 4306-4317, each of which is fully incorporated herein by reference. The experiments were conducted in an inert atmosphere (N2) drybox using autoclaves equipped with an external heater for temperature control, glass inserts (internal volume of reactor=23.5 mL for C2 and C2/C8; 22.5 mL for C3 runs), septum inlets, regulated supply of nitrogen, ethylene and propylene, and equipped with disposable PEEK mechanical stirrers (800 RPM). The autoclaves were prepared by purging with dry nitrogen at 110° C. or 115° C. for 5 hours and then at 25° C. for 5 hours. Although the specific quantities, temperatures, solvents, reactants, reactant ratios, pressures, and other variables are frequently changed from one polymerization run to the next, the following describes a typical polymerization performed in a parallel pressure reactor.

Catalyst systems dissolved in solution were used in the polymerization examples below, unless specified otherwise.

Ethylene-Octene Copolymerization (EO).

A pre-weighed glass vial insert and disposable stirring paddle were fitted to each reaction vessel of the reactor, which contains 48 individual reaction vessels. The reactor was then closed and purged with ethylene. Each vessel was charged with enough solvent (typically isohexane) to bring the total reaction volume, including the subsequent additions, to the desired volume, typically 5 mL 1-octene, if required, was injected into the reaction vessel and the reactor was heated to the set temperature and pressurized to the predetermined pressure of ethylene, while stirring at 800 rpm. The aluminum compound (such as tri-n-octylaluminum) in toluene was then injected as scavenger followed by addition of the activator solution (typically 1.0-1.2 molar equivalents).

The catalyst (and activator solutions for the runs below) were all prepared in toluene. The catalyst solution (typically 0.020-0.080 μmol of metal complex) was injected into the reaction vessel and the polymerization was allowed to proceed until a pre-determined amount of ethylene (quench value typically 20 psi) had been used up by the reaction.

Alternatively, the reaction may be allowed to proceed for a set amount of time (maximum reaction time typically 30 minutes). Ethylene was added continuously (through the use of computer controlled solenoid valves) to the autoclaves during polymerization to maintain reactor gauge pressure (P setpt, +/−2 psig) and the reactor temperature (T) was monitored and typically maintained within +/−1° C. The reaction was quenched by pressurizing the vessel with compressed air. After the reactor was vented and cooled, the glass vial insert containing the polymer product and solvent was removed from the pressure cell and the inert atmosphere glove box, and the volatile components were removed using a Genevac HT-12 centrifuge and Genevac VC3000D vacuum evaporator operating at elevated temperature and reduced pressure. The vial was then weighed to determine the yield of the polymer product. The resultant polymer was analyzed by Rapid GPC (see below) to determine the molecular weight, by FT-IR (see below) to determine percent octene incorporation, and by DSC (see below) to determine melting point ($T_m$).

Polymer Characterization.

Polymer sample solutions were prepared by dissolving polymer in 1,2,4-trichlorobenzene (TCB, 99+% purity from Sigma-Aldrich) containing 2,6-di-tert-butyl-4-methylphenol (BHT, 99% from Aldrich) at 165° C. in a shaker oven for approximately 3 hours. The typical concentration of polymer in solution was between 0.1 to 0.9 mg/mL with a BHT concentration of 1.25 mg BHT/mL of TCB.

To determine various molecular weight related values by GPC, high temperature size exclusion chromatography was performed using an automated "Rapid GPC" system as generally described in U.S. Pat. Nos. 6,491,816; 6,491,823; 6,475,391; 6,461,515; 6,436,292; 6,406,632; 6,175,409; 6,454,947; 6,260,407; and 6,294,388; each of which is fully incorporated herein by reference. This apparatus has a series of three 30 cm×7.5 mm linear columns, each containing PLgel 10 μm, Mix B. The GPC system was calibrated using polystyrene standards ranging from 580 to 3,390,000 g/mol. The system was operated at an eluent flow rate of 2.0 mL/minutes and an oven temperature of 165° C. 1,2,4-trichlorobenzene was used as the eluent. The polymer samples were dissolved in 1,2,4-trichlorobenzene at a concentration of 0.28 mg/mL and 400 uL of a polymer solution was injected into the system. The concentration of the polymer in the eluent was monitored using an evaporative light scattering detector. The molecular weights presented are relative to linear polystyrene standards and are uncorrected, unless indicated otherwise.

Differential Scanning Calorimetry (DSC) measurements were performed on a TA-Q100 instrument to determine the melting point ($T_m$) of the polymers. Samples were pre-annealed at 220° C. for 15 minutes and then allowed to cool to room temperature overnight. The samples were then heated to 220° C. at a rate of 100° C./min and then cooled at a rate of 50° C./min. Melting points were collected during the heating period.

The weight percent of ethylene incorporated in polymers was determined by rapid FT-IR spectroscopy on a Bruker Equinox 55+IR in reflection mode. Samples were prepared in a thin film format by evaporative deposition techniques. FT-IR methods were calibrated using a set of samples with a range of known wt % ethylene content. For ethylene-1-octene copolymers, the wt % octene in the copolymer was determined via measurement of the methyl deformation band at −1375 cm$^{-1}$. The peak height of this band was normalized by the combination and overtone band at −4321 cm$^{-1}$, which corrects for path length differences.

Equivalence is determined based on the mole equivalents relative to the moles of the transition metal in the catalyst complex.

RUN 1: Ethylene-Octene Copolymerization:

A series of ethylene-octene polymerizations were performed in the parallel pressure reactor according to the procedure described above. In these studies rac-dimethylsilyl-bis(indenyl)hafnium dimethyl (MCN-1) was used along with the activators identified in the tables below. In a typical experiment an automated syringe was used to introduce into the reactor the following reagents, if utilized, in the following order: isohexane (0.50 mL), 1-octene (100 μL), additional isohexane (0.50 mL) an isohexane solution of TNOAL scavenger (0.005 M, 100 μL), additional isohexane (0.50 mL), a toluene solution of the respective polymerization catalyst (100 μL, 0.2 mM, 20 nm [cat]/100 μL [toluene]), additional isohexane (0.50 mL), a toluene solution of the respective activator (110 μL, 0.2 mM, (20 nm [act]/100 μL [diluent])), then additional isohexane so that the total solvent volume for each run was 5 mL. Catalyst and activator were used in a 1:1.1 ratio. Each reaction was performed at a specified temperature range between 50 and 120° C., typically 100° C., while applying about 100 psig of ethylene (monomer) gas. Each reaction was allowed to run for about 20 minutes (~1200 seconds) or until approximately 20 psig of ethylene gas uptake was observed, at which point the reactions were quenched with air (~300 psig). When sufficient polymer yield was attained (e.g., at least −10 mg), the polyethylene product was analyzed by Rapid GPC. Run conditions and data are reported in Table A.

TABLE A

Data for the Copolymerization of Ethylene and Octene in isohexane.
General conditions: MCN-1 = 20 nmol; activator = 22 nmol; 1-octene = 100 μL;
solvent = isohexane; total volume = 5 mL; tri(n-octyl)aluminum = 500 nmol,
T = 100° C., P = 100 psi

| run | catalyst | activator | Octene incorp (wt %) | time (s) | yield (mg) | activity (kg/mmol/h) | Mw (g/mol) | Mn (g/mol) | Mw/Mn | $T_m$ (° C.) |
|---|---|---|---|---|---|---|---|---|---|---|
| 1 | MCN-1 | DMAH-BF20 | 22 | 23.7 | 61 | 463.3 | 289,346 | 148,240 | 2.0 | 81.6 |
| 2 | MCN-1 | DMAH-BF20 | 27 | 23.3 | 64 | 494.4 | 255,155 | 131,729 | 1.9 | 49.5 |
| 3 | MCN-1 | DMAH-BF20 | 29 | 21.9 | 76 | 624.7 | 228,024 | 109,798 | 2.1 | 46.9 |
| 4 | MCN-1 | DMAH-BF28 | 21 | 34.9 | 62 | 319.8 | 474,986 | 271,287 | 1.8 | 81.4 |
| 5 | MCN-1 | DMAH-BF28 | 27 | 30.7 | 68 | 398.7 | 416,782 | 230,410 | 1.8 | 51.8 |
| 6 | MCN-1 | DMAH-BF28 | 28 | 44.4 | 56 | 227.0 | 485,603 | 257,845 | 1.9 | 51.3 |
| 7 | MCN-1 | DMAH-BF28 | 30 | 26.7 | 67 | 451.7 | 422,391 | 235,382 | 1.8 | 52.7 |
| 8 | MCN-1 | MEAH-BF20 | 26 | 63.2 | 38 | 108.2 | 407,948 | 233,074 | 1.8 | 65.4 |
| 9 | MCN-1 | MEAH-BF20 | 27 | 26.7 | 58 | 391.0 | 330,038 | 163,007 | 2.0 | 68.1 |

TABLE A-continued

Data for the Copolymerization of Ethylene and Octene in isohexane.
General conditions: MCN-1 = 20 nmol; activator = 22 nmol; 1-octene = 100 μL;
solvent = isohexane; total volume = 5 mL; tri(n-octyl)aluminum = 500 nmol,
T = 100° C., P = 100 psi

| run | catalyst | activator | Octene incorp (wt %) | time (s) | yield (mg) | activity (kg/mmol/h) | Mw (g/mol) | Mn (g/mol) | Mw/Mn | $T_m$ (° C.) |
|---|---|---|---|---|---|---|---|---|---|---|
| 10 | MCN-1 | MEAH-BF20 | 28 | 17.3 | 68 | 707.5 | 248,634 | 119,873 | 2.1 | 49 |
| 11 | MCN-1 | MEAH-BF20 | 31 | 20.7 | 73 | 634.8 | 228,445 | 102,056 | 2.2 | 46.8 |
| 12 | MCN-1 | MEAH-BF28 | 22 | 36.4 | 59 | 291.8 | 515,558 | 274,841 | 1.9 | 76.2 |
| 13 | MCN-1 | MEAH-BF28 | 26 | 31.7 | 62 | 352.1 | 471,070 | 247,266 | 1.9 | 64.5 |
| 14 | MCN-1 | MEAH-BF28 | 29 | 25.6 | 66 | 464.1 | 420,361 | 211,658 | 2.0 | 50.3 |
| 15 | MCN-1 | MEAH-BF28 | 32 | 30.7 | 68 | 398.7 | 460,248 | 264,657 | 1.7 | 49.3 |
| 16 | MCN-1 | DEBAH-BF20 | 21 | 85.1 | 48 | 101.5 | 449,598 | 246,464 | 1.8 | 77 |
| 17 | MCN-1 | DEBAH-BF20 | 25 | 47.9 | 53 | 199.2 | 329,861 | 179,346 | 1.8 | 66.6 |
| 18 | MCN-1 | DEBAH-BF20 | 27 | 90.8 | 52 | 103.1 | 355,554 | 207,730 | 1.7 | 58.1 |
| 19 | MCN-1 | DEBAH-BF20 | 28 | 94.1 | 55 | 105.2 | 373,546 | 210,989 | 1.8 | 60 |
| 20 | MCN-1 | DEBAH-BF28 | 24 | 35.8 | 55 | 276.5 | 487,576 | 262,948 | 1.9 | 69.8 |
| 21 | MCN-1 | DEBAH-BF28 | 26 | 38.7 | 61 | 283.7 | 484,924 | 267,902 | 1.8 | 61.8 |
| 22 | MCN-1 | DEBAH-BF28 | 28 | 47 | 61 | 233.6 | 494,079 | 247,699 | 2.0 | 62.2 |
| 23 | MCN-1 | DEBAH-BF28 | 29 | 50.7 | 61 | 216.6 | 488,045 | 272,856 | 1.8 | 56.1 |

RUN 2: Ethylene Homopolymerization.

The reactor was prepared as described above and purged with ethylene. For the examples in Table B, the catalyst and activator solutions were prepared in toluene. Isohexane was then injected into each vessel at room temperature followed by a predetermined amount of ethylene gas. The reactor was heated to the set temperature while stirring at 800 rpm, and the scavenger, activator and catalyst solutions were injected sequentially to each vessel. The polymerization was allowed to proceed as described previously. The data and run conditions are shown in Table B.

RUN 3: Propylene Homopolymerization.

The reactor was prepared as described above and purged with propylene. For the examples in Table C, the catalyst and activator solutions were prepared in toluene. Isohexane was then injected into each vessel at room temperature followed by a predetermined amount of propylene gas. The reactor was heated to the set temperature while stirring at 800 rpm, and the scavenger, activator and catalyst solutions were injected sequentially to each vessel. The polymerization was allowed to proceed as described previously. The data and run conditions are shown in Table C.

TABLE B

Data for the homopolymerization of Ethylene in isohexane.
General conditions: MCN-1 = 20 nmol; activator = 22 nmol; solvent = isohexane;
total volume = 5 mL; tri(n-octyl)aluminum = 500 nmol; T = 100° C., P = 100 psi

| run | Catalyst | activator | time (s) | yield (mg) | activity (kg/mmol/h) | Mw (g/mol) | Mn (g/mol) | Mw/Mn | $T_m$ (° C.) |
|---|---|---|---|---|---|---|---|---|---|
| 1 | MCN-1 | DMAH-BF20 | 24.6 | 56 | 409.8 | 574,872 | 259,294 | 2.2 | 133.9 |
| 2 | MCN-1 | DMAH-BF20 | 23 | 55 | 430.4 | 530,300 | 256,267 | 2.1 | 134.2 |
| 3 | MCN-1 | DMAH-BF20 | 31.2 | 37 | 213.5 | 691,287 | 383,494 | 1.8 | 134.8 |
| 4 | MCN-1 | DMAH-BF20 | 34 | 38 | 201.2 | 638,374 | 295,522 | 2.2 | 134.9 |
| 5 | MCN-1 | DMAH-BF28 | 40.1 | 58 | 260.3 | 846,015 | 374,834 | 2.3 | 134.6 |
| 6 | MCN-1 | DMAH-BF28 | 36.9 | 59 | 287.8 | 796,331 | 371,308 | 2.1 | 134.6 |
| 7 | MCN-1 | DMAH-BF28 | 40.2 | 50 | 223.9 | 833,068 | 428,045 | 1.9 | 134.9 |
| 8 | MCN-1 | DMAH-BF28 | 31.3 | 52 | 299.0 | 725,211 | 358,767 | 2.0 | 134.9 |
| 9 | MCN-1 | MEAH-BF20 | 80.7 | 49 | 109.3 | 722,313 | 363,714 | 2.0 | 134.3 |
| 10 | MCN-1 | MEAH-BF20 | 84.7 | 43 | 91.4 | 778,191 | 384,237 | 2.0 | 134.3 |
| 11 | MCN-1 | MEAH-BF20 | 47 | 44 | 168.5 | 700,482 | 350,364 | 2.0 | 134.1 |
| 12 | MCN-1 | MEAH-BF20 | 43 | 44 | 184.2 | 601,330 | 301,125 | 2.0 | 134.4 |
| 13 | MCN-1 | MEAH-BF28 | 59.9 | 61 | 183.3 | 1,001,518 | 461,263 | 2.2 | 134.3 |
| 14 | MCN-1 | MEAH-BF28 | 28.8 | 60 | 375.0 | 869,966 | 408,515 | 2.1 | 134.8 |
| 15 | MCN-1 | MEAH-BF28 | 23.3 | 53 | 409.4 | 643,445 | 267,212 | 2.4 | 134.6 |
| 16 | MCN-1 | MEAH-BF28 | 23.2 | 54 | 419.0 | 688,237 | 270,874 | 2.5 | 134.4 |
| 17 | MCN-1 | DEBAH-BF20 | 40.8 | 57 | 251.5 | 788,373 | 370,362 | 2.1 | 134.8 |
| 18 | MCN-1 | DEBAH-BF20 | 24.4 | 48 | 354.1 | 629,052 | 287,440 | 2.2 | 134.6 |
| 19 | MCN-1 | DEBAH-BF20 | 20.3 | 52 | 461.1 | 541,195 | 252,197 | 2.1 | 134.8 |
| 20 | MCN-1 | DEBAH-BF20 | 25.6 | 46 | 323.4 | 677,120 | 323,575 | 2.1 | 134.7 |
| 21 | MCN-1 | DEBAH-BF28 | 71.1 | 59 | 149.4 | 996,200 | 486,059 | 2.1 | 134.8 |
| 22 | MCN-1 | DEBAH-BF28 | 22.8 | 56 | 442.1 | 700,721 | 329,309 | 2.1 | 134.9 |
| 23 | MCN-1 | DEBAH-BF28 | 32.1 | 46 | 257.9 | 766,530 | 392,465 | 2.0 | 135.1 |
| 24 | MCN-1 | DEBAH-BF28 | 31.6 | 44 | 250.6 | 837,962 | 364,046 | 2.3 | 134.7 |

TABLE C

Data for the homopolymerization of propylene in isohexane.
General conditions: MCN-1 = 30 nmol; activator = 33 nmol;
solvent = isohexane; total volume = 5 mL; tri(n-octyl)aluminum =
500 nmol; T = 100° C.; P = 160 PSI

| run | catalyst | activator | time (s) | yield (mg) | activity (kg/mmol/h) | Mw (g/mol) | Mn (g/mol) | Mw/Mn | $T_m$ (° C.) |
|---|---|---|---|---|---|---|---|---|---|
| 1 | MCN-1 | DMAH-BF28 | 56 | 92 | 196 | 96,445 | 58,590 | 1.6 | 123.5 |
| 2 | MCN-1 | DMAH-BF28 | 80 | 109 | 164 | 93,073 | 56,302 | 1.7 | 124.4 |
| 3 | MCN-1 | DMAH-BF28 | 81 | 85 | 126 | 87,587 | 53,493 | 1.6 | 124.6 |
| 4 | MCN-1 | DMAH-BF28 | 52 | 79 | 182 | 86,803 | 49,369 | 1.8 | 123.6 |
| 5 | MCN-1 | DEMAH-BF20 | 182 | 48 | 32 | 44,444 | 27,917 | 1.6 | 112.6 |
| 6 | MCN-1 | DEMAH-BF20 | 280 | 45 | 19 | 41,540 | 24,399 | 1.7 | 113.7 |
| 7 | MCN-1 | DEMAH-BF20 | 232 | 59 | 31 | 49,871 | 29,728 | 1.7 | 120.5 |
| 8 | MCN-1 | DEMAH-BF20 | 168 | 44 | 32 | 52,481 | 33,799 | 1.6 | 115.8 |
| 9 | MCN-1 | DEMAH-BF28 | 278 | 58 | 25 | 103,238 | 71,508 | 1.4 | 125.1 |
| 10 | MCN-1 | DEMAH-BF28 | 205 | 62 | 36 | 97,833 | 62,912 | 1.6 | 124.7 |
| 11 | MCN-1 | DEMAH-BF28 | 257 | 46 | 21 | 105,604 | 68,249 | 1.5 | 125.1 |

Polymerization of 1-Hexene

1-Hexene Polymerization:

A series of 1-hexene polymerizations were performed in 20 mL scintillation vials. In these studies, the metallocenes rac-dimethylsilyl-bis(indenyl)hafnium dimethyl (MCN-1) and 1,1'-bis(4-triethylsilylphenyl)methylene-(cyclopentadienyl)(2,7-di-tertiary-butyl-fluoren-9-yl)hafnium dimethyl (MCN-2) were used with various ammonium borate activators. The data and run conditions are shown in Table D.

Polymerization procedure: A 20 mL scintillation vial was charged with 2.0 mL 1-hexene, 4.9 mL isohexane, and 1 mL 0.010 mM TNOA solution in isohexane. 1.1 mL of prepared 0.5 mM solution in toluene of the activators were injected. Finally, 1 mL of 0.5 mM catalyst solution in isohexane was added. After stirring rapidly for the designated amount of time at room temperature, the reactions were quenched upon exposure to air. The polymer product was isolated upon evaporation of the volatiles under a stream of nitrogen.

TABLE D

Data for the homopolymerization of 1-hexene in isohexane.
General conditions: MCN-1 = 500 nmol; activator = 550 nmol;
solvent = isohexane; total volume = 10 mL; tri(n-octyl)aluminium = 10 μmol

| run | catalyst | activator | time (s) | yield (g) | activity (kg/nmol/h) | Mw (g/mol) | Mn (g/mol) | Mw/Mn |
|---|---|---|---|---|---|---|---|---|
| 1 | MCN-1 | DMAH-BF28 | 4 | 0.358 | 0.179 | 43,976 | 22,068 | 1.99 |
| 2 | MCN-1 | MOPhOAH-BF28 | 4 | 0.230 | 0.115 | 44,107 | 21,985 | 2.01 |
| 3 | MCN-2 | DMAH-BF20 | 0.5 | 1.144 | 4.58 | 799,514 | 326,185 | 2.45 |
| 4 | MCN-1 | MOPhOAH-BF20 | 0.5 | 0.282 | 1.13 | 1,526,549 | 468,387 | 3.26 |

All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

What is claimed is:

1. A compound represented by Formula (AI):

wherein:
   E is nitrogen or phosphorous;
   d is 1, 2 or 3; k is 1, 2, or 3; n is 1, 2, 3, 4, 5, or 6; n−k=d;
   each of $R^1$, $R^2$, and $R^3$ is independently hydrogen, a $C_1$-$C_{40}$ branched or linear alkyl, or a $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms and at least one of $R^1$, $R^2$, or $R^3$ is a $C_7$-$C_{40}$ branched alkyl; M is an element selected from group 13 of the Periodic Table of the Elements; and
   each Q is independently a hydride, bridged or unbridged dialkylamido, halide, alkoxide, aryloxide, hydrocarbyl, substituted hydrocarbyl, halocarbyl, substituted halocarbyl, or halosubstituted-hydrocarbyl radical.

2. A compound represented by Formula (I):

wherein:
   E is nitrogen or phosphorous;
   each of $R^1$, $R^2$, and $R^3$ is independently $C_1$-$C_{40}$ branched or linear alkyl, $C_5$-$C_{50}$-aryl, wherein each of $R^1$, $R^2$, and $R^3$ is independently unsubstituted or substituted with at least one of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl; wherein $R^1$, $R^2$, and $R^3$ together comprise 15 or more carbon atoms and at least one of $R^1$, $R^2$, or $R^3$ is a $C_5$-$C_{40}$ branched alkyl; and each of $R^4$, $R^5$, $R^6$, and $R^7$ is naphthyl, wherein at least one of $R^4$, $R^5$, $R^6$, and $R^7$ is substituted with from one to seven fluorine atoms.

3. The compound of claim 1, wherein: at least one of $R^1$, $R^2$, and $R^3$ is independently a $C_3$-$C_{40}$ branched alkyl which is unsubstituted or substituted with at least one of halide, $C_5$-$C_{15}$ aryl, $C_6$-$C_{25}$ arylalkyl, and $C_6$-$C_{25}$ alkylaryl.

4. The compound of claim 1, wherein E is nitrogen.

5. The compound of claim 1, wherein each of $R^4$, $R^5$, $R^6$, and $R^7$ is substituted with from one to seven fluorine atoms.

6. The compound of claim 1, wherein: $R^1$ is a methyl group; $R^2$ is $C_{10}$-$C_{42}$ aryl; $R^3$ is independently $C_7$-$C_{40}$ branched alkyl; wherein each of $R^2$ and $R^3$ is independently unsubstituted or substituted with at least one of halide, $C_5$-$C_{15}$ aryl, $C_6$-$C_{25}$ arylalkyl, $C_6$-$C_{25}$ alkylaryl, and in the case of the $C_{10}$ to $C_{42}$ aryl, $C_1$-$C_{10}$ alkyl; and $R^2$ and $R^3$ together comprise 20 or more carbon atoms.

7. The compound of claim 1, wherein all Q are perfluoroaryl.

8. The compound of claim 1, wherein $R^1$, $R^2$, and $R^3$ together comprise 25 or more carbon atoms.

9. The compound of claim 1, wherein $R^1$, $R^2$, and $R^3$ together comprise 35 or more carbon atoms.

10. The compound of claim 1, wherein the branched alkyl is represented by the formula:

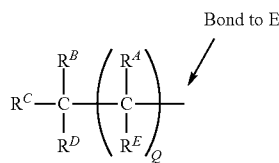

Bond to E wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$-C- $R^E$) group, one or both of $R^A$ and $R^E$ is not H; and $R^C$, $R^B$ and $R^D$ are hydrogen; and Q is an integer from 5 to 40.

11. The compound of claim 1 wherein one or two of $R^1$, $R^2$ and $R^3$ are independently represented by the formula (IV) where:

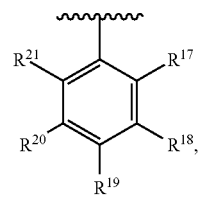

(IV)

each of $R^{17}$, $R^{18}$, $R^{19}$ $R^{20}$, and $R^{21}$ is independently selected from hydrogen, $C_1$-$C_{40}$ hydrocarbyl or $C_1$-$C_{40}$ substituted hydrocarbyl, a heteroatom, such as halogen, a heteroatom-containing group, or is represented by formula (BIII), provided that at least one of $R^{17}$, $R^{18}$, $R^{19}$ $R^{20}$, and $R^{21}$ is not hydrogen, where formula (BIII) is:

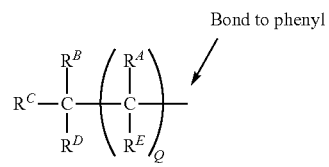

Bond to phenyl wherein each of $R^A$ and $R^E$ are independently H, a $C_1$-$C_{40}$ linear or branched alkyl or $C_5$-$C_{50}$-aryl, wherein each of $R^A$ and $R^E$ is optionally substituted with one or more of halide, $C_5$-$C_{50}$ aryl, $C_6$-$C_{35}$ arylalkyl, $C_6$-$C_{35}$ alkylaryl and, in the case of the $C_5$-$C_{50}$-aryl, $C_1$-$C_{50}$ alkyl, provided that in at least one ($R^A$-C- $R^E$) group, one or both of $R^A$ and $R^E$ is not H;

$R^C$, $R^B$ and $R^D$ are hydrogen; and
Q is an integer from 5 to 40.

12. The compound of claim 1, wherein $R^1$ is $C_1$-$C_{10}$ alkyl and each of $R^2$ and $R^3$ is $C_{10}$-$C_{40}$ branched alkyl.

13. The compound of claim 1, wherein $R^1$ is methyl, $R^2$ is $C_{10}$-$C_{40}$ branched alkyl, and $R^3$ is substituted phenyl.

14. The compound of claim 1, wherein $R^1$ is phenyl, $R^2$ is methyl, and $R^3$ is branched $C_{10}$-$C_{40}$ alkyl.

15. The compound of claim 1, wherein the compound has a solubility of more than 10 mM at 25° C. (stirred 2 hours) in methylcyclohexane.

16. The compound of claim 1, wherein the compound has a solubility of more than 1 mM at 25° C. (stirred 2 hours) in isohexane.

17. A catalyst system comprising a catalyst, the activator compound of claim 1, and optional support.

18. The catalyst system of claim 17, wherein the support material is selected from $Al_2O_3$, $ZrO_2$, $SiO_2$, $SiO_2/Al_2O_3$, $SiO_2/TiO_2$, silica clay, silicon oxide/clay, or mixtures thereof.

* * * * *